(12) United States Patent
Haggard et al.

(10) Patent No.: US 8,993,540 B2
(45) Date of Patent: Mar. 31, 2015

(54) COMPOSITIONS AND METHODS FOR DELIVERING AN AGENT TO A WOUND

(75) Inventors: Warren O. Haggard, Bartlett, TN (US); Scott P. Noel, Arlington, TN (US); Joel D. Bumgardner, Memphis, TN (US)

(73) Assignee: University of Memphis Research Foundation, Memphis, TN (US)

( * ) Notice: Subject to any disclaimer, the term of this patent is extended or adjusted under 35 U.S.C. 154(b) by 42 days.

(21) Appl. No.: 13/256,585

(22) PCT Filed: Mar. 16, 2010

(86) PCT No.: PCT/US2010/027481
§ 371 (c)(1),
(2), (4) Date: Feb. 27, 2012

(87) PCT Pub. No.: WO2010/107794
PCT Pub. Date: Sep. 23, 2010

(65) Prior Publication Data
US 2012/0149659 A1 Jun. 14, 2012

Related U.S. Application Data

(60) Provisional application No. 61/160,539, filed on Mar. 16, 2009, provisional application No. 61/171,805, filed on Apr. 22, 2009, provisional application No. 61/227,606, filed on Jul. 22, 2009.

(51) Int. Cl.
| | | |
|---|---|---|
| *A61K 31/715* | (2006.01) | |
| *A61P 31/04* | (2006.01) | |
| *A61P 31/12* | (2006.01) | |
| *A61P 17/02* | (2006.01) | |
| *C07H 1/00* | (2006.01) | |
| *A61K 47/36* | (2006.01) | |
| *A61K 31/00* | (2006.01) | |
| *A61L 15/28* | (2006.01) | |
| *A61L 27/20* | (2006.01) | |
| *A61L 27/58* | (2006.01) | |
| *A61L 31/04* | (2006.01) | |
| *C08B 37/08* | (2006.01) | |
| *C08L 5/08* | (2006.01) | |
| *A61K 9/00* | (2006.01) | |
| *A61K 9/70* | (2006.01) | |

(52) U.S. Cl.
CPC .............. *A61K 47/36* (2013.01); *A61K 31/00* (2013.01); *A61L 15/28* (2013.01); *A61L 27/20* (2013.01); *A61L 27/58* (2013.01); *A61L 31/042* (2013.01); *C08B 37/003* (2013.01); *C08L 5/08* (2013.01); *A61K 9/0024* (2013.01); *A61K 9/7007* (2013.01)
USPC ........................................ 514/55; 536/123.1

(58) Field of Classification Search
CPC ... A61K 9/0024; A61K 9/7007; A61K 31/00; A61K 47/36; A61K 2300/00; C08L 5/08; C08B 37/003; A61L 31/042; A61L 27/58; A61L 27/20; A61L 15/28
USPC ........................................ 514/55; 536/123.1
See application file for complete search history.

(56) References Cited

U.S. PATENT DOCUMENTS

| | | | | |
|---|---|---|---|---|
| 4,895,724 | A | * | 1/1990 | Cardinal et al. .............. 424/418 |
| 5,541,233 | A | * | 7/1996 | Roenigk ......................... 521/54 |
| 5,958,443 | A | | 9/1999 | Viegas et al. |
| 6,699,287 | B2 | | 3/2004 | Son et al. |
| 6,989,157 | B2 | * | 1/2006 | Gillis et al. .................... 424/618 |
| 7,371,403 | B2 | | 5/2008 | McCarthy et al. |
| 2003/0015825 | A1 | | 1/2003 | Sugie et al. |
| 2003/0206958 | A1 | | 11/2003 | Cattaneo et al. |
| 2007/0059473 | A1 | * | 3/2007 | Yamazaki et al. ........... 428/40.1 |
| 2009/0004276 | A1 | | 1/2009 | Ben-Shalom et al. |
| 2009/0075383 | A1 | | 3/2009 | Buschmann et al. |

FOREIGN PATENT DOCUMENTS

| | | | | |
|---|---|---|---|---|
| EP | 1 308 177 | A1 | 5/2003 | |
| JP | 02-268766 | | 11/1990 | |
| JP | 2003-511120 | | 3/2003 | |
| JP | 2004-231604 | | 8/2004 | |
| JP | 2006-347999 | | 6/2005 | |
| JP | 2006-516988 | | 7/2006 | |
| JP | 2008-110208 | | 5/2008 | |
| JP | 2008-161502 | | 7/2008 | |
| JP | 2008-527033 | | 7/2008 | |
| KR | 10-2002-0017552 | | 3/2002 | |
| KR | 2002-0017552 | * | 3/2002 | .............. A61L 27/60 |
| KR | 102002001755 | A * | 7/2002 | .............. A61L 27/60 |
| KR | 10-2004-0090033 | | 10/2004 | |
| KR | 20040090033 | * | 10/2004 | .............. A61L 27/60 |
| KR | 2007 0118730 | A | 12/2007 | |

(Continued)

OTHER PUBLICATIONS

Merck Manual, 1992, pp. 183-189, 1460-65.*

(Continued)

*Primary Examiner* — Ganapathy Krishnan

(74) *Attorney, Agent, or Firm* — Saul Ewing LLP; Melissa Hunter-Ensor

(57) ABSTRACT

The invention provides compositions featuring chitosan and methods for using such compositions for the local delivery of biologically active agents to an open fracture, complex wound or other site of infection. Advantageously, the degradation and drug elution profiles of the chitosan compositions can be tailored to the needs of particular patients at the point of care (e.g., in a surgical suite, clinic, physician's office, or other clinical setting).

17 Claims, 33 Drawing Sheets

(56) References Cited

FOREIGN PATENT DOCUMENTS

| WO | WO 01/41820 A1 | 6/2001 |
|---|---|---|
| WO | WO 2004/078063 A2 | 9/2004 |
| WO | WO 2008/157318 A2 | 12/2008 |
| WO | WO 2009/056602 A1 | 5/2009 |

OTHER PUBLICATIONS

Antonov et al., "Study of Wound Healing Properties of Chitosan", Russian Agricultural Sciences, vol. 34, No. 6, pp. 426-427 (2008).

Kiang et al., "The effect of the degree of chitosan deacetylation on the efficiency of gene transfection", Biomaterials, vol. 25, pp. 5293-5301 (2004).

Niekraszewicz; "Chitosan Medical Dressings", Institute of Chemical Fibres ul. M. Skłodowskiej-Curie 19/27, 90-570 Łódź, Poland, Fibres & Textiles in Eastern Europe Jan./Dec. 2005, vol. 13, No. 6 (54).

Bonferoni et al., "Chitosan Gels for the Vaginal Delivery of Lactic Acid: Relevance of Formulation Parameters to Mucoadhesion and Release Mechanisms", AAPS PharmSciTech 2006; 7 (4) Article 104 (http://www.aapspharmscitech.org).

International Search Report issued for International Application No. PCT/US2010/027481, completed Oct. 28, 2010 and mailed Nov. 2, 2010.

European Search Report issued in European Patent Application No. 10753982.7 on Aug. 6, 2013.

JP Office Action, issued in JP App No. 2012-500887 (translation), mailed Jan. 7, 2015.

* cited by examiner

COMPOSITIONS AND METHODS FOR DELIVERING AN AGENT TO A WOUND

CROSS-REFERENCE TO RELATED APPLICATIONS

This application is a 35 U.S.C. §371 U.S. national entry of International Application PCT/US2010/027481 (WO 2010/107794) having an International filing date of Mar. 16, 2010 which claims the benefit of the following U.S. Provisional Application Ser. Nos. 61/160,539, filed Mar. 16, 2009, 61/171,805, filed Apr. 22, 2009, and 61/227,606, filed Jul. 22, 2009; the entire contents of each of which are incorporated herein by this reference.

STATEMENT OF RIGHTS TO INVENTIONS MADE UNDER FEDERALLY SPONSORED RESEARCH

This work was supported by the following grants from the U.S. Army: AMEDD Grant No. W81 XWH-080312. The government has certain rights in the invention.

BACKGROUND OF THE INVENTION

The skin serves as an important barrier to infection. Any trauma that breaks the skin creates an opportunity for pathogen entry and infection. Open fractures are ideal sites for infection. Surgical site infections in closed fractures range from 3.6-8.1%. In contrast, surgical site infections in open fractures range from 17.5-21.2%. Pathogens present at the site of an open fracture may create not only local infections, but can also cause serious infections in the bone and associated tissues. Complex open wounds are also prone to infection with a number of bacteria. The type of bacteria infecting the wound typically varies depending on the cause of the trauma. To reduce the risk of infection, the current standard of care involves debridement, irrigation, and systemic antibiotic therapy. Even with aggressive therapies and systemic antibiotic treatment, infections remain a significant source of morbidity and mortality. Tissues compromised by trauma and infection often have reduced vascularization, which limits the delivery of circulating therapeutics. Increased concentrations of systemic antibiotics are usually required to compensate for poor circulation in the damaged tissue. Antibiotic toxicity and systemic side effects are serious problems associated with this course of therapy. Infections following surgery, drug side effects, and related complications can significantly increase hospital stays and result in adverse outcomes. Because current methods for treating or preventing infection, particularly infections related to open fractures, are inadequate, improved compositions and methods for providing agents to prevent or treat an infection at a site of trauma are urgently required.

SUMMARY OF THE INVENTION

As described below, the present invention features chitosan compositions that provide for the delivery of biologically active agents for the treatment or prevention of a pathogen infection. Advantageously, the degradation and drug elution profiles of the chitosan compositions can be tailored to the needs of particular patients at the point of care (e.g., in a surgical suite, clinic, physician's office, or other clinical setting).

In one aspect, the invention features a method for producing a biodegradable chitosan composition having a desired biodegradation profile, the method involving dissolving chitosan having a uniform degree of deacetylation of at about 51% in one or more acids in a solvent, where the acid and the solvent are selected to produce a chitosan that biodegrades over at least about one, two, three, four, five, six, seven, eight, nine, ten days or more in vivo; and forming the chitosan into a desired shape under conditions that reduce the water content by about 10%-100% (e.g., 10%, 20%, 30%, 40%, 50%, 60%, 70%, 80%, 90%, 100%). In one embodiment, the method further involves contacting the chitosan composition with an effective amount of at least one agent and/or incorporating an effective amount of at least one agent into the chitosan composition at a point of care.

In another aspect, the invention features a method for producing a biodegradable chitosan composition having a desired biodegradation profile, the method involving dissolving chitosan having a uniform degree of deacetylation of at about 51% in one or more acids in a solvent, where the acid and the solvent are selected to produce a chitosan that biodegrades over at least about one, two, three, four, five, six, seven, eight, nine, ten days or more in vivo; forming the chitosan into a desired shape under conditions that reduce the water content by about 10%-100% (e.g., 10%, 20%, 30%, 40%, 50%, 60%, 70%, 80%, 90%, 100%); and neutralizing the chitosan composition by contacting the composition with water, a neutral, or a basic solution, where the water, neutral, or basic solution is selected to modulate a physical-mechanical property of the chitosan, thereby producing a biodegradable chitosan composition. In one embodiment, the method further involves contacting the chitosan composition with an effective amount of at least one agent and/or incorporating an effective amount of at least one agent into the chitosan composition at a point of care.

In yet another aspect, the invention features a method for producing a biodegradable chitosan composition containing an agent selected by a clinician at a point of care, the method involving dissolving chitosan having a desired biodegradation profile in one or more acids in a solvent where the acid and the solvent are selected to produce a chitosan that biodegrades over at least about one, two, three, four, five, six, seven, eight, nine, ten days or more in vivo; forming the chitosan into a desired shape under conditions that reduce the water content by about 10%-100% (e.g., 10%, 20%, 30%, 40%, 50%, 60%, 70%, 80%, 90%, 100%); neutralizing the chitosan composition by contacting the composition with water, a neutral, or a basic solution, where the water, neutral, or basic solution is selected to modulate a physical-mechanical property of the chitosan; thereby producing a biodegradable chitosan composition; selecting an agent; and incorporating an effective amount of at least one agent into the chitosan composition at a point of care. In one embodiment, the composition is contacted with the agent at a point of care. In one embodiment, the agent (e.g., antimicrobial) is selected based on the source of trauma.

In another aspect, the invention features a chitosan composition produced by the method of any of the above aspects.

In another aspect, the invention features a wound management device containing a chitosan composition produced by the method of any of claims 1-21.

In one aspect, the invention features an acid-treated chitosan composition that degrades within 1-35 days in vivo containing or consisting essentially of chitosan having a uniform degree of deacetylation of at least about 51%, where the water content is about 0-90%, and an effective amount of an agent selected at the point of care.

In another aspect, the invention features a wound management device containing an acid-treated chitosan composition that degrades within 1-35 days in vivo containing or consisting essentially of chitosan having a uniform degree of deacetylation of at least about 51%, where the water content is about 0-90%, and an effective amount of an agent (e.g., antimicrobial agent, growth factor, anti-inflammatory, clot promoting agent, and/or anti-thrombotic).

In another aspect, the invention features a method for treating or preventing an infection in a subject at a site of trauma (e.g., a fracture, open fracture, wound, complex wound, and surgical site), the method involving contacting the site with a wound management device containing or consisting essentially of a chitosan composition produced according to any of claims 19 and 21-31 and an effective amount of at least one agent selected at the point of care (e.g., a surgical suite, clinic, physician's office, or other clinical setting).

In another aspect, the invention features a method for treating or preventing an infection in a subject at a site of trauma (e.g., a fracture, open fracture, wound, complex wound, and surgical site), the method involving contacting the site with a wound management device containing an acid-treated chitosan composition, said composition containing or consisting essentially of chitosan having a uniform degree of deacetylation of at least about 61% and an effective amount of at least one agent selected at the point of care.

In another aspect, the invention features a method for the local delivery of an agent to a site of trauma (e.g., a fracture, open fracture, wound, complex wound, and surgical site), the method involving contacting the site with a chitosan composition containing an agent selected at the point of care, thereby delivering the agent to the site. In one embodiment, the method further involves irrigating and debriding the site of trauma.

In another aspect, the invention features a medical device for implantation containing an acid-treated chitosan composition having a uniform degree of deacetylation of at least about 51% and further containing an effective amount of an agent. In one embodiment, the chitosan composition is a film that adheres to the device. In another embodiment, the device contains titanium or stainless steel. In yet another embodiment, the medical device is a prosthetic device.

In another aspect, the invention features a kit containing a chitosan composition of any of claim 22 or 24-36 for use in treating a trauma site or delivering an agent. In one embodiment, the chitosan composition is present in a wound management device or medical device for implantation. In another embodiment, the chitosan composition is in the form of a plug, mesh, strip, suture, dressing, sponge, film, hydrogel, or combinations thereof.

In various embodiments of any of the above aspects, the chitosan composition is in the form of a film, hydrogel, mesh, plug, strip, sponge, suture, dressing, or combinations thereof. In other embodiments of any of the above aspects, the agent is any one or more of an antimicrobial (e.g., anti-bacterial, anti-viral, and anti-fungal agents), growth factor, anti-inflammatory, hemostatic, and anti-thrombotic. In other embodiments of any of the above aspects, the anti-bacterial agent is any one or more of daptomycin, vancomycin, and amikacin. In various embodiments of the invention delineated herein, the chitosan composition contains about 1 µg-500 mg (1, 5, 10, 50, 100, 200, 300, 400, 500, 600, 700, 800, 900 µg; 1, 5, 10, 25, 50, 75, 100, 125, 150, 200, 250, 300, 350, 400, 450, 500), 100-300 (100, 125, 150, 175, 200, 225, 250, 275, 300 mg), or 200-300 (200, 300) mg antibiotic per gram chitosan. In various embodiments of any invention delineated herein, a chitosan composition releases at least about 1 µg to 1 mg of antibiotic per hour (e.g., 1, 5, 10, 25, 50, 75, 100, 200, 250, 300, 350, 400, 450, 500, 550, 600, 650, 700, 750, 800, 850, 900, 1000 µg/hour). In various embodiments of the above aspects, or any aspect of the invention delineated herein, the chitosan composition releases about 1 µg-50 mg (e.g., 1, 5, 10, 50, 100, 200, 300, 400, 500, 600, 700, 800, 900 µg; 1, 5, 10, 15, 20, 25, 30, 35, 40, 45, 50) of the agent in 12-72 hours. In other embodiments of any invention delineated herein, the chitosan composition releases about 1 µg-500 mg of the agent per cm³ sponge. In still other embodiments of any invention delineated herein, the chitosan composition releases about 15-40 mg in about 24 hours or releases about 20 mg of agent in about 24 hours. In various embodiments of the above aspects, or any aspect of the invention delineated herein, at least about 10-1000 µg (e.g., 10, 25, 50, 75, 100, 200, 250, 300, 350, 400, 450, 500, 550, 600, 650, 700, 750, 800, 850, 900, 1000 µg) of the agent is eluted from the device in one hour, twenty-four hours, or seventy two hours.

In still other embodiments of the above aspects or any other aspect of the invention delineated herein, the chitosan composition is biodegradable over at least about one, two, three, four, five, six days, over one week, two weeks, three weeks, or over one, two, three or more months. In other embodiments, the chitosan is treated with an acid that is any one or a combination of acetic, citric, oxalic, proprionic, ascorbic, hydrochloric, formic, salicylic and lactic acids. In various embodiments of an invention delineated herein, the acid or acid solvent contains 1-99% (e.g., 1, 2, 3, 4, 5, 10, 15, 20, 25, 30, 35, 40, 45, 50, 55, 60, 65, 70, 75, 80, 85, 90, 95, 99, 100%) lactic and/or 1-99% (e.g., 1, 2, 3, 4, 5, 10, 15, 20, 25, 30, 35, 40, 45, 50, 55, 60, 65, 70, 75, 80, 85, 90, 95, 99, 100%) acetic acid. In one embodiment of the above aspects, the chitosan is treated with lactic acid, acetic acid, or a combination of those two. In still other embodiments of the invention, the acid solvent is a 0.05%, 1%, 2%, 3%, 4%, or 5% acid solution containing a blend of 75% lactic acid and 25% acetic acid.

In various embodiments of an invention delineated herein, the chitosan degree of deacetylation, weight percent, neutralization solution, solvent make-up, and/or crystallinity is varied to customize the biodegradation profile, elution profile, and/or a physical-mechanical property of the chitosan composition. In various embodiments, the physical-mechanical property is selected from the group consisting of tensile strength, Young's modulus, swelling, degradation, and a combination thereof.

In still other embodiments of the invention, the effective amount of the agent is sufficient to reduce the survival or proliferation of a bacterial cell (e.g., *Pseudomonas aeruginosa* (lux) or *Staphylococcus aureus*). In still other embodiments of any of the aspects delineated herein, the method reduces bacteria present at the site by at least about 20-100% (e.g., 20, 25, 30, 35, 40, 45, 50, 55, 60, 65, 70, 75, 80, 85, 90, 95, 100%) at 72 hours after contact with the chitosan composition relative to an untreated control site. In still other embodiments, the degree of deacetylation is at least about 61, 71, or 80 percent or the composition contains a combination of chitosans each having such a percent deacetylation. In still other embodiments of any of the above aspects, chitosan percent deacetylation or weight percent is varied to customize the composition's degradation and elution rates. In still other embodiments, the acid is varied to customize the composition's degradation and elution rates. In yet other embodiments of any of the above aspects, the composition is custom loaded with an agent by a clinician at the point of treatment. In still other embodiments, the device provides for the long term release of an agent. In one preferred embodiment of the above aspects, the chitosan composition contains 61DDA or 71DDA chitosan that is neutralized with 0.175 or 0.5M NaOH. In one preferred embodiment, the chitosan composition is 80% deacetylated chitosan treated with lactic and/or acetic acid. In still other embodiments, the desired shape is obtained by freezing the chitosan in a mold and lyophilizing the chitosan to form a sponge, or by pouring the chitosan into a thin layer and heating the chitosan to form a dehydrated chitosan film. In still other embodiments of the invention, the chitosan composition is molded to form a plug, mesh, strip, suture, dressing, sponge, or film. In yet other embodiments, the chitosan composition contains a chitosan sponge in a chitosan gel, where the chitosan has a uniform degree of deacetylation of at least about 51%. In one embodiment, at least about 25%-95% of the composite is a gel component. In another embodiment, at least about 5%-75% of the composite is sponge.

In various embodiments of a method delineated herein, the method is ex vivo. In various embodiments of a method delineated herein, the chitosan degree of deacetylation, weight percent, neutralization solution, solvent make-up, and/or crystallinity is varied to customize the biodegradation profile, elution profile, and/or a physical-mechanical property of the chitosan composition.

In various embodiments of a method delineated herein, the method further involves neutralizing the chitosan composition by contacting the composition with water, a neutral, or a basic solution. In still other embodiments, the invention further involves reducing the water content by at least about 10% (e.g., 10%, 20%, 30%, 40%, 50%, 60%, 70%, 80%, 90%, 100%). In yet other embodiments of a method delineated herein, the chitosan composition biodegrades over at least about three-five days when implanted in a subject. In various embodiments of a method of any of the above aspects or any other method of the invention delineated herein, the method further involves irrigating and debriding the site of trauma.

The invention provides compositions featuring chitosan and methods for using such compositions for the local delivery of biologically active agents to an open fracture, complex wound or other site of infection. Compositions and articles defined by the invention were isolated or otherwise manufactured in connection with the examples provided below. Other features and advantages of the invention will be apparent from the detailed description, and from the claims.

DEFINITIONS

By "chitosan" is meant a chitin-derived polymer that is at least 20% deacetylated. Preferably, chitosan is at least about 50% deacetylated. Chitin is a linear polysaccharide consisting of (1-4)-linked 2-acetamido-2-deoxy-b-D-glucopyranose. Chitosan is a linear polysaccharide consisting of (1-4)-linked 2-amino-2-deoxy-b-D-glucopyranose. An exemplary chitosan polymer is shown in FIG. 15.

By "composite" is meant a mixture of materials. In one embodiment, a composite comprises sponge fragments dispersed within a hydrogel.

By "acid treated chitosan" is meant chitosan that is solubilized in an acidic solution.

By "degrades" is meant physically or chemically breaks down in whole or in part. Preferably, the degradation represents a physical reduction in the mass by at least about 10%, 25%, 50%, 75%, 80%, 85%, 90%, 95% or 100%.

By "film" is meant a thin layer of material.

By "long term release" is meant elution of an agent over the course of twenty-four-seventy two hours or longer. By "sponge" is meant a three-dimensional porous matrix.

By "wound management device" or "wound healing device" is meant any material used to protect or promote healing at a site of trauma.

By "agent" is meant any small compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a chitosan analog retains the biological activity of a corresponding reference chitosan polymer (e.g., manufactured chitosan), while having certain biochemical modifications that enhance the analog's function relative to a reference chitosan polymer. Such biochemical modifications could increase the analog's ability to be degraded, to uptake or elute a therapeutic agent, or to increase or decrease mechanical strength.

By "antimicrobial" is meant an agent that inhibits or stabilizes the proliferation or survival of a microbe. In one embodiment, a bacteriostatic agent is an antimicrobial. In other embodiments, any agent that kills a microbe (e.g., bacterium, fungus, virus) is an antimicrobial.

By "anti-inflammatory" is meant an agent that reduces the severity or symptoms of an inflammatory reaction in a tissue. An inflammatory reaction within tissue is generally characterized by leukocyte infiltration, edema, redness, pain, and/or neovascularization. Inflammation can also be measured by analyzing levels of cytokines or any other inflammatory marker.

By "biodegradable" is meant susceptible to breakdown by biological activity. For example, biodegradable chitosan compositions are susceptible to breakdown by enzymes present in vivo (e.g., lysozyme, N-acetyl-o-glucosaminidase and lipases). Degradation of a chitosan composition of the invention need not be complete. A chitosan composition of the invention may be degraded, for example, by the cleavage of one or more chemical bonds (e.g., glycosidic bonds).

By "clinician" is meant any healthcare provider. Exemplary clinicians include, but are not limited to, doctors, veterinarians, osteopaths, physician's assistants, emergency medical technicians, medics, nurse practitioners, and nurses.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "customize" is meant tailor to suit the needs of a particular subject.

By "degradation rate" is meant the time required to substantially degrade the composition. A composition is substantially degraded where at least about 75%, 85%, 90%, 95% or more has been degraded. Methods for measuring degradation of chitosan are known in the art and include measuring the amount of a sponge, film, composite or other composition of the invention that remains following implantation in a subject or following in vitro exposure to an enzyme having chitosan-degrading activity.

By "disease" is meant any condition or disorder that damages or interferes with the normal function of a cell, tissue, or organ. In one example, a disease is a bacterial or other infection present in a wound site. In another embodiment, a disease is sepsis.

By "effective amount" is meant the amount of an agent required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "elution rate" is meant the time required for an agent to be substantially released from a composition. Elution can be measured by determining how much of an agent remains within the composition or by measuring how much of an agent has been released into the composition's surroundings. Elution may be partial (10%, 25%, 50%, 75%, 80%, 85%, 90%, 95% or more) or complete. In one preferred embodiment, the agent continues to be released at an effective level for at least about 3, 4, 5, 6, 7, 8, 9, or 10 days.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on wound healing or pathogen infection described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Chitosan compositions are useful for the delivery of polynucleotides, such as inhibitory nucleic acid molecules, useful for the treatment or prevention of pathogen infection and related disease. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

By "infection" is meant the presence of one or more pathogens in a tissue or organ of a host. An infection includes the proliferation of a microbe (e.g., bacteria, viruses, fungi) within a tissue of a subject at a site of trauma.

By "marker" is meant any protein or polynucleotide having an alteration in expression level or activity that is associated with a disease or disorder.

By "modulate" is meant alter (increase or decrease). Such alterations are detected by standard art known methods such as those described herein.

As used herein, "obtaining" as in "obtaining an agent" includes synthesizing, purchasing, or otherwise acquiring the agent.

By "physical interaction" is meant an association that does not require covalent bonding. In one embodiment, a physical interaction includes incorporation into a chitosan composition of the invention.

By "point of treatment" is meant the site where healthcare is delivered. A "point of treatment" includes, but is not limited to, a surgical suite, physician's office, clinic, or hospital.

By "polymer" is meant a natural or synthetic organic molecule formed by combining smaller molecules in a regular pattern.

By "profile" is meant a set of characteristics that define a composition or process. For example, a "biodegradation profile" refers to the biodegradation characteristics of a composition. In another example, an "elution profile" refers to elution characteristics of a composition.

By "prosthetic device" is meant an implanted medical device that substitutes for or supplements a missing or defective part of the body.

By "small molecule" is meant any chemical compound.

By "trauma" is meant any injury that damages a tissue or organ of a subject. The injury need not be severe. Therefore, a trauma includes any injury that breaks the skin.

By "modulation" is meant any alteration (e.g., increase or decrease) in a biological function or activity.

By "subject" is meant a mammal, including, but not limited to, a human or non-human mammal, such as a bovine, equine, canine, ovine, or feline.

By "uniform degree of deacetylation" refers to a chitosan composition made from a single type of chitosan, (e.g., 61DDA, 71DDA, or 81DDA). In one embodiment, a chitosan composition having a uniform degree of deacetylation excludes chitosan compositions having a combination of types chitosans, where the chitosans have different degrees of deacetylation.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" is meant a standard or control condition.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

BRIEF DESCRIPTION OF THE DRAWINGS

FIG. 2A shows a dehydrated sponge prior to re-hydration. FIG. 2B shows in situ re-hydration of a chitosan sponge (average re-hydration is 6.5 ml). FIG. 2C shows a dehydrated and re-hydrated chitosan sponge after 1 minute in solution.

FIGS. 3A and 3B are the 24 hour and 48 hour ZOI images, respectively, for sponges soaked in amikacin against *Pseudomonas aeruginosa*. FIGS. 3C and 3D are the 24 hour and 48 hour ZOI images, respectively, for sponges soaked in vancomycin against *Staphylococcus aureus*. The measured radial ZOI is listed under each image in millimeters.

FIG. 4A shows results with *Psuedomonas aeruginosa*. Values listed in 6-post and 48-pre are percentages of the original 6-hour pre-irrigation and debridement levels listed in the first column labeled 6-pre. (values given are mean±standard error of the mean; n=5). FIG. 4B is a graphical representation of bacterial cell quantity (*Staphylococcus aureus*) in a goat open tibial fracture model. Values listed in 6-post and 48-pre are percentages of the original 6-hour pre-irrigation and debridement levels listed in the first column labeled 6-pre. (values given are mean±standard error of the mean; n=5 for No Tx group, n=4 for sponge Tx group) FIG. 4C shows results with *Pseudomonas aeruginosa* and FIG. 4D shows results with *Staphylococcus aureus* are graphs showing bacterial cell quantity (in a goat open tibial fracture model in control and amikacin or vancomycin treatment groups. Values listed are percentages of the original 6-hour pre-irrigation and debridement levels listed in the first column labeled 6-pre. (values given are mean±standard error of the mean; n=5 for No Tx group, n=4 for sponge Tx group) or are cell counts. (values given are mean±standard error of the mean; n=5). In each of FIGS. 4A-4D, 48 hr-pre means 48 hours post inoculation and 42 hours post treatment.

FIG. 5A shows bacterial levels 6 hour post-injury, post-inoculation, pre-irrigation and debridement. (goat 840—SP Tx) for *Staphylococcus aureus*. FIG. 5B shows 6 hour post-injury, post-inoculation, post-irrigation and debridement. Pre-sponge Tx (goat 840—SP Tx) for *Staphylococcus aureus*. A comparison of FIGS. 5A and 5B show 74% bacteria reduction (S.a.) 48 hour post-injury, post-inoculation, post-irrigation and debridement. (goat 94—No Tx) [*Staphylococcus aureus*]. FIG. 5C shows 48 hour post-injury, post-inoculation, post-irrigation and debridement. 42 hr sponge Tx (goat 840—SP Tx) [*Staphylococcus aureus*]. FIG. 5D shows 48 hour post-injury, post-inoculation, post-irrigation and debridement. (goat 94—No Tx) [*Staphylococcus aureus*. A comparison of In FIG. 5C the bacteria count observed after treatment with an antibiotic-loaded chitosan sponge (S.a.) is 0%. In contrast, FIG. 5D shows 357% bacteria count rebound with no treatment (S.a.).

FIG. 14A shows lysozyme-mediated degradation of a film in situ loaded with daptomycin. FIG. 14B shows lysozyme-mediated degradation of a film in situ loaded with vancomycin. Each of these is represented as the average±standard deviation (*p=0.0243; **, p=0.0300; †, p=0.0133; ††, p<0.0001). At 80 hours and on, 71% and 80% DDA films showed a significant decrease in degradation rate. n=5 measurements for all groups.

FIG. 15A shows antibiotic activity of daptomycin elution samples. FIG. 15B shows antibiotic activity of vancomycin elution samples. Activity is indicated by the percent inhibition of *S. aureus* growth and represented as the average±standard deviation. All variation samples over 72 hrs had nearly complete inhibition. n=3 measurements for all groups.

DETAILED DESCRIPTION OF THE INVENTION

Figure 1A:
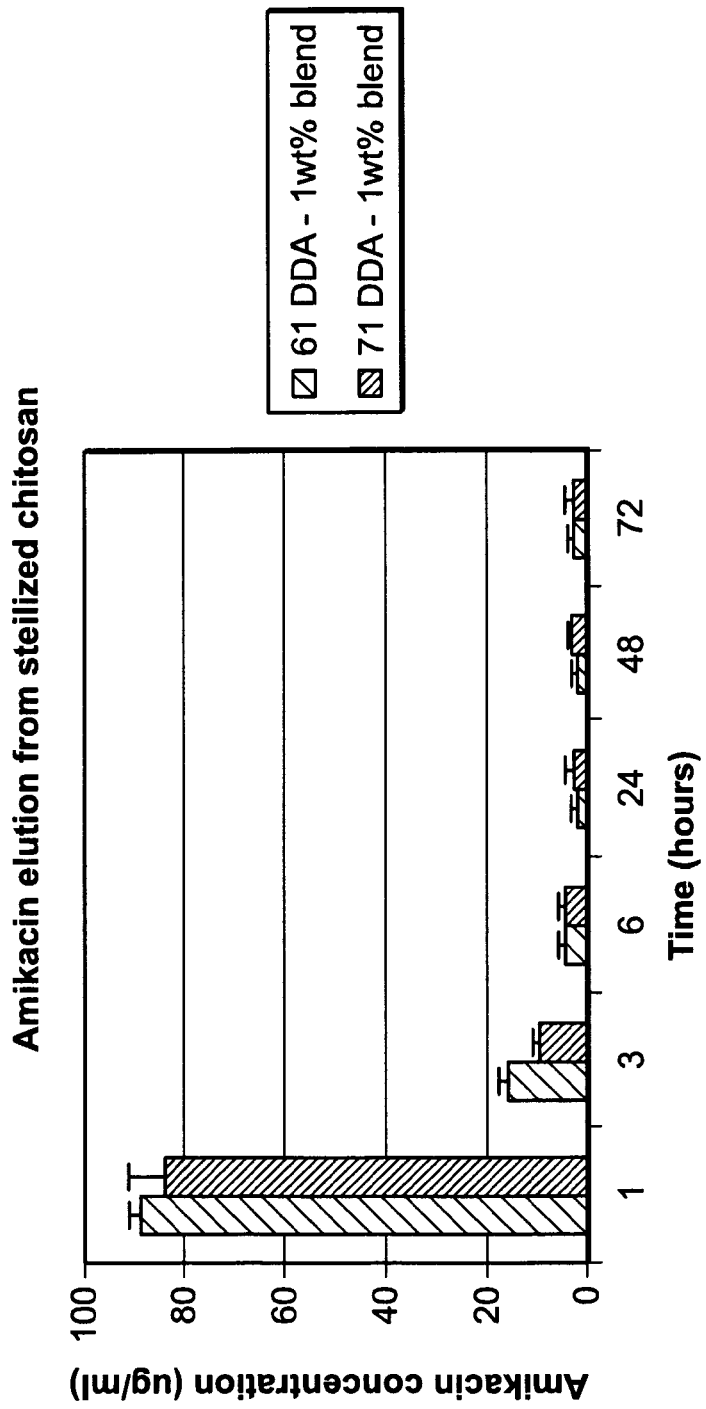
FIGS. 1A-1C are graphs showing antibiotic (amikacin/vancomycin) elution from sterilized chitosan.

As described below, the present invention features chitosan compositions (e.g., solids, sponges, films, hydrogels, composites) that provide for the local delivery of biologically active agents and methods of using such compositions to treat or prevent an infection or promote healing.

The invention is based, at least in part, on the discovery that acid-treated chitosan can form wound management devices whose degradation and drug elution properties can be customized to suit the needs of specific subjects.

Chitosan

Chitosan is a naturally occurring linear polysaccharide composed of randomly distributed β-(1-4)-2-amino-2-D-glucosamine (deacetylated) and β-(1-4)-2-acetamido-2-D-glucoseamine (acetylated) units (FIG. 15). Chitosan is derived from chitin, a naturally occurring polymer. Chitin is a white, hard, inelastic, nitrogenous polysaccharide isolated from fungi, mollusks, or from the exoskeletons of arthropods (e.g., crustaceans, insects). The major procedure for obtaining chitosan is the alkaline deacetylation of chitin with strong alkaline solution. Generally, the raw material is crushed, washed with water or detergent, and ground into small pieces. After grinding, the raw material is treated with alkali and acid to isolate the polymer from the raw crushed material. The polymer is then deacetylated by treatment with alkali. Chitin and chitosan differ in their degrees of deacetylation (DDA). Chitin has a degree of deacetylation of 0% while pure chitosan has a degree of deacetylation of 100%. Typically, when the degree of deacetylation is greater than about 50% the polymer is referred to as chitosan.

Chitosan is a cationic weak base that is substantially insoluble in water and organic solvents. Typically, chitosan is fairly soluble in dilute acid solutions, such as acetic, citric, oxalic, proprionic, ascorbic, hydrochloric, formic, and lactic acids, as well as other organic and inorganic acids. Chitosan's charge gives it bioadhesive properties that allow it to bind to negatively charged surfaces, such as biological tissues present at a site of trauma or negatively charged implanted devices. Chitosan's degree of deacetylation affects it resorption. Chitosan compositions having a 50% degree of deacetylation are highly degradable in vivo. As the degree of deacetylation increases, chitosan becomes increasingly resistant to degradation. Chitosan compositions having a degree of deacetylation that is higher than 95% degrade slowly over weeks or months. In the body chitosan is degraded by lysozyme, N-acetyl-o-glucosaminidase and lipases. Lysozyme degrades chitosan by cleaving the glycosidic bonds between the repeating chitosan units. The byproducts of chitosan degradation are saccharides and glucosamines that are gradually absorbed by the human body. Therefore, when chitosan is used for the local delivery of therapeutic or prophylactic agents, no secondary removal operation is required.

As reported herein, chitosan compositions (e.g., solids, sponges, films, hydrogels, composites) can be loaded with a biologically active agent at the site of care (e.g., in a surgical suite, clinic, or physician's office, trauma site, battlefield). This property allows the clinician to tailor the antibiotics or other agents used to load the chitosan wound management device to suit the needs of a particular patient. In one embodiment, the degree of deacetylation is adjusted to provide chitosan compositions that degrade in as little as about twenty-four, thirty-six, forty-eight, or seventy two hours or that are maintained for a longer period of time (e.g., 4, 5, 6, 7, 8, 9, 10 days). In other embodiments, chitosan compositions of the invention are maintained in the body for at least about two-six weeks or more (e.g., 2, 3, 4, 5, 6 weeks, two, three or four months). In still other embodiments, chitosan compositions of the invention enhance blood clotting in a wound or other site of trauma (hemostasis). In other embodiments, the chitosan compositions are loaded with therapeutic or prophylactic agents that are clinician selected and that are delivered over at least about 1, 2, 3, 4, 5, 6, 7, 8, 9, or 10 days or for longer periods.

Antimicrobial Agents

*Staphylococcus aureus, staphylococcus epidermidis*, and *Pseudomonas aeruginosa* are pathogens that are commonly present at musculoskeletal wound sites. *S. aureus* is one cause of osteomyelitis and nongonococcal bacterial arthritis, and is often associated with prosthetic joint infection. The invention provides chitosan compositions useful in treating or preventing infection in a wound, complex wound, open fraction, or other site of trauma. Any antimicrobial agent known in the art can be used in the chitosan compositions of the invention at concentrations generally used for such agents.

Antimicrobial agents useful in chitosan compositions of the invention include but are not limited to antibacterials, antifungals, and antivirals. An antimicrobial agent as used herein is an agent which reduces or stabilizes the survival, growth, or proliferation of a pathogen. Antimicrobial agents include but are not limited to Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefinetazole; Cefinetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride, Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin lydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacil; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz: Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium: Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride. In particular embodiments, a chitosan composition comprises daptomycin.

In one preferred embodiment, a chitosan composition of the invention comprises an agent that treats a multidrug resistant bacteria. In one approach, linezolid may be used to treat multi-drug resistant Gram positive bacteria. Linezolid is commercially available under the trade name Zyvox (Pfizer).

In other embodiments, a chitosan composition comprises one or more of the following: Benzalkonium Chloride, Cetylpyridinium Chloride, and Chlorhexidine Digluconate. In still other embodiments, a chitosan composition comprises one or more of antimicrobials: Polyhexamethylene Biguanide, Octenidine Dihydrochloride, Mild Silver Protein, Povidone Iodine (solution or ointment), Silver Nitrate, Silver Sulfadiazine, Triclosan, Cetalkonium Chloride, Myristalkonium Chloride, Tigecycline, Lactoferrin, Quinupristin/dalfopristin, Linezolid, Dalbavancin, Doripenem, Imipenem, Meropenem, and Iclaprim.

In still other embodiments, the chitosan composition comprises an essential oil having antimicrobial properties. Exemplary essential oils include Oregano oil, tea tree oil, mint oil, sandalwood oil, clove oil, nigella sativa oil, onion oil, leleshwa oil, lavender oil, lemon oil, lemon myrtle oil, neem oil, garlic, eucalyptus oil, peppermint oil, cinnamon oil, and thyme oil.

In still other embodiments, the antimicrobial is a fatty acid (e.g., Cis-2-Decenoic Acid).

Antivirals are agents capable of inhibiting the replication of viruses. Examples of anti-viral agents include but are not limited to 1,-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Antifungal agents useful in chitosan compositions of the invention include fungicidal and fungistatic agents such as, for example, benzoic acid, undecylenic alkanolamide, ciclopirox olamine, polyenes, imidazoles, allylamine, thicarbamates, amphotericin B, butylparaben, clindamycin, econaxole, fluconazole, flucytosine, griseofulvin, nystatin, and ketoconazole. In one preferred embodiment, the antifungal is amphotericin.

In one embodiment, the invention provides chitosan compositions comprising a combination of one or more antimicrobials and antivirals or antifungals.

Growth Factors

Growth factors are typically polypeptides or fragments thereof that support the survival, growth, or differentiation of a cell. Such agents may be used to promote wound healing. A chitosan composition described herein can be used to deliver virtually any growth factor known in the art. Such growth factors include but are not limited to angiopoietin, acidic fibroblast growth factors (aFGF) (GenBank Accession No. NP_149127) and basic FGF (GenBank Accession No. AAA52448), bone morphogenic protein (BMP) (GenBank Accession No. BAD92827), vascular endothelial growth factor (VEGF) (GenBank Accession No. AAA35789 or NP_001020539), epidermal growth factor (EGF) (GenBank Accession No. NP_001954), transforming growth factor cc (TGF-α) (GenBank Accession No. NP_003227) and transforming growth factor β (TFG-β) (GenBank Accession No. 1109243A), platelet-derived endothelial cell growth factor (PD-ECGF) (GenBank Accession No. NP_001944), platelet-derived growth factor (PDGF) (GenBank Accession No. 1109245A), tumor necrosis factor cc (TNF-α) (GenBank Accession No. CAA26669), hepatocyte growth factor (HGF) (GenBank Accession No. BAA14348), insulin like growth factor (IGF) (GenBank Accession No. P08833), erythropoietin (GenBank Accession No. P01588), colony stimulating factor (CSF), macrophage-CSF (M-CSF) (GenBank Accession No. AAB59527), granulocyte/macrophage CSF (GM-CSF) (GenBank Accession No. NP_000749) and nitric oxide synthase (NOS) (GenBank Accession No. AAA36365). In one preferred embodiment, the growth factor is BMP.

Analgesics

Chitosan compositions of the invention can be used for the delivery of one or more agents that ameliorate pain, such agents include but are not limited to opioid analgesics (e.g. morphine, hydromorphone, oxymorphone, levorphanol, levallorphan, methadone, meperidine, fentanyl, codeine, dihydrocodeine, oxycodone, hydrocodone, propoxyphene, nalmefene, nalorphine, naloxone, naltrexone, buprenorphine, butorphanol, nalbuphine or pentazocine; a nonsteroidal anti-inflammatory drug (NSAID) (e.g., aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, or a pharmaceutically acceptable salt thereof; a barbiturate sedative, e.g. amobarbital, aprobarbital, butabarbital, butabital, mephobarbital, metharbital, methohexital, pentobarbital, phenobartital, secobarbital, talbutal, theamylal or thiopental or a pharmaceutically acceptable salt thereof; a COX-2 inhibitor (e.g. celecoxib, rofecoxib or valdecoxib.

Anti-Thrombotic

Chitosan compositions of the invention are also useful for inhibiting, reducing or ameliorating clot formation. In one embodiment, a chitosan composition contains one or more anti-thrombotids (e.g., thrombin, fibrinogen, cumidin, heparin).

Anti-Inflammatories

In other embodiments, a chitosan composition is used to deliver an anti-inflammatory agent. Such anti-inflammatory agents include, but are not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; and Zomepirac Sodium.

Delivery of Agents Via Chitosan Compositions

The invention provides a simple means for delivering biologically active agents (e.g., small compounds, nucleic acid molecules, polypeptides) using a chitosan composition. The chitosan composition is delivered to a subject and the biologically active agent is eluted from the composition in situ. The chitosan composition is capable of delivering a therapeutic for the treatment of a disease or disorder that requires controlled and/or localized drug delivery over some period of time (e.g., 1, 3, 5, 7 days; 2, 3, 4 weeks; 1, 2, 3, 6, 12 months). Desirably, the chitosan composition comprises an effective amount of one or more antibiotics (e.g., amikacin, daptomycin, vancomycin), growth factors that promote wound healing, small molecules, hemostatic agents (e.g., thrombin and/or fibrinogen), anti-thrombotics (e.g., heparin), or cartilage or bone repair agents. The chitosan composition are administered in the form of solids, sponges, films, hydrogels, or composites (e.g., sponge fragments in a hydrogel matrix).

Preferably, the chitosan composition comprises at least about 1 µg, 25 µg, 50 µg, 100 µg, 250 µg, 500 µg, 750 µg, 1 mg, 5 mg, 10 mg, 25 mg, 50 mg, 75 mg, 100 mg, 200 mg, 250 mg, 300 mg, 400 mg, or 500 mg of an agent (e.g., an antibiotic). In another embodiment, the composition releases at least about 1 µg, 25 µg, 50 µg, 100 µg, 250 µg, 500 µg, 750 µg, 1 mg, 5 mg, 10 mg, 25 mg, 50 mg, 75 mg, 100 mg, 200 mg, 250 mg, 300 mg, 400 mg, or 500 mg of an agent (e.g., an antibiotic) over the course of at least about 1, 2, 3, 4, 5, 6, 7, 8, 9, 10, 14, 21, 28, or 35 days. In still another embodiment, the composition comprises at least about 1 µg, 25 µg, 50 µg, 100 µg, 250 µg, 500 µg, 750 µg, 1 mg, 5 mg, 10 mg, 25 mg, 50 mg, 75 mg, 100 mg, 200 mg, 250 mg, 300 mg, 400 mg, or 500 mg of an agent (e.g., an antibiotic) per $cm^3$.

Chitosan Coatings

A chitosan composition may be included in a coating material, such as a film, that is used to coat or wrap a medical device (e.g., drug delivery or other medical device). Such coatings are used, for example, for treating or preventing a pathogen infection or for drug delivery. In orthopaedics, many post-surgical infections are associated with implant materials. Patients receiving an orthopedic implants have an infection risk of about 5% for total joint replacements. Bacteria are passively adsorbed on biomaterial surfaces after implantation. The fundamental pathogenic mechanism in biomaterial-centered sepsis is microbial colonization of the biomaterials followed by adjacent damaged tissues. Patients that suffer from such infections often require the removal and replacement of the implant to eradicate the infection.

To treat or prevent an implant-associated infection a chitosan composition of the invention is applied to the medical device (e.g., implant). The chitosan composition provides for release of a therapeutic or prophylactic agent from the device. Such agents advantageously reduce the risk of infection associated with conventional implants. Such coatings can be applied to any medical device known in the art, including, but not limited to orthopedic devices (e.g., for joint implants, fracture repairs, spinal implants, screws, rods, plates); surgical devices (e.g., sutures, staples, anastomosis devices, vertebral disks, bone pins, suture anchors, hemostatic barriers, clamps, screws, plates, clips, vascular implants, tissue adhesives and sealants, tissue scaffolds); wound management devices; drug-delivering vascular stents (e.g., a balloon-expanded stents); other vascular devices (e.g., grafts, catheters, valves, artificial hearts, heart assist devices); implantable defibrillators; blood oxygenator devices (e.g., tubing, membranes); membranes; biosensors; shunts for hydrocephalus; endoscopic devices; infection control devices; dental devices (e.g., dental implants, fracture repair devices), urological devices (e.g., penile, sphincter, urethral, bladder and renal devices, and catheters); colostomy bag attachment devices; ophthalmic devices (e.g. intraocular coils/screws); glaucoma drain shunts; synthetic prostheses (e.g., breast); intraocular lenses; respiratory, peripheral cardiovascular, spinal, neurological, dental, ear/nose/throat (e.g., ear drainage tubes); renal devices; and dialysis (e.g., tubing, membranes, grafts), urinary catheters, intravenous catheters, small diameter grafts, vascular grafts, artificial lung catheters, atrial septal defect closures, electro-stimulation leads for cardiac rhythm management (e.g., pacer leads), glucose sensors (long-term and short-term), degradable coronary stents (e.g., degradable, non-degradable, peripheral), blood pressure and stent graft catheters, birth control devices, prostate cancer implants, bone repair/augmentation devices, breast implants, cartilage repair devices, dental implants, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, hemodialysis devices, catheter cuff, anastomotic closures, vascular access catheters, cardiac sensors, uterine bleeding patches, urological catheters/stents/implants, in vitro diagnostics, aneurysm exclusion devices, and neuropatches.

Examples of other suitable devices include, but are not limited to, vena cava filters, urinary dialators, endoscopic surgical tissue extractors, atherectomy catheters, clot extraction catheters, coronary guidewires, drug infusion catheters, esophageal stents, circulatory support systems, angiographic catheters, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

It is noted that in other embodiments of the present invention, the chitosan composition of the present invention may self adhere to the medical device or may be adhered to the device by means other than coating materials, such as adhesives, sutures, or compression. Any suitable method know in the art may be utilized to adhere the chitosan composition to a surface. For example, the chitosan composition may be adhered to the surface by pressing the chitosan composition onto the device, wrapping the device with a chitosan film, or spraying a chitosan composition onto the device.

The chitosan compositions with biocompatible surfaces may be utilized for various medical applications including, but not limited to, drug delivery devices for the controlled release of pharmacologically active agents, including wound healing devices, such as hemostatic sponges, dressings, suture material and meshes, medical device coatings/films and other biocompatible implants.

Chitosan Fibers

Randomly oriented fibrous mats can be made from chitosan by electrospinning (Schiffman and Schauer, Biomacromolecules, 2007. 8(9): p. 2665-7). These fibers are typically a mean diameter of 100 nm, but the diameter of the fibers can vary widely depending upon a number of factors. Some fibers can be as large as 1 μm in diameter, and as small as 28 nm. Typically, fibrous mats have a mean diameter between 100-200 nm.

In one approach, about 7-9 wt % chitosan is dissolved in 99-100% trifluoroacetic acid. The solvent solution contains about 0-30% methylene chloride to aid in spinnability. The solution is gently mixed for 24 hours. At this point additives such as drugs, proteins, calcium phosphate salts, or other biologically active constituents can be added. The solution is loaded into a plastic 10 mL syringe. In one embodiment, a blunt 21 gauge (G) metal needle is used. In other embodiments, needle sizes range from about 16-23G. The syringe is loaded into a syringe pump and the flowrate is set for 20-30 μL/min (usually 20 μL/min). The needle is connected to the positive electrode of the power source, while the target is connected to the ground. The target can consist of a copper plate wrapped in aluminum foil, an aluminum SEM stub, or any other conductive surface. The voltage is set between 15-26 kV. The distance between the tip and the target is between about 12-25 cm. In one preferred embodiment, 15-16 cm is used. Typically, the apparatus is used inside a ventilated box within fume hood. The box protects the fibers from air currents as they are deposited on the target. Once deposited, the fiber mat can be removed from the surface and treated as follows. Typically, the fiber mat is maintained under vacuum for about 24 hours, and then the fiber mat is neutralized in 5M $Na_2CO_3$. After drying, mats are cut to any desired size and sterilized. Another method to electrospin chitosan involves using 1,1,1,3,3,3-Hexafluoroisopropanol (HFIP) as a solvent (Shin et al., J Periodontol, 2005. 76(10): p. 1778-84). One advantage is that there is no need to neutralize the mat. The residual solvent is pulled off in vacuum. HFIP solvent can also be used with methylene chloride to aid in spinning. Other methods for generating chitosan fibers are described, for example, by Sangsanoh and Supaphol, Biomacromolecules, 2006. 7(10): p. 2710-4 or Schiffman and Schauer, Biomacromolecules, 2007. 8(2): p. 594-601.

Wound Healing Devices

The present invention provides wound healing devices that employ a chitosan composition. The wound healing devices may be configured by forming the chitosan composition into a shape and size sufficient to accommodate the wound being treated. If desired, the wound healing device comprises chitosan fibers. Wound healing devices are desirably produced in whatever shape and size is necessary to provide optimum treatment to the wound. These devices can be produced in forms that include, but are not limited to, plugs, meshes, strips, sutures, dressings, or any other form able to accommodate and assist in the repair of a wound. The damaged portions of the patient that may be treated with devices made of the chitosan composition of the present invention include, but are not limited to, bone, cartilage, skin, muscle and other tissues (nerve, brain, spinal cord, heart, lung). Other similar devices are administered to assist in the treatment repair and remodeling of a damaged tissue, bone, or cartilage. For some applications, it is desirable for the device to be incorporated into an existing tissue to facilitate wound repair. For other applications, it is desirable for the device to degrade over the course of days, weeks, or months. Such degradation may be advantageously tailored to suit the needs of a particular subject using the methods described herein. The elution and/or degradation profile of a chitosan composition (e.g., film, sponge) can be altered as described herein by modulating the following variables: degree of deacetylation, neutralization solution, solvent make-up, and chitosan weight %, and/or crystallinity.

Crystallinity indicates the degree of structural order in a compound. Polymers such as chitosan are either amorphous or semicrystalline. Chitosan's crystallinity, like other polymers, depends on its type, number, and regularity of polymer-chain, side group chemistry, the degree of matrix packing or density, and crosslinking. The crystallinity of chitosan or its products can be controlled or altered during manufacture through its molecular weight, degree of deacetylation, and crosslinking to affect thermal properties, such as melting point, and physical-mechanical properties, such as tensile strength, Young's modulus, swelling and degradation.

Crosslinking is the process which links polymer chains together. In chitosan, crosslinking induces a three-dimensional matrix of interconnected, linear, polymeric chains. The degree or extent of crosslinking depends on the crosslinking agent. Exemplary crosslinking agents include sodium tripolyphosphate, ethylene glycol diglycidyl ether, ethylene oxide, glutaraldehyde, epichlorohydrin, diisocyanate, and genipin. Crosslinking can also be accomplished using microwave or ultraviolet exposure.

Chitosan's properties can also be altered by modulating the degree of deacetylation. In one embodiment, the degree of deacetylation is adjusted between about 50-100%, wherein the bottom of the range is any integer between 50 and 99, and the top of the range is any integer between 51% and 100%. In particular embodiments, the degree of deacetylation is 51%, 55%, 60%, 61%, 65%, 70%, 71%, 73%, 74%, 75%, 76%, 77%, 78%, 79%, 80%, 85%, 90%, and 95%. In general, the higher the molecular weight, the slower the degradation of the chitosan composition.

If desired, chitosan is neutralized after acid treatment. Any base known in the art (e.g., NaOH, KOH, $NH_4OH$, $Ca(OH)_2$, $Mg(OH)_2$, or combinations thereof) may be used to neutralize an acid-treated chitosan composition. Preferably, a neutralization solution has a pH greater than 7.4 (e.g., 7.8, 8.0, 8.5, 9.0, 10, 11, and 12, 13, 14, 15, 16). The neutralization step is optional, and not strictly required. If desired, the chitosan is treated with water, PBS, or sterile saline following acid treatment. It may comprise 0.01-10.0M of a base (e.g., 0.01, 0.025, 0.5, 0.75, 0.1, 0.25, 0.5, 0.75, 1.0, 1.5, 2.0, 2.5, 3, 4, 5, 6, 7, 8, 9, 10 M) (e.g., NaOH). Chitosan compositions neutralized in bases having lower molarity degrade more quickly.

Chitosan compositions neutralized in bases of increased molarity degrade more slowly than those neutralized at lesser molarities. Thus, the degradation properties of chitosan can be modulated by altering the molarity of the neutralizing base.

In other embodiments, the concentration of the acidic solvent used to dissolve the chitosan is adjusted or the time period used to dissolve the chitosan is altered. For example, a 0.1%, 0.5%, 1%, 2%, 3% or 5% acid solution is used. In particular embodiments, chitosan is dissolved in acetic, citric, oxalic, proprionic, ascorbic, hydrochloric, formic, salicylic and/or lactic acids, or a combination of those. In general, acidic solvents comprising increased levels of lactic acid form chitosan compositions that degrade more quickly and also have reduced strength and durability. In various embodiments, a combination of acetic and lactic acids are used. Acetic provides more strength and slower degradation. In contrast, lactic acid provides more flexibility. In one approach, the ratio of lactic to acetic acid is varied from 5:1, 4:1, 3:1, 2:1, 1:1, 1:2, 1:3, 1:4, to 1:5. In one embodiment, the blended acid solvent comprises 90%/10%, 80%/20% 75%/25%, 70%/30%, 60%/40%, 50%/50%. In still other embodiments, the chitosan weight % is altered from 0.25-10.0% (e.g., 0.1, 0.2, 0.25, 0.3, 0.4, 0.5, 1, 1.25, 1.5, 1.75, 2.0, 2.5, 3.0, 3.5, 4, 5, 6, 7, 8, 9, 10%). In one embodiment, a 1 wt % chitosan solution is preferred, where a 1 wt % chitosan solution contains 1 gram of chitosan per 100 ml solution. Typically, the higher the wt %, the slower the degradation.

If desired the chitosan composition is loaded with agents and the chitosan composition is delivered to a wound to form a delivery system for the agent. Preferably, the chitosan composition contains an effective amount of a chemical or pharmaceutically active component. In one embodiment, the chitosan composition self-adheres to a site at which delivery is desired. In another embodiment, an adhesive or other adhering means may be applied to the outer edges of the chitosan composition to hold the composition in position during the delivery of the chemical or pharmaceutically active component. Such adherent means may be used alone or in combination with the self-adhering properties of chitosan. Chitosan compositions provide for the local administration of a desired amount of a therapeutic agent.

Other embodiments of the present invention include wound-healing devices configured and produced as biological fasteners, such as threads, sutures and woven sheets. Threads and sutures comprising various embodiments of the chitosan composition provide a biocompatible fastening and suturing function for temporarily treating and sealing an open wound. Additionally, the biological fasteners may include pharmacologically active agents that may assist in the healing and remodeling of the tissue within and around the wound. Advantageously, such fastening and suturing devices may be treated to degrade in vivo at a desired rate. In other embodiments, the chitosan composition is administered directly to an injured area. A chitosan composition of the invention is administered by sprinkling, packing, implanting, inserting or applying or by any other administration means to a site of trauma (e.g., open wound, open fracture, complex wound).

Hemostatic Chitosan Compositions

The invention further provides chitosan compositions in the form of a hemostatic matrix (e.g., hemostatic sponges). Such compositions are useful alone or may be used for the delivery of a therapeutic or prophylactic agent delineated herein. Such matrices generally comprise porous compositions formed from chitosan. In general, sponges can be formed by providing a liquid solution of chitosan capable of forming a porous three-dimensionally stable structure. In one embodiment, a chitosan solution is prepared by dissolving deacetylated chitosan in an acidic solvent. A sponge is formed by casting the solution in a mold to achieve a desired shape. The chitosan solution is then frozen and lyophilized, thereby forming a chitosan sponge. Lyophilization is conducted to reduce the liquid (e.g. water) content of the matrix to less than about 5%, 10%, 20%, 25%, 30%, 40%, 50%, 75%, 80%, 90%, 95%, or 100% by weight. If desired, a second lyophilization step is carried out. This step is strictly optional. Following one or more lyophilizations, the chitosan composition may still include some amount of water. Typically, lypholization removes at least about 70%, 75%, 80%, 90%, 95, or 100% or the original water content of the chitosan composition. Chitosan compositions that retain some moisture may be packaged in sterile foil to maintain such moisture.

In one approach, the sponge is neutralized, for example, by treatment with a basic solution, re-lyophilized. The sponge matrix is stabilized structurally and remains in a highly dense and compacted state until contacted with a liquid susceptible to absorption by the matrix, for example, body fluids. For medical use, the compacted or compressed sponge is sterilized using any suitable means (e.g., radiation). The device is packaged in sterile packaging for medical use. Sponge elements or other devices of the invention may also contain one or more active therapeutic agents. For example, they include agents that promote clotting (e.g., thrombin and/or fibrinogen). Alternatively or in addition, sponge elements or other devices of the invention include antibiotics and/or growth factors that promote tissue growth and healing.

A chitosan composition is incubated with a therapeutic agent such that the agent is incorporated into the chitosan. This incubation is typically carried out before or during a procedure to treat a subject using methods described herein. Sponge materials of the invention will advantageously be expandable when wetted. Preferably, the sponge has the capacity to expand at least about 10%-100% (10, 20, 30, 40, 50). In other embodiments, a sponge expands by about 200% by volume when wetted to saturation with deionized water, buffer, or an agent of the invention. Preferred sponge materials achieve rapid volume expansions (e.g., when immersed in aqueous solution). Hemostatic sponges are produced in any size required for application to a wound. In one embodiment, the expanded sponge exerts compression on surrounding tissues when implanted or delivers an active agent to the implantation site and surrounding tissue.

Delivery of Chitosan Compositions

Chitosan compositions can be delivered by any method known to the skilled artisan. In one approach, a chitosan composition is locally delivered to a site of trauma in the form of a film or sponge. The film, sponge, or other wound management device can be configured to fit a wound of virtually any size. In another approach, the chitosan composition is surgically implanted at a site where promotion of healing and/or treatment or prevention of infection is required. If desired, the chitosan composition is loaded with one or more antibiotics or other biologically active agents by a clinician within the surgical suite where treatment is to be provided. This advantageously allows the chitosan composition to be loaded with a specific agent or combination of agents tailored to the needs of a particular patient at the point at which care is to be provided.

Screening Assays

As described herein, the present invention provides for the delivery of therapeutic or prophylactic agents to wounds in vivo. The invention is based in part on the discovery that therapeutic agents can be delivered using a chitosan composition where the agents and degradation of the composition is tailored to suit the needs of a particular patient. To identify chitosan compositions having the desired degradation and elution profiles, screening may be carried out using no more than routine methods known in the art and described herein. For example, chitosan compositions are loaded with one or more therapeutic agents and such compositions are subsequently compared to untreated control compositions to identify chitosan compositions that promote healing. In another embodiment, the degradation of a chitosan composition of the invention is assayed in vivo to identify the degree of deacetylation that corresponds to a the desired degradation profile. Any number of methods are available for carrying out screening assays to identify such compositions.

In one working example, candidate compounds are added at varying concentrations to a chitosan composition. The degree of infection or wound healing is then measured using standard methods as described herein. The degree of infection (e.g., number of bacteria) or wound healing in the presence of the compound is compared to the level measured in a control lacking the compound. A compound that enhances healing is considered useful in the invention; such a compound may be used, for example, as a therapeutic to prevent, delay, ameliorate, stabilize, or treat a disease described herein (e.g., tissue damage). In other embodiments, the compound prevents, delays, ameliorates, stabilizes, or treats a disease or disorder described herein. Such therapeutic compounds are useful in vivo.

In another approach, chitosan compositions having varying degrees of deacetylation are incubated in vivo, added to a wound, or are contacted with a composition comprising an enzyme having chitosan-degrading activity. The length of time required for chitosan degradation is then measured using standard methods as described herein. A chitosan composition having the desired degradation profile (e.g., degrading in 3 days, 5 days, 1 week, 2 weeks, 3 weeks, 1 month, 2 months, 3 months) is considered useful in the invention; such a composition may be used, for example, as a therapeutic to prevent, delay, ameliorate, stabilize, or treat a disease described herein (e.g., tissue damage). In other embodiments, the composition prevents, delays, ameliorates, stabilizes, or treats a disease or disorder described herein. Such therapeutic compositions are useful in vivo.

The present invention provides methods of treating pathogen infections (e.g., bacterial, viral, fungal), complex wounds, open fractures, trauma, and associated diseases and/or disorders or symptoms thereof which comprise administering a therapeutically effective amount of a composition comprising chitosan and a therapeutic or prophylactic agent of a formulae herein to a subject (e.g., a mammal, such as a human). Thus, one embodiment is a method of treating a subject suffering from or susceptible to an infection, trauma, wound, open fracture, or related disease or disorder that requires targeting of a therapeutic composition to a site. The method includes the step of administering to the mammal a therapeutic amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for an infection, in need of healing, having a trauma, wound, open fracture, or related disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The agents herein may be also used in the treatment of any other disorders in which it is desirable to promote healing or treat or prevent an infection.

In one embodiment, the invention provides a method of monitoring treatment progress. The method includes the step of determining a level of diagnostic marker (Marker) (e.g., wound healing parameters, number of bacterial cells, or any target delineated herein modulated by a compound herein, C-reactive protein, cytokine levels, or indicator thereof, etc.) or diagnostic measurement (e.g., screen, assay) in a subject suffering from or susceptible to an infection, disorder or symptoms thereof, in which the subject has been administered a therapeutic amount of a chitosan composition (e.g., a chitosan composition comprising a therapeutic or prophylactic agent) herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Test Compounds and Extracts

In general, therapeutic compounds suitable for delivery from a chitosan composition are known in the art or are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is identified as containing a compound of interest, further fractionation of the positive lead extract is necessary to isolate chemical constituents responsible for the observed effect. Thus, the goal of the extraction, fractionation, and purification process is the careful characterization and identification of a chemical entity within the crude extract that achieves a desired biological effect. Methods of fractionation and purification of such heterogenous extracts are known in the art.

Small molecules of the invention preferably have a molecular weight below 2,000 daltons, more preferably between 300 and 1,000 daltons, and most preferably between 400 and 700 daltons. It is preferred that these small molecules are organic molecules.

Kits

The invention provides kits that include chitosan compositions. In one embodiment, the kit includes a chitosan composition containing a therapeutic or prophylactic agent that that prevents or treats infection (e.g., an antimicrobial agent) or that promotes healing (e.g., growth factor, anti-inflammatory, clot promoting agent, anti-thrombotic). In other embodiments, the kit contains a therapeutic device, such as a chitosan film useful in wound healing, chitosan sponge, hydrogel, or implant/prosthetic device comprising a chitosan composition described herein. If desired, the aforementioned chitosan compositions further comprise an agent described herein.

In some embodiments, the kit comprises a sterile container which contains a chitosan composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a chitosan composition of the invention is provided together with instructions for using it in a prophylactic or therapeutic method described herein. The instructions will generally include information about the use of the composition for the treatment of a trauma, infection or related disease in a subject in need thereof. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Antibiotic Delivery by a Chitosan Sponge Inhibited Bacterial Growth

There is a need for a biocompatible, resorbable carrier for use in contaminated extremity injuries that can be custom loaded with therapeutic agents based on the suspected bacterial species in a wound. Non-restrictive loading could potentially reduce bacterial colonization by orders of magnitude and reduce infection rates and loss of functionality in limbs in compromised patients with contaminated wounds. The following results indicate that lyophilized chitosan sponges are useful as a carrier for antibiotics. Such sponges may be used alone or as an adjunctive therapy to standard irrigation and debridement for orthopaedic trauma and other musculoskeletal applications.

A sponge containing 61 and 71% deacetylated (DDA) chitosan was loaded with the antibiotic amikacin. Amikacin release at one hour was found to be 88.7±2.4 µg/ml and 83.7±7.3 µg/ml for the 61 and 71 DDA samples, respectively. Amikacin was evident at 72 hours as the 61 DDA samples released 2.8±1.3 µg/ml and the 71 DDA samples released 2.2±1.9 µg/ml (FIG. 1A). Bacterial growth inhibition of *P. aeruginosa* was found to be 98.7% after one hour and 93.1% after 72 hours.

Figure 1B:
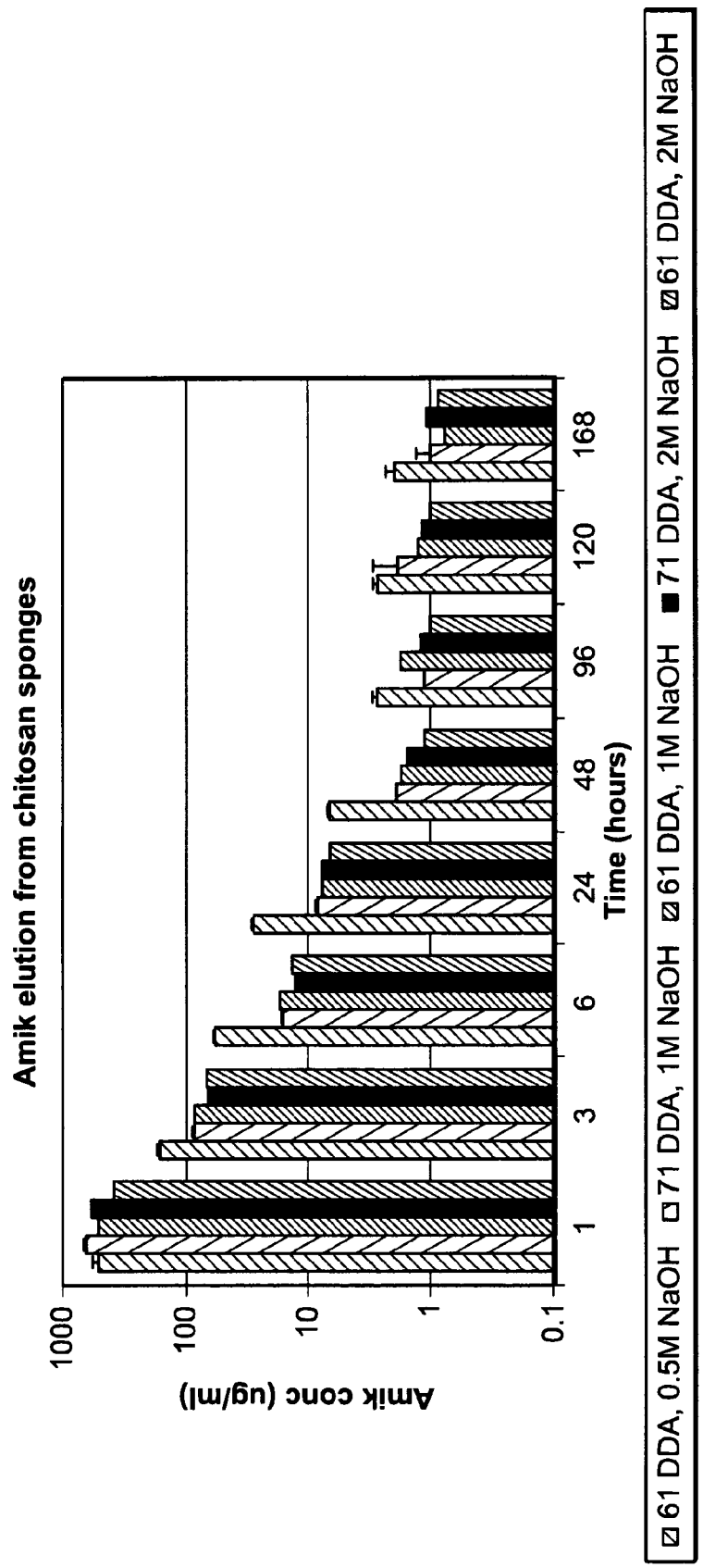
Figure 1C:
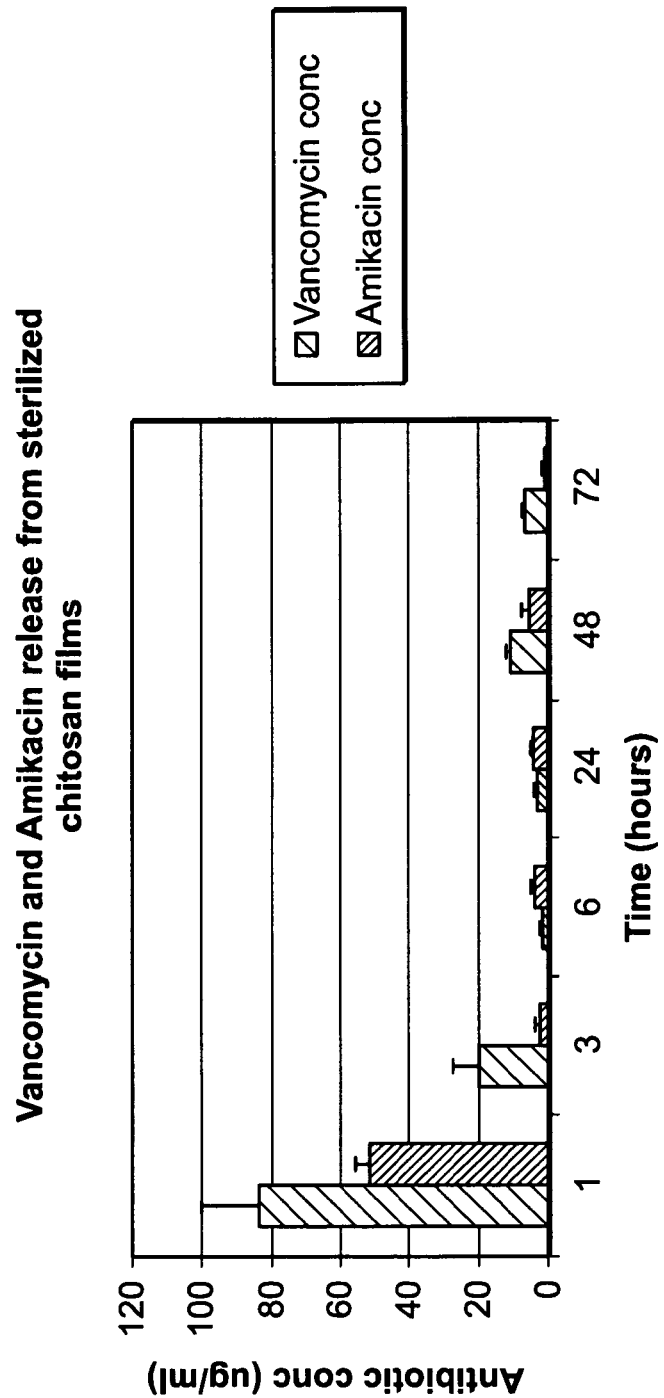

The effect of neutralization conditions on amikacin elution from chitosan sponges was also analyzed (FIG. 1B). In this test, the following chitosan sponges were evaluated: (1) 61 DDA chitosan, 0.5M NaOH neutralized, (2) 71 DDA chitosan 1 M NaOH neutralized, (3) 61 DDA chitosan 1 M NaOH neutralized, (4) 71 DDA chitosan 2 M NaOH neutralized, (5) 61 DDA 2M NaOH neutralized. All sponges were submerged in 5 mg/ml amikacin solution for 2 minutes prior to elution testing. The elution was done in 50 ml of sterile saline solution and completely refreshed at each time point. The elution was carried out for 7 days. The values shown on the graph are in µg/ml. In general, 61DDA chitosan neutralized with 0.5M NaOH provided the best long term release Agent elution from chitosan films was also analyzed (FIG. 1C). Sterilized chitosan films were loaded with amikacin and vancomycin. All films were submerged in 5 mg/ml amikacin or vancomycin solution for 2 minutes prior to elution testing. The elution was done in 50 ml of sterile saline solution and completely refreshed at each time point. The elution was carried out for 3 days. The values shown in FIG. 1C are expressed in µg/ml.

The ability to customize the antibiotic choice is advantageous because it allows clinicians to tailor treatment regimens based on known or suspected bacterial species present. Chitosan sponges allow for larger uptake of antibiotic solution and higher release concentrations than chitosan films. The sponges are also customizable in terms of degradation as manufacturing alterations (e.g., degree of deacetylation, neutralization solution, solvent make-up, and chitosan weight %, and/or crystallinity) can alter degradation rates. The results indicate that incorporation of antibiotics into chitosan provides a local drug delivery system that can be used alone or in conjunction with irrigation and debridement therapies.

Example 2

Chitosan Compositions Comprising Antibiotics that Inhibited Infection In Vivo

Figure 2A:
FIGS. 2A-2C show chitosan sponges.
Figure 2B:
Figure 2C:
Figure 3A:
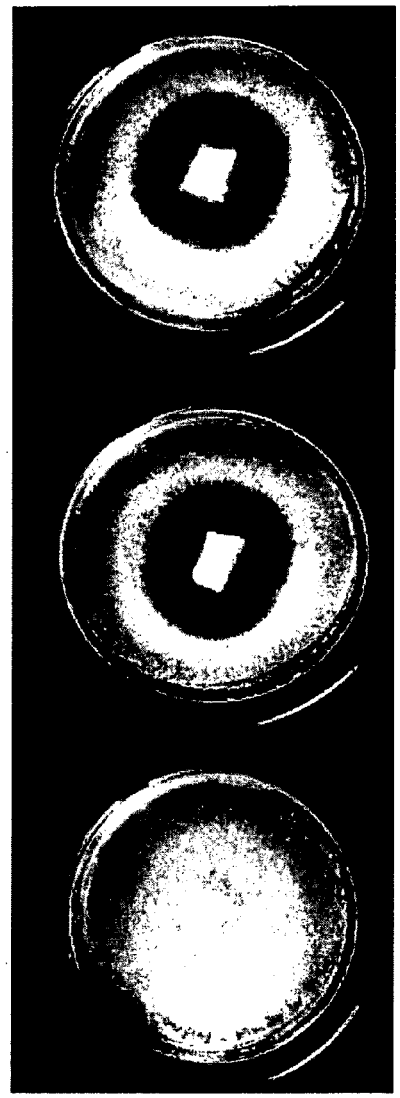
FIGS. 3A-3D show results of Zone of Inhibition (ZOI) studies performed with sterile chitosan sponges. The far-left image of each figure (FIGS. 3A-D) is a sponge soaked in sterile saline and the 2nd and 3rd image in each figure is a sponge soaked in 5 mg/ml antibiotic solution.
Figure 3B:
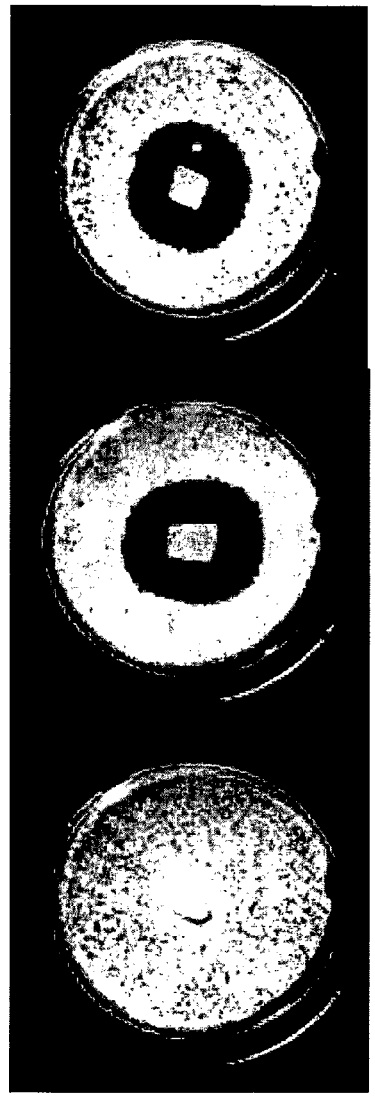
Figure 3C:
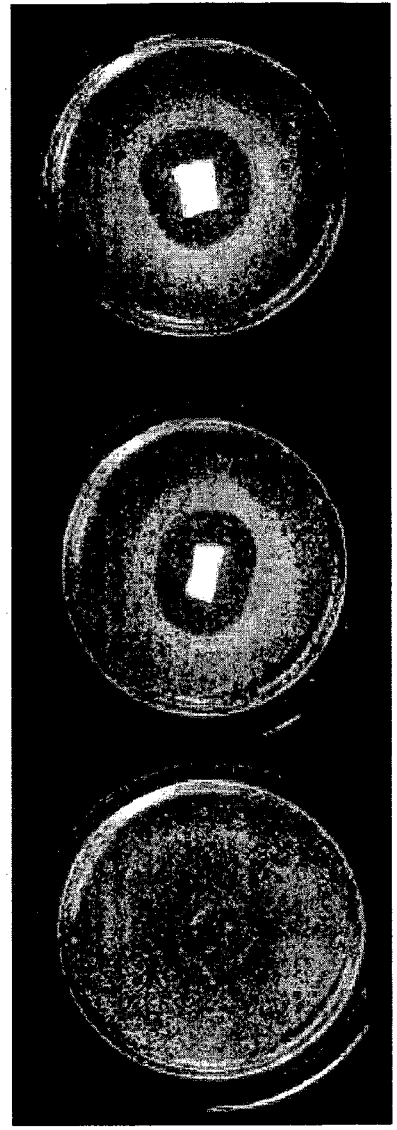
Figure 3D:
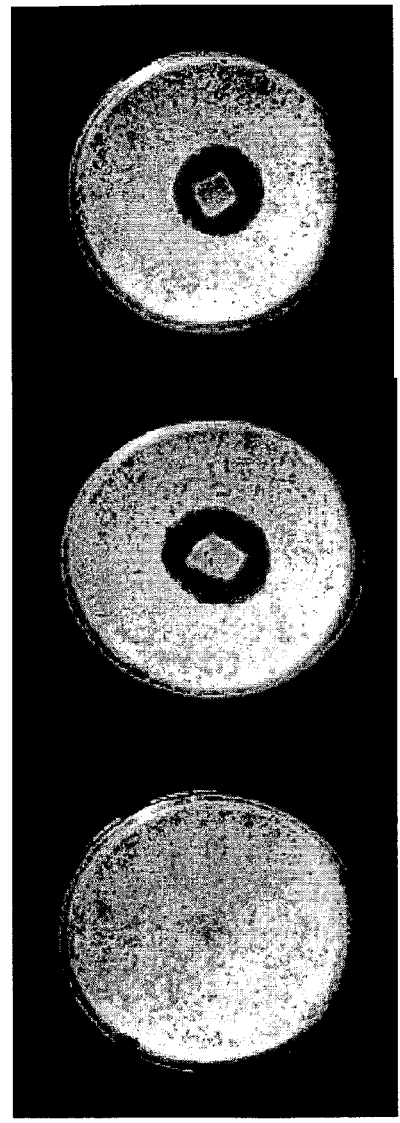

Chitosan sponges (FIGS. 2A-2C) were loaded with antibiotic. The antibiotic elution profile is provided at Table 1.

TABLE 1

Results of the amikacin elution study performed with sterilized chitosan sponges using the finalized methodology in sponge fabrication.

| Sample/Time | 1 hr (µg/ml) | 3 hr (µg/ml) | 6 hr (µg/ml) | 24 hr (µg/ml) | 48 hr (µg/ml) | 72 hr (µg/ml) |
|---|---|---|---|---|---|---|
| 1 | 400 | 400 | 200 | 100 | 100 | 100 |
| 2 | 400 | 400 | 100 | 200 | 100 | 100 |
| 3 | 400 | 400 | 100 | 200 | 100 | 100 |

All values listed are in µg/ml. All samples were drawn from 20 ml of 1 × PBS (complete refreshment of solution was done at each timepoint).

Figure 17:
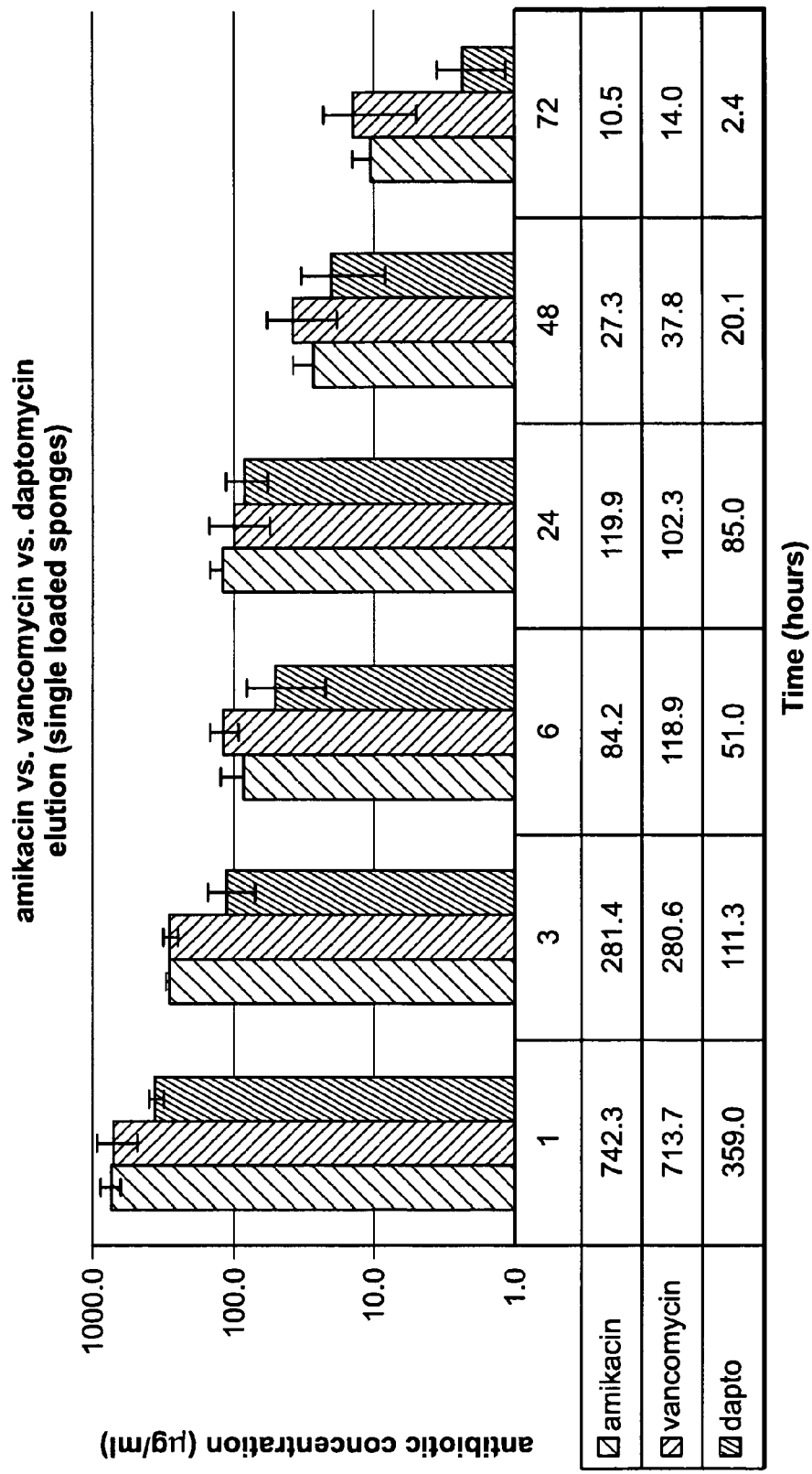
FIG. 17 is a graph showing the release of antibiotics from chitosan sponges. The chitosan sponges contained only 1 antibiotic per sponge (i.e., loaded with amikacin alone, vancomycin alone, and daptomycin alone). Amikacin and vancomycin release showed similar profiles throughout the duration of the study whereas daptomycin release was significantly less than the other two tested antibiotics by the 72 hr timepoint. Concentrations are given in micrograms per milliliter (20 ml PBS used as elution medium). A table is provided with the concentration measurements. The $1^{st}$ group contained amikacin only, the $2^{nd}$ group contained vancomycin only, and the $3^{rd}$ group contained daptomycin only. Solutions containing 5 mg/ml effective concentration of amikacin, vancomycin, or daptomycin was used to hydrate the chitosan sponges. (n=3).
Figure 18:
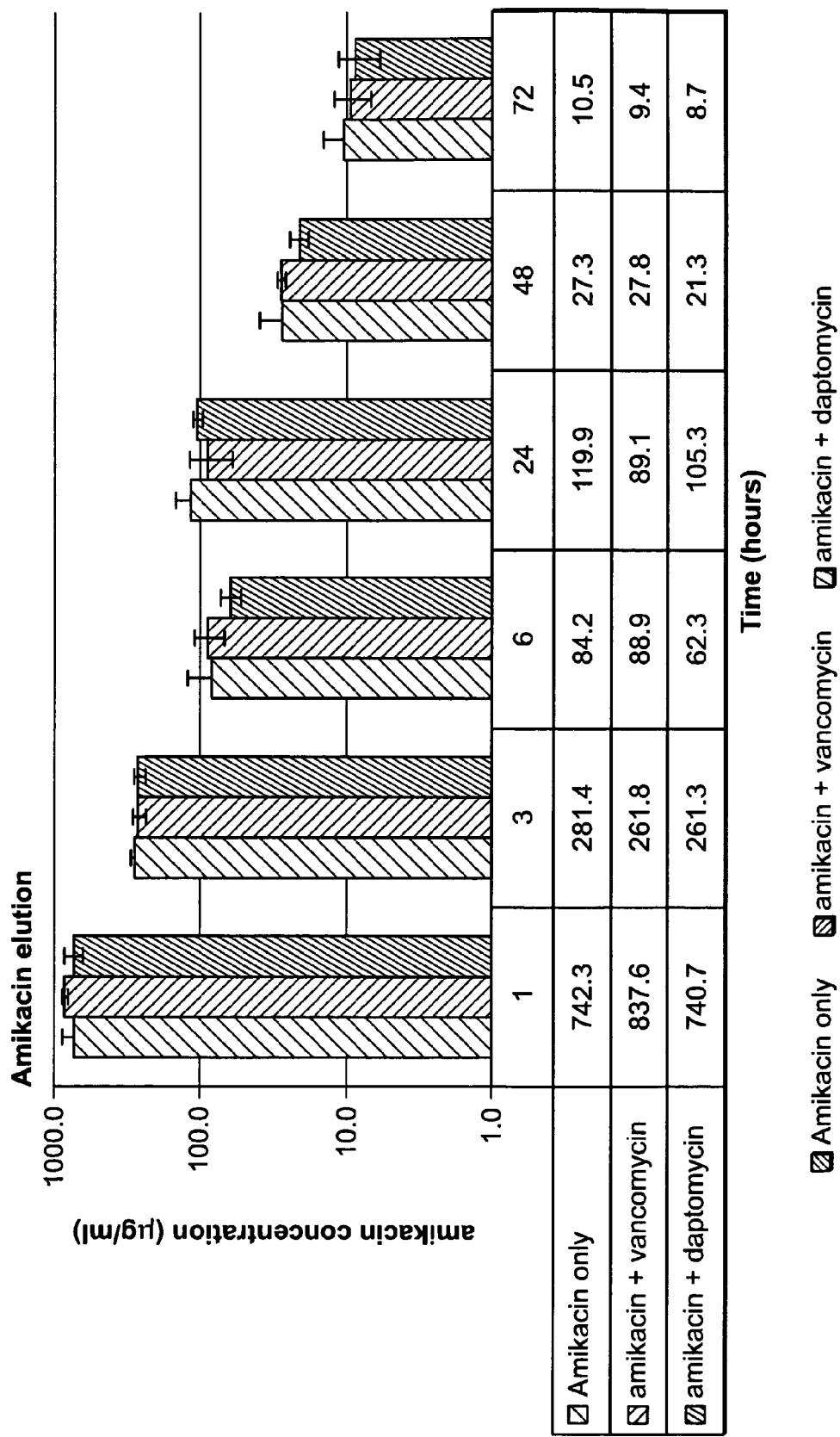
FIG. 18 is a graph showing the release of amikacin from chitosan sponges. Vancomycin nor daptomycin affected the release of amikacin. Concentrations given in micrograms per milliliter (20 ml PBS used as elution medium). A table is provided with the concentration measurements. The $1^{st}$ group was amikacin only, the $2^{nd}$ group contained amikacin+vancomycin, and the $3^{rd}$ group contained amikacin+daptomycin. Solutions containing 5 mg/ml effective concentration of amikacin, amikacin+vancomycin, or amikacin+daptomycin were used to hydrate the chitosan sponges. (n=3).
Figure 19:
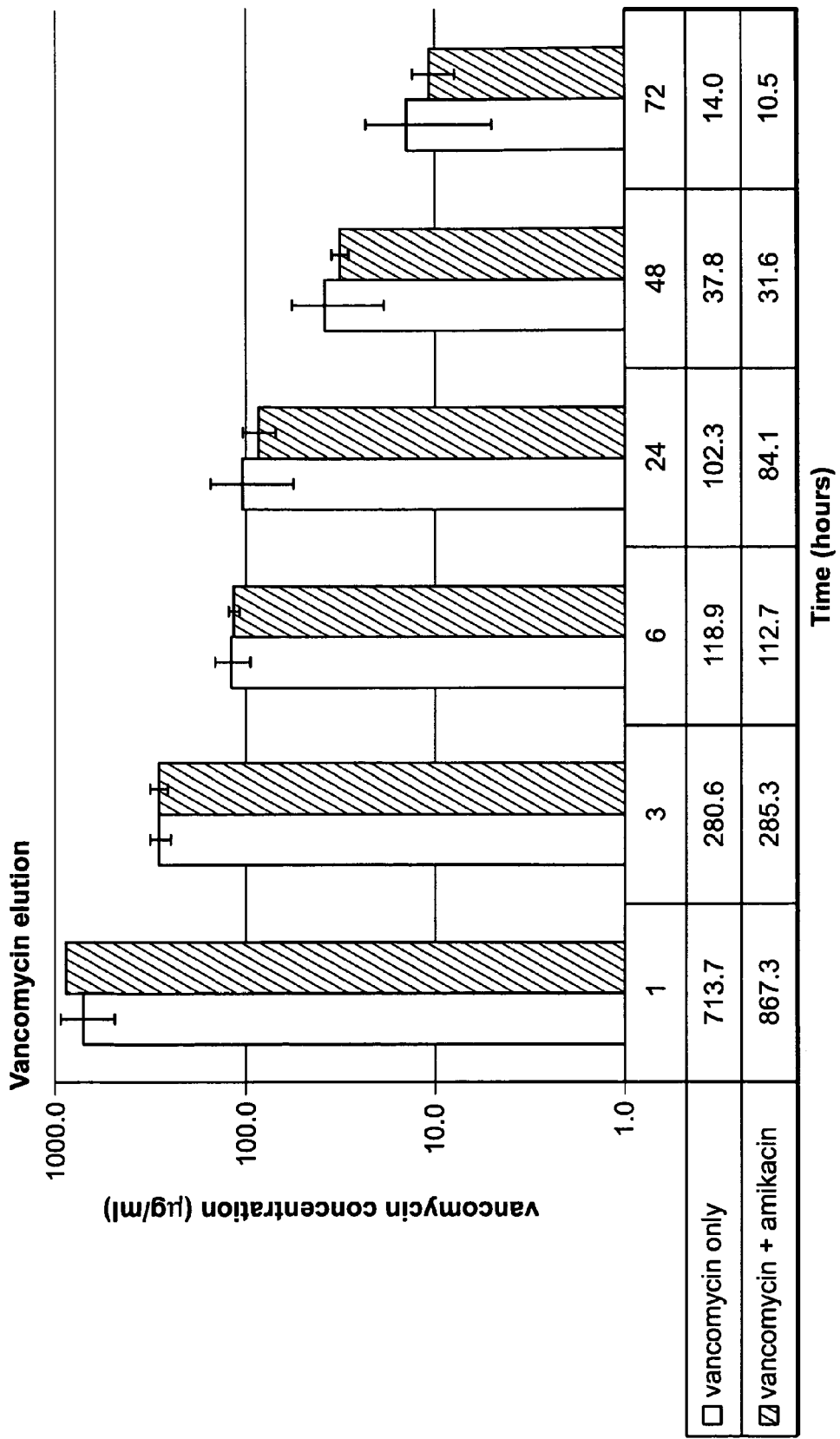
FIG. 19 is a graph showing the release of vancomycin from chitosan sponges. Amikacin did not affect the release of vancomycin. Concentrations given in micrograms per milliliter (20 ml PBS used as elution medium). A table is provided with the concentration measurements. The $1^{st}$ group was vancomycin only and the $2^{nd}$ group contained vancomycin+amikacin. Solutions containing 5 mg/ml effective concentration of vancomycin or vancomycin+amikacin were used to hydrate the chitosan sponges. (n=3).
Figure 20:
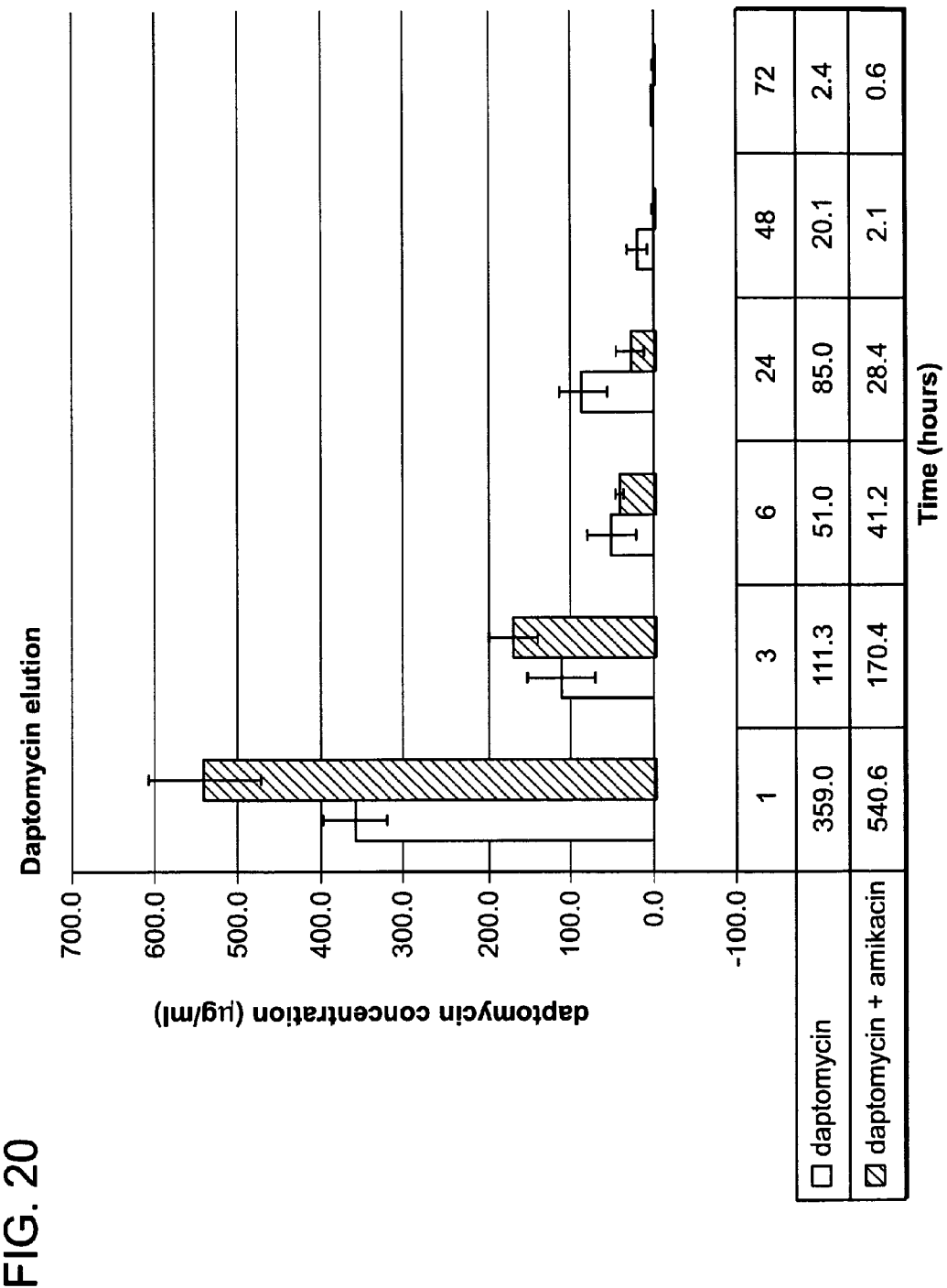
FIG. 20 is a graph showing the release of daptomycin from chitosan sponges. Amikacin did not affect the release of daptomycin. Concentrations given in micrograms per milliliter (20 ml PBS used as elution medium). A table is provided with the concentration measurements. The $1^{st}$ group contained daptomycin only and the $2^{nd}$ group contained daptomycin+amikacin. Solutions containing 5 mg/ml effective concentration of daptomycin or daptomycin+amikacin were used to hydrate the chitosan sponges. (n=3).

Agent elution from chitosan sponges loaded with the antibiotics amikacin, vancomycin, and daptomycin was analyzed in parallel (FIG. 17). As shown in FIG. 17, profiles for amikacin and vancomycin release was similar throughout the duration of the study whereas daptomycin release was significantly less than the other two tested antibiotics at the 72 hour time point. Agent elution from chitosan sponges loaded with more than one antibiotic was also analyzed. Amikacin elution from chitosan sponges was measured when chitosan sponges were loaded with amikacin alone, amikacin+vancomycin, and amikacin+daptomycin (FIG. 18). As shown in FIG. 18, vancomycin nor daptomycin affected the release of amikacin. Vancomycin elution from chitosan sponges was measured when chitosan sponges were loaded with vancomycin alone and vancomycin+amikacin (FIG. 19). As shown in FIG. 19, amikacin did not affect the release of vancomycin. Daptomycin elution from chitosan sponges was measured when chitosan sponges were loaded with daptomycin alone and daptomycin+amikacin (FIG. 20). As shown in FIG. 20, amikacin did not affect the release of vancomycin.

To determine whether agents eluted from the sponges could be used to inhibit bacterial growth, zone of inhibition (ZOI) studies were carried out (FIGS. 3A-3D). Chitosan sponges loaded with a single antibiotic or combinations of antibiotics, as above, were analyzed for their ability to inhibit bacterial growth. For the assays to determine inhibition of bacterial growth, the bacterial strains *Pseudomonas aeruginosa* and *Staphylococcus aureus* were used. Results showing the inhibition of *Pseudomonas aeruginosa* and *Staphylococcus aureus* are shown at Tables 2 and 3, respectively.

TABLE 2

Chitosan sponges loaded with antibiotics inhibited growth of *Pseudomonas aeruginosa*

| P. aeruginosa | 1 | 3 | 6 | 24 | 48 | 72 |
|---|---|---|---|---|---|---|
| amikacin only | − | − | − | − | + | + |
| amikacin + vancomycin | − | − | − | − | + | + |
| amikacin + daptomycin | − | − | − | + | + | + |

Bacterial growth of *Pseudomonas aeruginosa* in the presence of samples from the elution studies (FIGS. 17-20).
In each column, growth in defined with a (+) and lack of growth is defined with a (−).
(n = 3)

As shown in Table 2, none of the groups tested inhibited bacterial growth at 48 or 72 hours. Lack of inhibition was also observed at 24 hours with the amikacin+daptomycin group.

TABLE 3

Chitosan sponges loaded with antibiotics inhibited growth of *Staphylococcus aureus*

| S. aureus | 1 | 3 | 6 | 24 | 48 | 72 |
|---|---|---|---|---|---|---|
| amikacin only | − | − | − | − | − | − |
| vancomycin only | − | − | − | − | − | − |
| daptomycin only | − | − | − | − | − | − |
| amikacin + daptomycin | − | − | − | − | − | − |
| amikacin + vancomycin | − | − | − | − | − | + |

Bacterial growth of *Staphylococcus aureus* in the presence of samples from elution studies (FIGS. 17-20).
In each column, growth in defined with a (+) and lack of growth is defined with a (−).
(n = 3)

As shown in Table 3, all groups tested inhibited growth of *S. aureus* through 72 hours except the group containing amikacin+vancomycin, which showed lack of inhibition at the 72 hour timepoint.

Elution data from chitosan films is provided at Table 4. Films were submerged in 5 mg/ml amikacin or vancomycin solution for 2 minutes prior to elution testing. The elution was done in 50 ml of sterile saline solution and completely refreshed at each time point. The elution was carried out for 3 days. The values shown on the graph are in µg/ml.

TABLE 4

Elution data from amikacin and vancomycin loaded f

| Antibiotic | 1 hour | 3 hours | 6 hours | 24 hours | 48 hours | 72 hours |
|---|---|---|---|---|---|---|
| Amikacin (µg/ml) | 50.63 ± 4.49 | 2.15 ± 1.13 | 3.17 ± 1.14 | 3.93 ± 0.57 | 4.7 ± 2.49 | 0.6 ± 0.48 |
| Vancomycin (µg/ml) | 83.45 ± 17.25 | 19.35 ± 7.98 | 0.58 ± 0.88 | 2.53 ± 0.66 | 9.72 ± 1.92 | 6.13 ± 0.39 |

Table 4 displays amikacin and vancomycin elution from sterilized chitosan films corresponding to FIG. 1C.

Figure 5A:
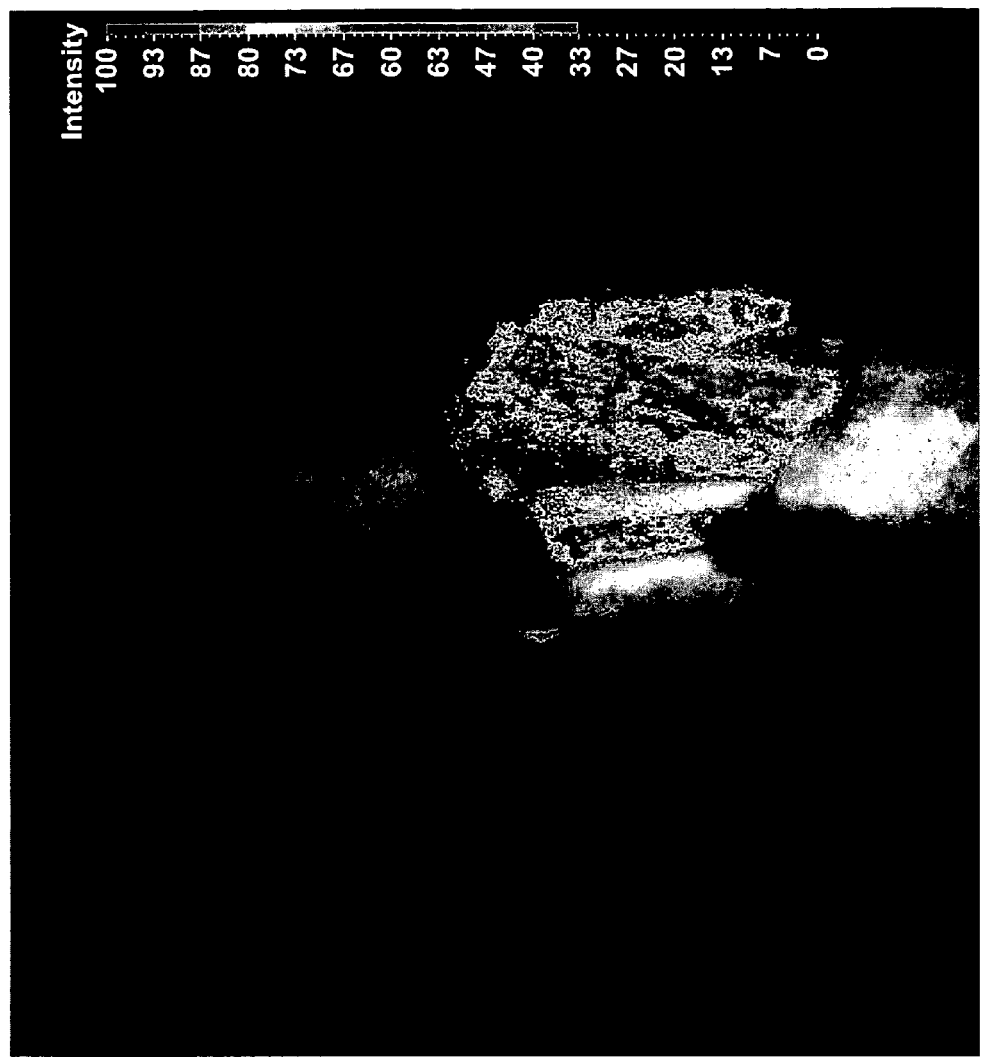
FIGS. 5A-5D are images showing bacteria levels in a tibial fracture model in goats.
Figure 5B:
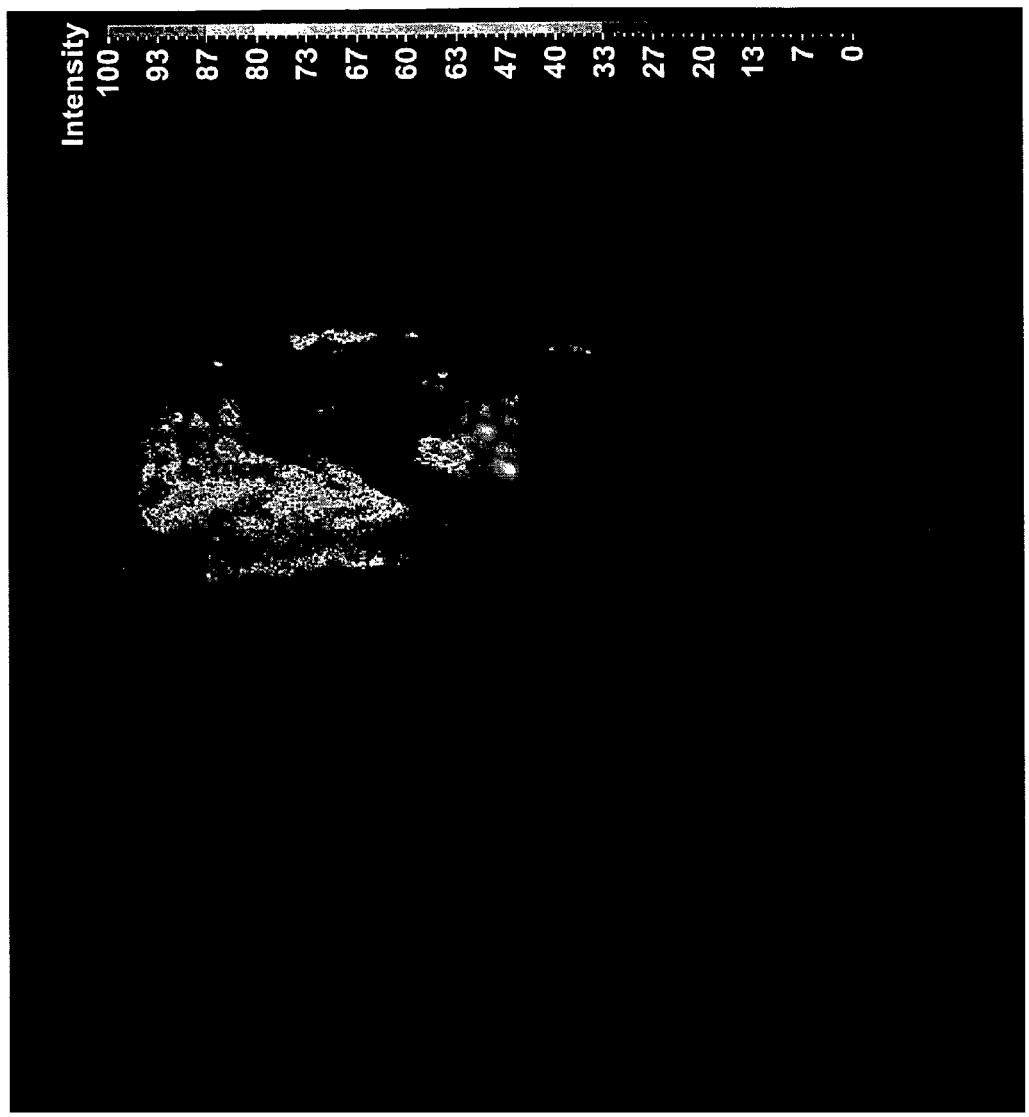
Figure 5C:
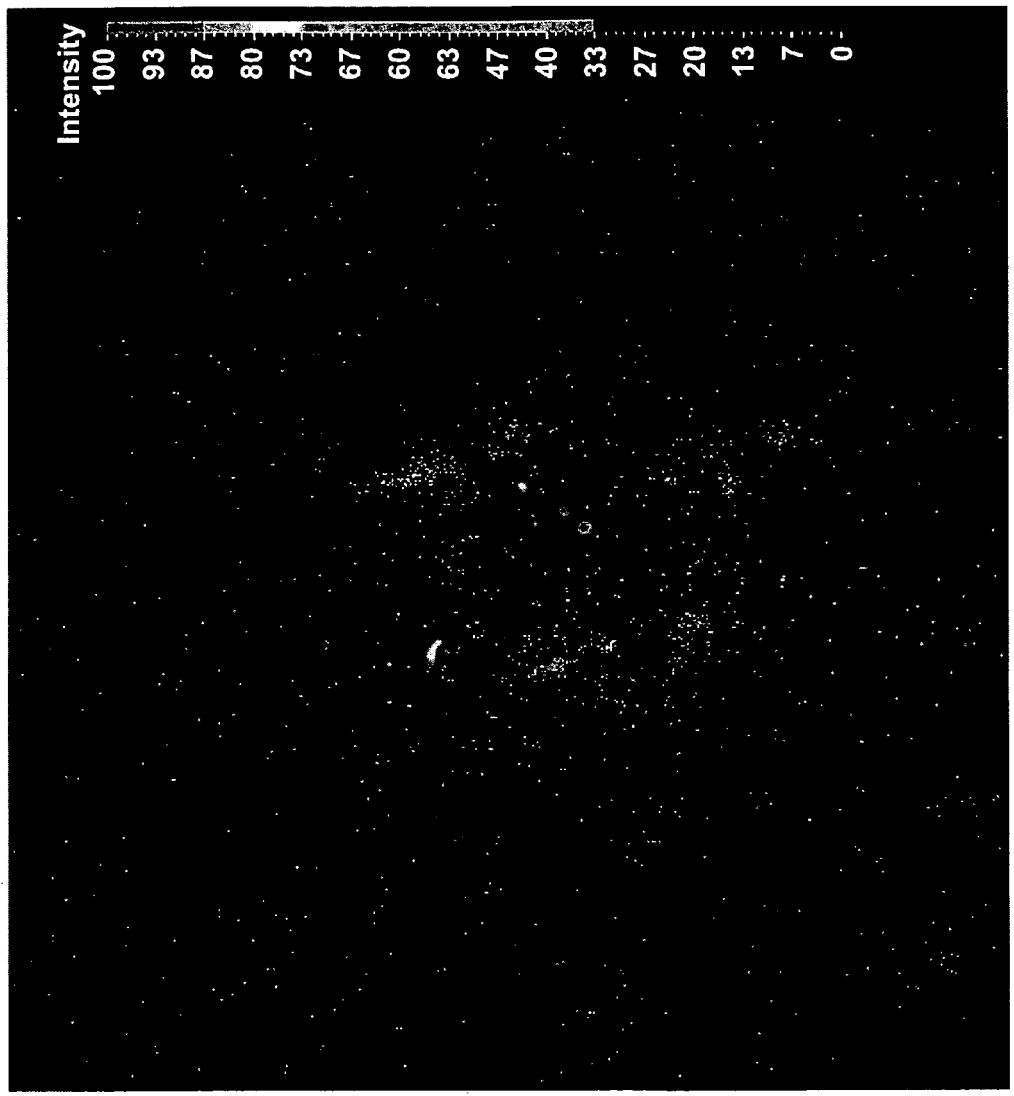
Figure 5D:
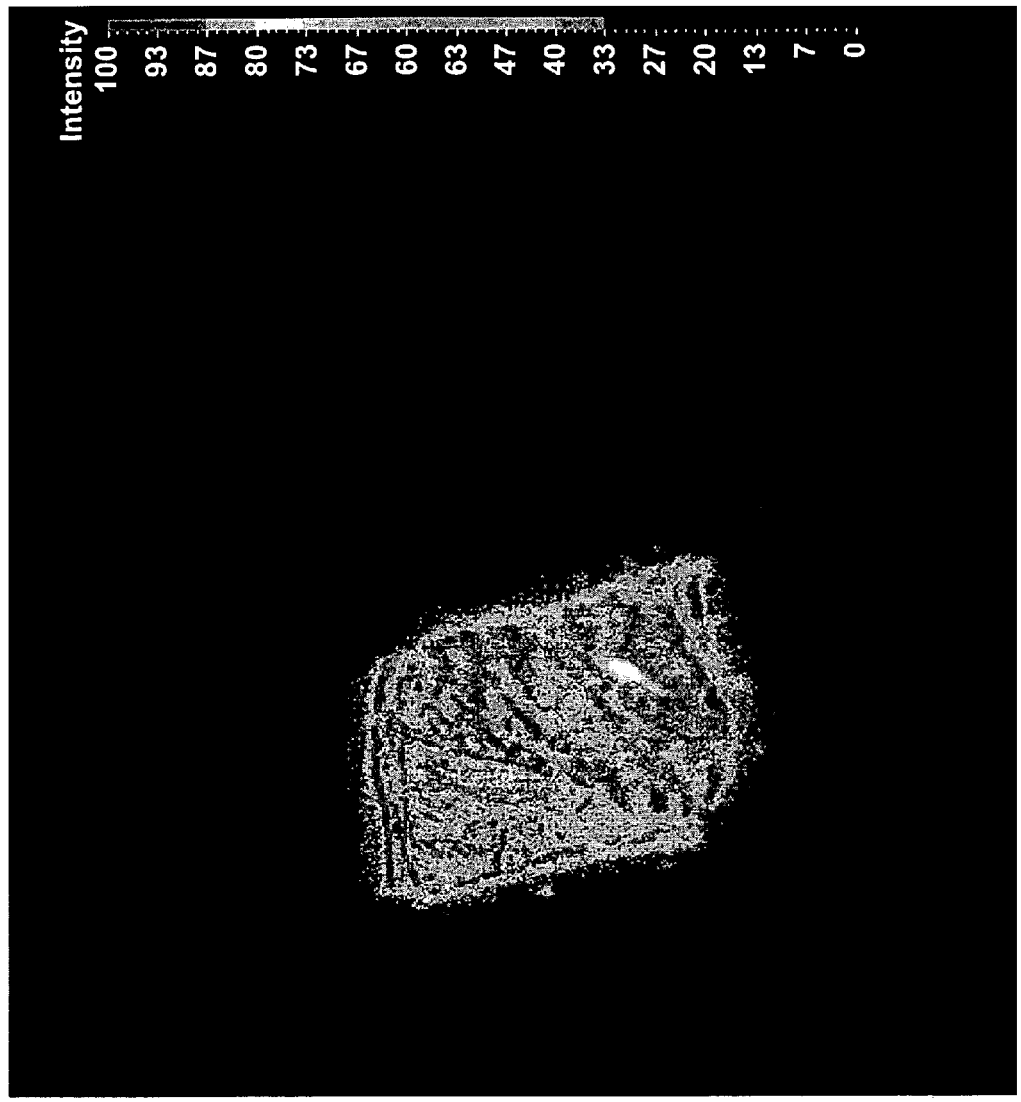
Figure 6:
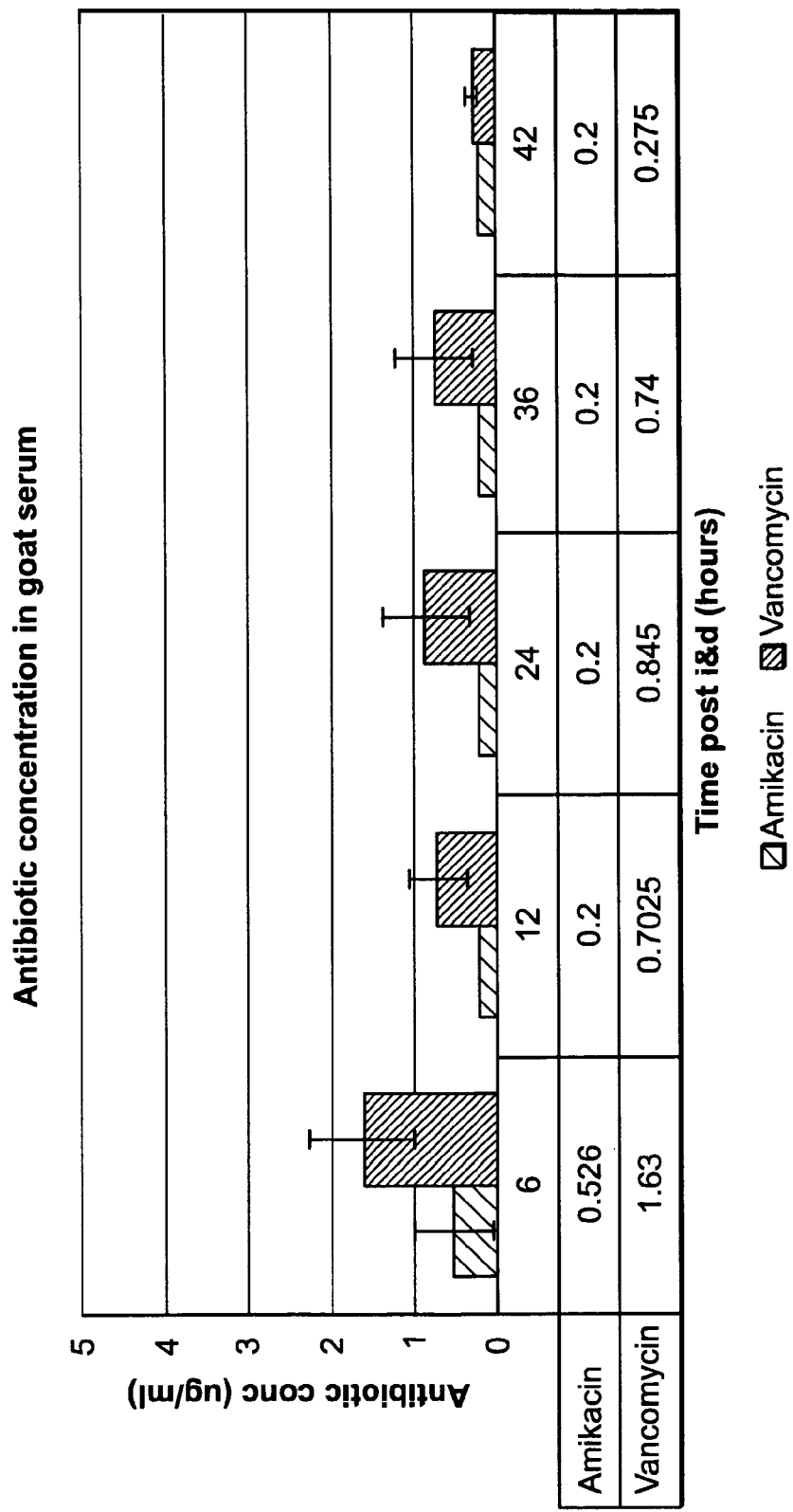
FIG. 6 provides a graphical representation of antibiotic levels found in goat serum during animal testing. Blood was drawn at 6, 12, 24, 36, and 42 hours post-operation. Serum antibiotic levels were measured by TDx. (amikacin and vancomycin). Values listed are µg/ml+−std. dev) (n=5 for amikacin samples and n=4 for vancomycin). left column, amikacin; right column, vancomycin.

Sponges were also used in a well-established, contaminated tibial fracture model in goats. This model mimics an orthopaedic trauma injury as seen in military combat due to Improvised Explosive Devices (IEDs). This model contains muscle, bone, and tissue injuries with thermal damage to each. The sponges were hydrated in amikacin (*P. aeruginosa*) or vancomycin (*S. aureus*) [5 mg/ml solution] for 60 seconds. The goats were euthanized at 48 hours and imaged a third time to quantify bacteria levels (FIG. 5D). Blood was drawn to monitor serum levels of antibiotic at 6, 12, 24, 36, and 42 hours. Results are shown in FIG. 6 and in Table 5 (below).

The wound was inoculated with *Pseudomonas aeruginosa* (lux) or *Staphylococcus aureus* (lux) bacteria and closed for 6 hours. FIGS. 4A-4D show quantitation of bacteria present in the wound at the indicated time point. After 6 hours, the wound was opened and imaged to obtain bacterial luminescent intensity (FIG. 5A-5D). The amount of light intensity was recorded as a baseline value for bacterial contamination. The wound was debrided and irrigated with 9 L of sterile saline solution. After irrigation, the wound was imaged a second time. Goats in the treatment group received an antibiotic-loaded chitosan sponge, which was placed in the wound before the wound was closed.

In the absence of local administration of an antibiotic using a chitosan sponge, high levels of bacteria were found in wounds despite irrigation and debridement. Goat 841 had a 65% reduction in bacterial cell count after irrigation and debridement. This value rebounded to 214% of 6-hour pre-irrigation and debridement cell count after 42 hours with no other treatment. Goat 843 had a 61% reduction in bacterial cell count after irrigation and debridement. This value rebounded to 91% of 6-hour pre-irrigation and debridement cell count after 42 hours with no other treatment. Goat 845 had a 93% reduction in bacterial cell count after irrigation and debridement. This value rebounded to 56% of 6-hour pre-irrigation and debridement cell count after 42 hours with no other treatment. Goat 846 had a 95% reduction in bacterial cell count after irrigation and debridement. This value rebounded to 20% of 6-hour pre-irrigation and debridement cell count after 42 hours with no other treatment. Goat 847 had an 89% reduction in bacterial cell count after irrigation and debridement. This value rebounded to 30% of 6-hour pre-irrigation and debridement cell count after 42 hours with no other treatment.

In contrast, goats that received local administration of amikacin via a chitosan sponge had virtually no *Pseudomonas aeruginosa* bacteria present in their wounds. Goat 8 had an 87% reduction in bacterial cell count after irrigation and debridement. This value was reduced to 0% after 42 hour treatment with an amikacin-loaded chitosan sponge. Goat 32 had an 91% reduction in bacterial cell count after irrigation and debridement. This value was reduced to 1% after 42 hour treatment with an amikacin-loaded chitosan sponge. Goat 839 had an 89% reduction in bacterial cell count after irrigation and debridement. This value was reduced to 1% after 42 hour treatment with amikacin-loaded chitosan sponge. Goat 842 had an 87% reduction in bacterial cell count after irrigation and debridement. This value was reduced to 0% after 42 hour treatment with amikacin-loaded chitosan sponge. Goat 2026 had an 81% reduction in bacterial cell count after irrigation and debridement. This value was reduced to 0% after 42 hour treatment with amikacin-loaded chitosan sponge.

Similar results were observed when vancomycin-loaded chitosan sponges were used. In the control group, goats showed high levels of bacteria (*Staphylococcus aureus*) in their wounds despite irrigation and debridement. Goat 14069 had a 22% reduction in bacterial cell count after irrigation and debridement. This value rebounded to 2464% of 6-hour pre-irrigation and debridement cell count after 42 hours with no other treatment. Goat 7147 had an 81% reduction in bacterial cell count after irrigation and debridement. This value rebounded to 159% of 6-hour pre-irrigation and debridement cell count after 42 hours with no other treatment. Goat 20 had a 73% reduction in bacterial cell count after irrigation and debridement. This value rebounded to 157% of 6-hour pre-irrigation and debridement cell count after 42 hours with no other treatment. Goat 94 had a 76% reduction in bacterial cell count after irrigation and debridement. This value rebounded to 357% of 6-hour pre-irrigation and debridement cell count after 42 hours with no other treatment. Goat 263 had a 59% reduction in bacterial cell count after irrigation and debridement. This value rebounded to 249% of 6-hour pre-irrigation and debridement cell count after 42 hours with no other treatment.

Importantly, goats treated with chitosan sponges loaded with vancomycin did not show the *Staph aureus* bacterial rebound observed in the control group. For example, Goat 840 had a 74% reduction in bacterial cell count after irrigation and debridement. This value was reduced to 0% after 42 hour treatment with a vancomycin-loaded chitosan sponge. Goat 155 had a 72% reduction in bacterial cell count after irrigation and debridement. This value was reduced to 1% after 42 hour treatment with a vancomycin-loaded chitosan sponge. Goat 837 had an 88% reduction in bacterial cell count after irrigation and debridement. This value was reduced to 7% after 42 hour treatment with a vancomycin-loaded chitosan sponge.

TABLE 5

Serum levels of amikacin and vancomycin drawn over 42 hours.

| Amikacin concentrations | | Vancomycin concentrations | |
|---|---|---|---|
| Time | Conc (mean ± standard deviation) | Time | Conc (mean ± standard deviation) |
| 6 hr | 0.526 ± 0.478 (ug/ml) | 6 hr | 1.630 ± 0.646 (ug/ml) |
| 12 hr | 0.200 ± 0.000 (ug/ml) | 12 hr | 0.703 ± 0.348 (ug/ml) |
| 24 hr | 0.200 ± 0.000 (ug/ml) | 24 hr | 0.845 ± 0.539 (ug/ml) |
| 36 hr | 0.200 ± 0.000 (ug/ml) | 36 hr | 0.740 ± 0.477 (ug/ml) |
| 42 hr | 0.200 ± 0.000 (ug/ml) | 42 hr | 0.275 ± 0.070 (ug/ml) |

The data given above is the actual antibiotic levels found in goat serum during a established fracture/wound model. The levels taper off from the initial 6 hour draw to the conclusion of the 42 hour study. All values are given in µg/ml.

Sponge fragments remained in 8 of the 10 goats treated with chitosan sponges. The values listed in Table 6 (below) show the antibiotic remaining in each fragment, which was eluted by soaking the sponge fragment for 12 hours in sterile saline solution. The values were normalized to the mass of the sponge remnants, hence the values listed are in μg/ml/g. Goats 8, 32, 839, and 842 were treated with amikacin and goats 155, 837, 840, and 2437 were treated with vancomycin.

TABLE 6

Antibiotic Elution from Remaining Sponge Fragments

| Goat #/timepoint | 12 hr TDx reading (ug/ml/g) | Goat #/ timepoint | 12 hr TDx reading (ug/ml/g) |
|---|---|---|---|
| 8 | 1.60 | 155 | 4.18 |
| 32 | 0.25 | 837 | 2.31 |
| 839 | 0.48 | 840 | 2.28 |
| 842 | 0.08 | 2437 | 6.36 |
| Mean: | 0.60 | Mean: | 3.78 |
| Std Dev: | 0.68 | Std Dev: | 1.93 |

Values listed are amikacin (8,32,838,842) and vancomycin (155,837,840,2437) concentrations after 12 hours in sterile saline solution. The samples were retrieved from a goat after 42 hours in an in vivo study. Values were normalized to account for initial mass of the remaining sponge. Samples were submerged in 20 ml of sterile saline solution and kept at 37° C. for 12 hours.

At the time the sponge fragments were removed, it appeared that all of the implanted sponges had degraded between 60-100% after 42 hours post-implantation. The sponges were designed to elute and degrade over 72 hours. In vitro testing confirmed a 72 hour degradation profile.

Figure 4A:
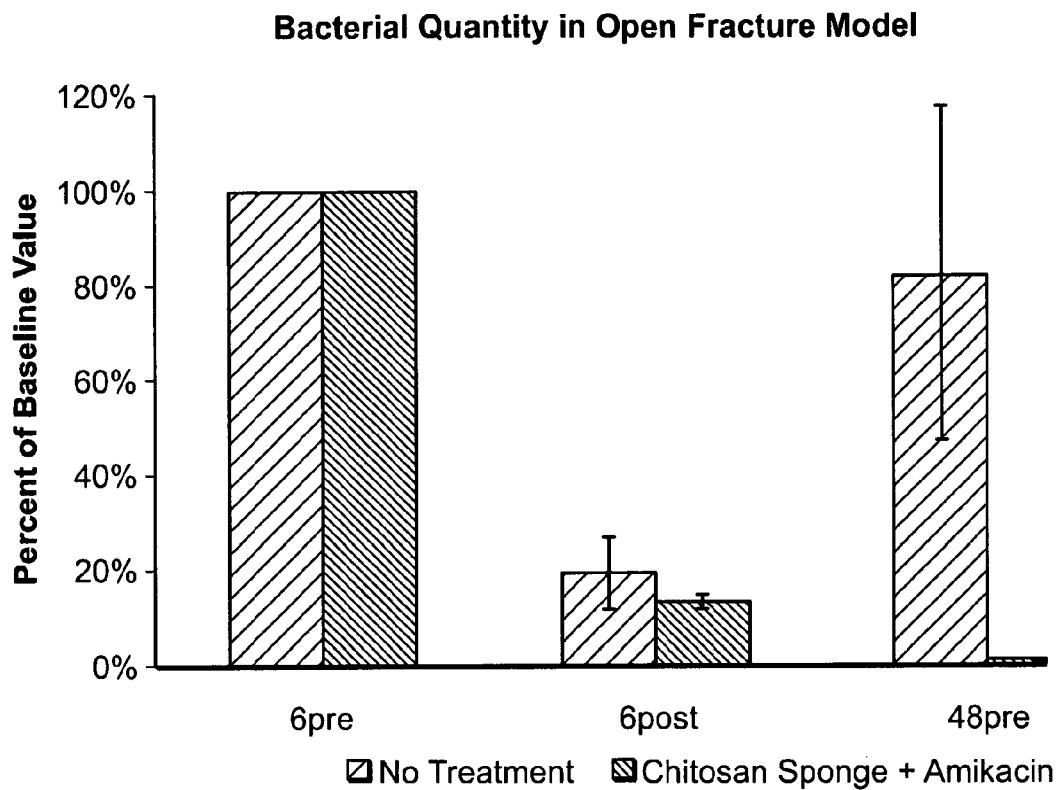
FIGS. 4A-4D are graphs showing bacterial cell quantity in a goat open tibial fracture model.
Figure 4B:
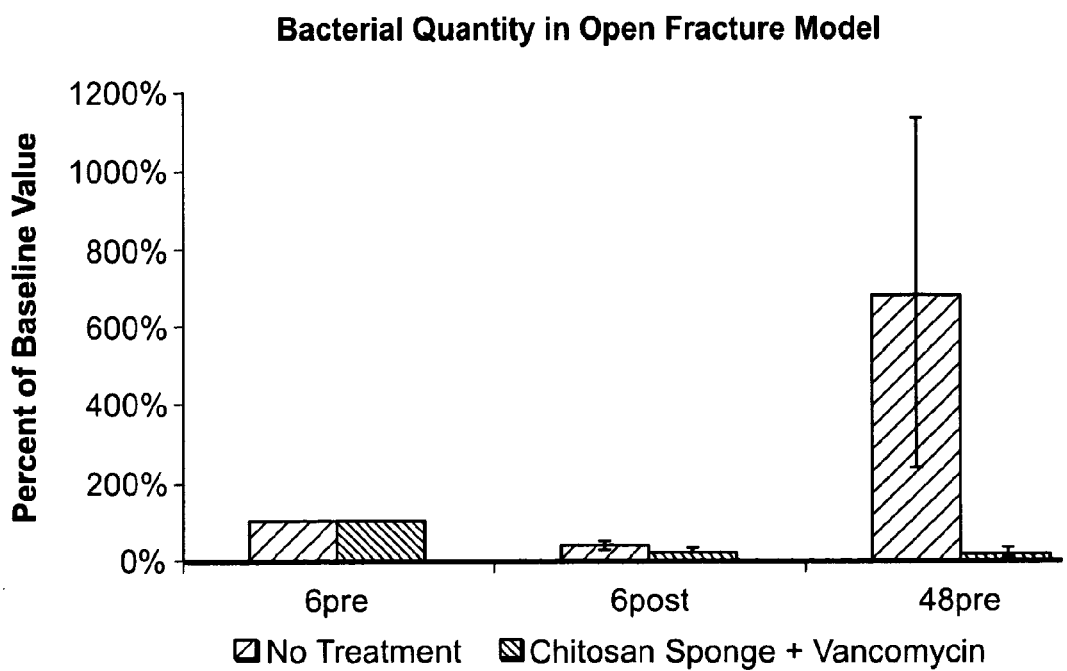
Figure 4C:
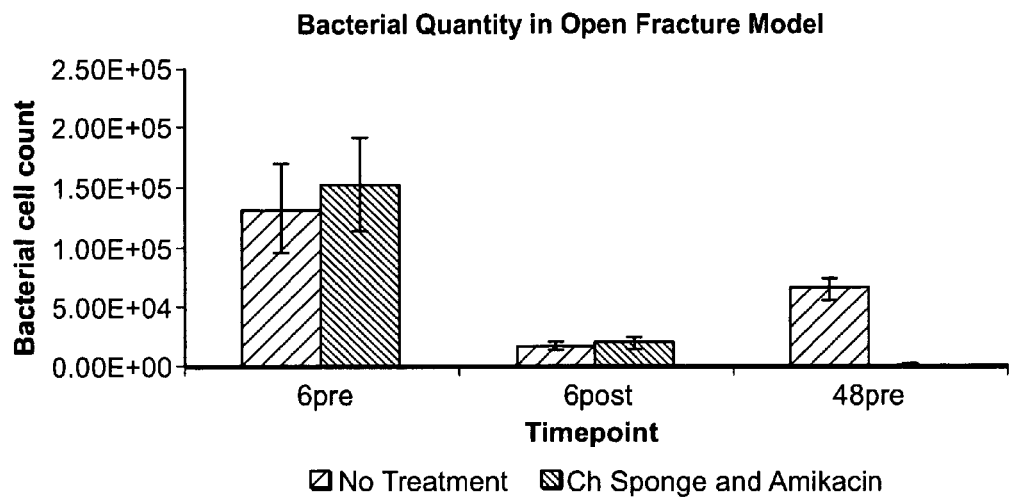
Figure 4D:
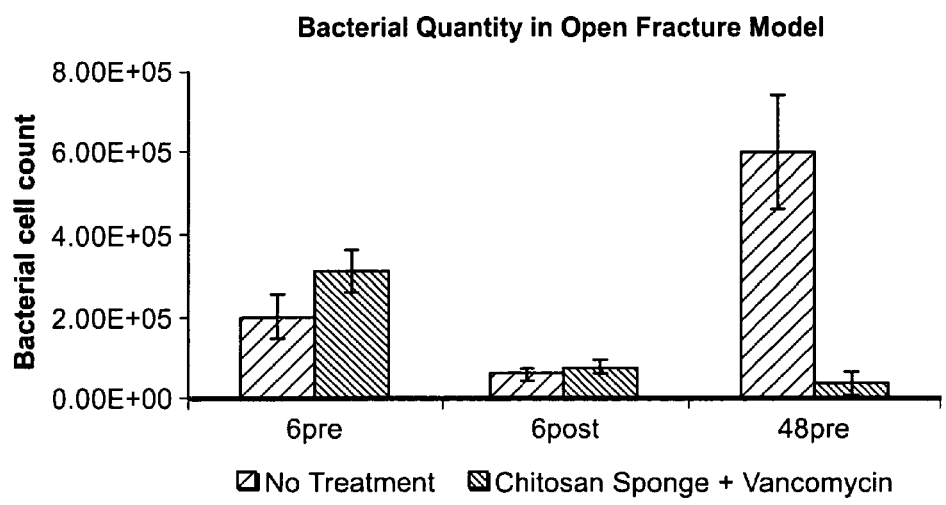

These results indicated that chitosan provides a degradable carrier matrix capable of delivering antibiotic agents locally alone or as an adjunctive therapy to standard treatment methods for traumatic orthopaedic injuries. The prevention of infection from orthopaedic trauma and surgical sites is of significant interest to the healthcare community. The use of a chitosan sponge as an early stage adjunctive treatment has significantly improved bacterial eradication in both the *Pseudomonas aeruginosa* and *Staphylococcus aureus* models (FIGS. 4A and 4B). In vitro analyses of these chitosan sponges has provided valuable information with respect to optimal manufacturing to tune degradation and elution rates. In vivo evaluation indicated that chitosan acts as a biocompatible, biodegradable carrier for antibiotics and successfully delivered these agents to aid in bacterial eradication in complex, contaminated wounds.

Example 3

Chitosan Films Maintain Mechanical Integrity after Re-Hydration

The following study shows that chitosan films can be used as an adaptable implant for musculoskeletal wound infection prevention or treatment. Dehydrated chitosan film absorb antibiotics and elute drugs over time. Chitosan films also biodegrade in the body. The results provided below show that a chitosan drug delivery device can be customized by a clinician through in situ antibiotic loading. Such compositions maintain rehydrated mechanical integrity.

During in situ loading the chitosan film absorbs antibiotics through rehydration. In one embodiment, antibiotic loading is carried out in an operating room or other clinical setting, immediately prior to implantation. This allows a clinician to tailor the drug delivery device to the patient's need through antibiotic choice and concentration. These properties allow for chitosan's use in infected musculoskeletal wound treatment. As shown herein, use of the device prevents and/or treats infection through localized antibiotic delivery, provides for attachment of chitosan films to implant devices employing chitosan's adhesion properties, and chitosan's degradation in the body eliminates the need for an additional surgery to recover an implanted device.

Figure 7:
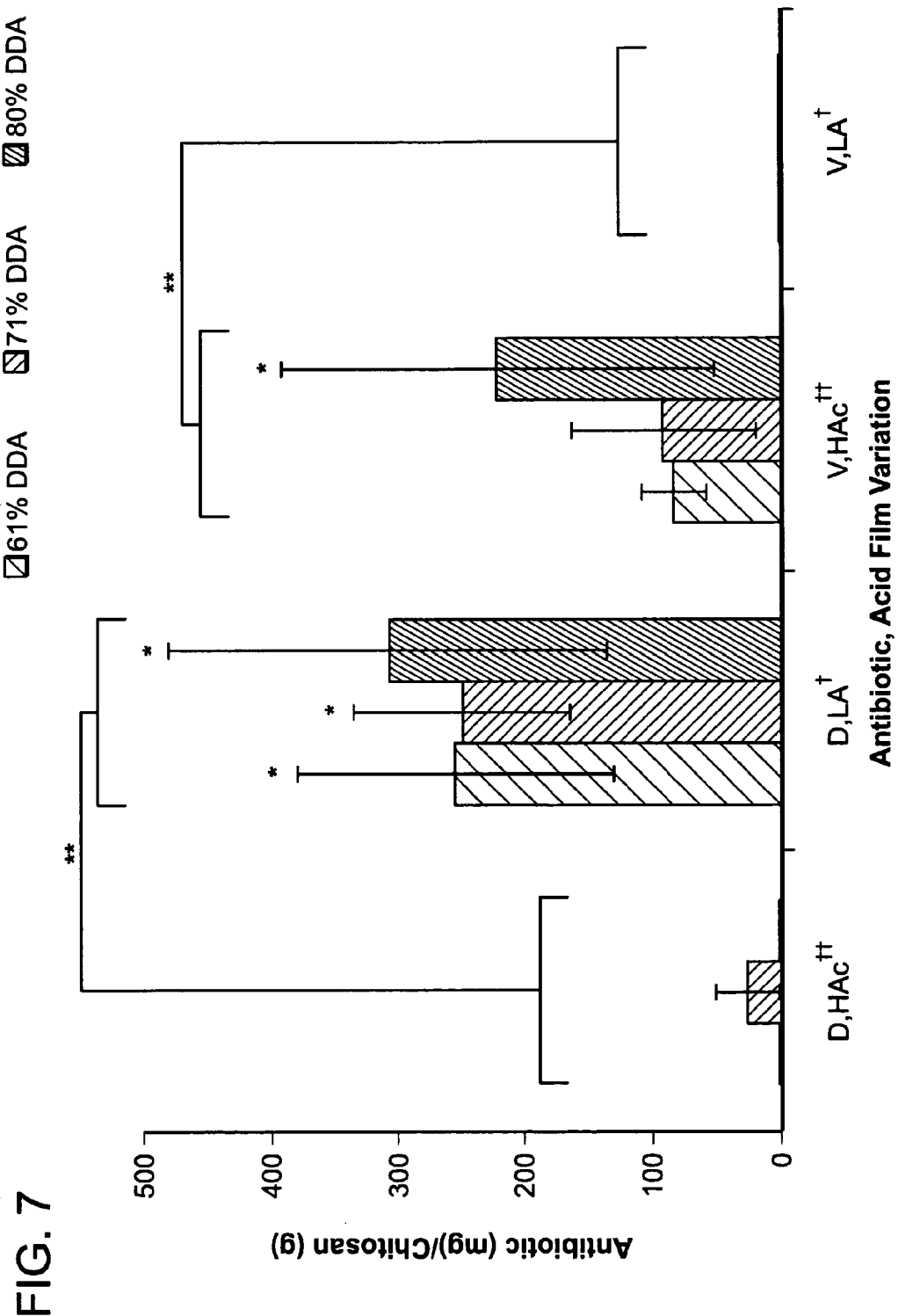
FIG. 7 is a graph that shows antibiotic uptake results. Daptomycin is abbreviated as D, vancomycin as V, and neither as N; the numbers 61, 71, and 80 are used to indicate the % degree of deacetylation; the acid solvents, lactic acid and acetic acid, are abbreviated LA and HAc, respectively. Daptomycin with lactic acid and vancomycin with acetic acid film variations had the highest antibiotic uptake values. The results are represented as the average±standard deviation (*, p≥0.7769; * vs. all others, **, †, ††, p<0.0001).
Figure 8:
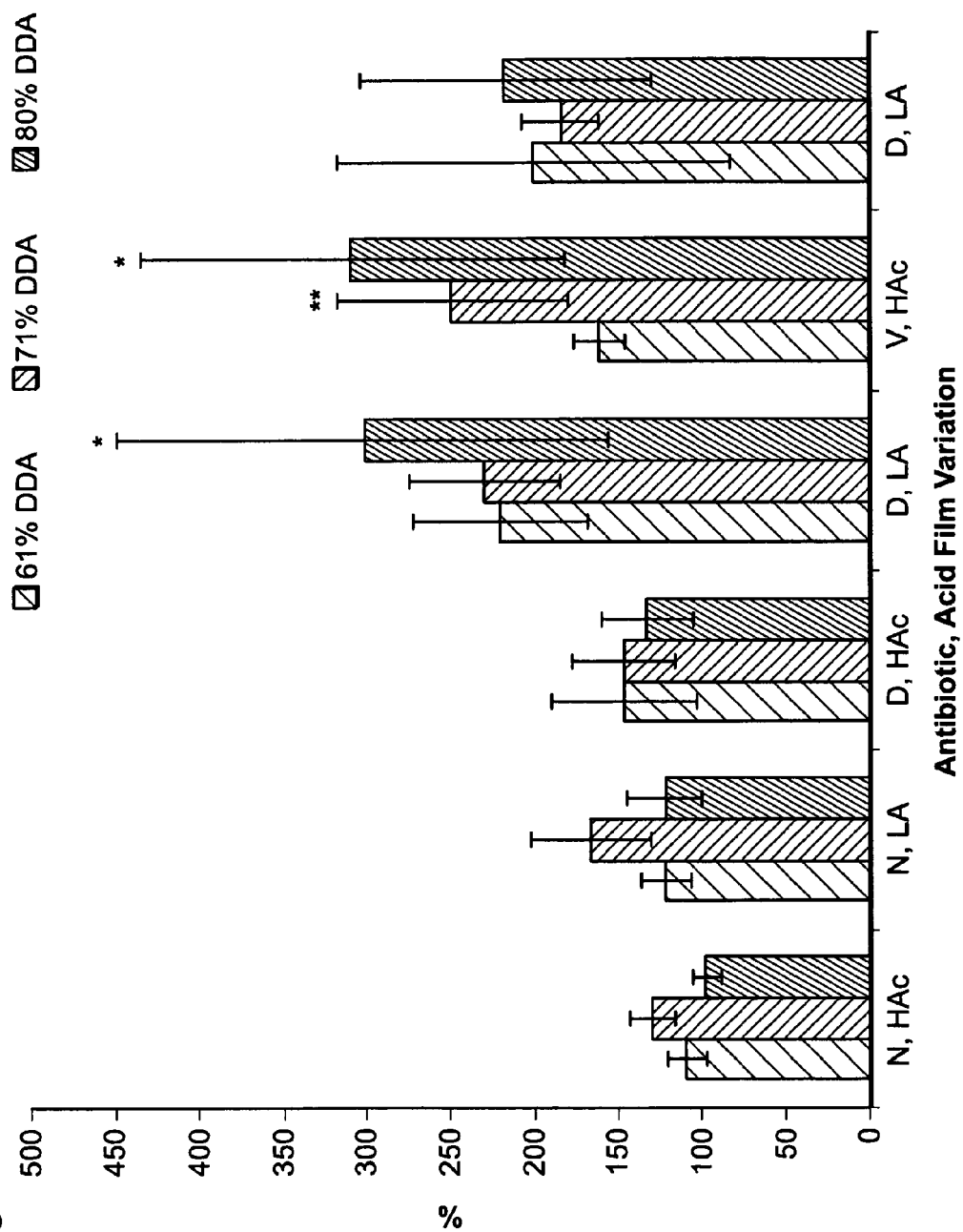
FIG. 8 is a graph that indicates the swelling ratio of the chitosan film variations after one minute rehydration by in situ loading. n=6 measurements for all groups. D, LA and V, HAc film variations had a higher swelling ratio. The results are represented as the average±standard deviation (*, p=0.8381; * vs. all others except **, p<0.0001).
Figure 9:
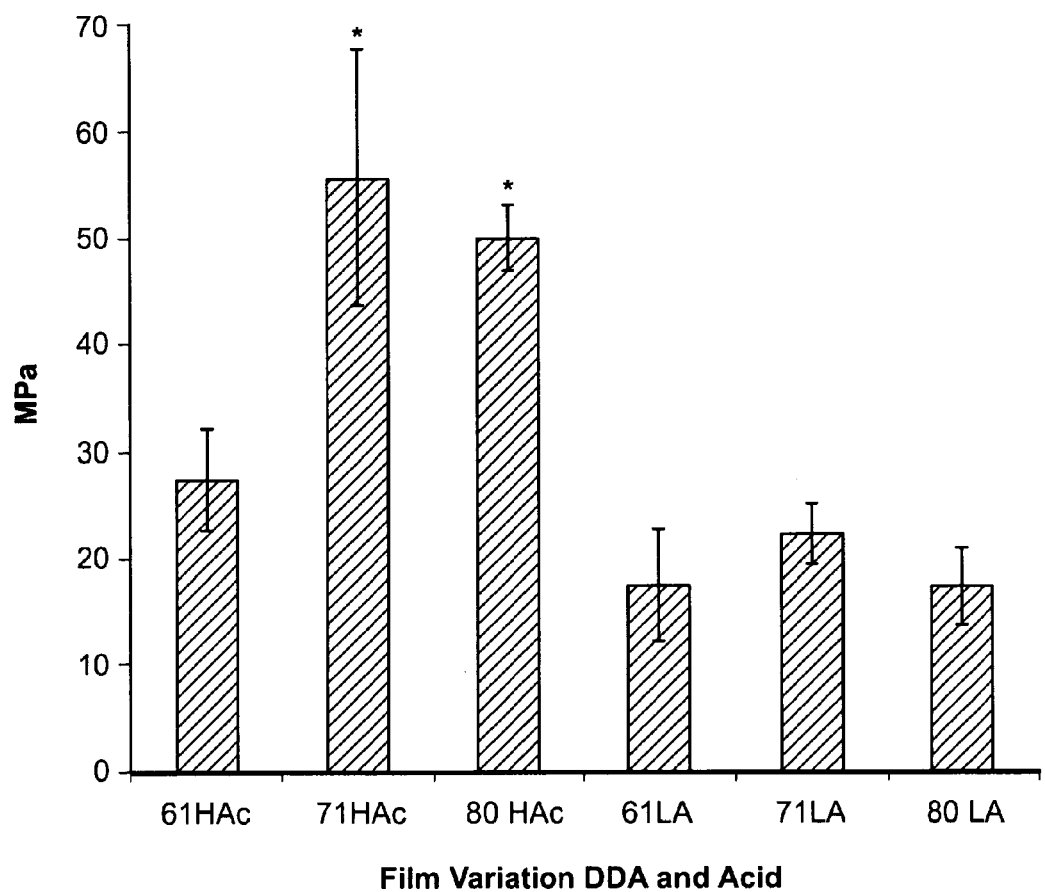
FIG. 9 is a graph showing ultimate tensile strength (UTS) results. As a measure of strength, UTS indicated the stress at which a dehydrated chitosan film specimen broke in MPa. The ultimate tensile strength of dehydrated chitosan films reported in stress, (*, p=0.2131; * vs. all others, p<0.0001). Film variations 71HAc and 80HAc were similar and had significantly higher UTS values than other variations. n=6 measurements for all groups.
Figure 10:
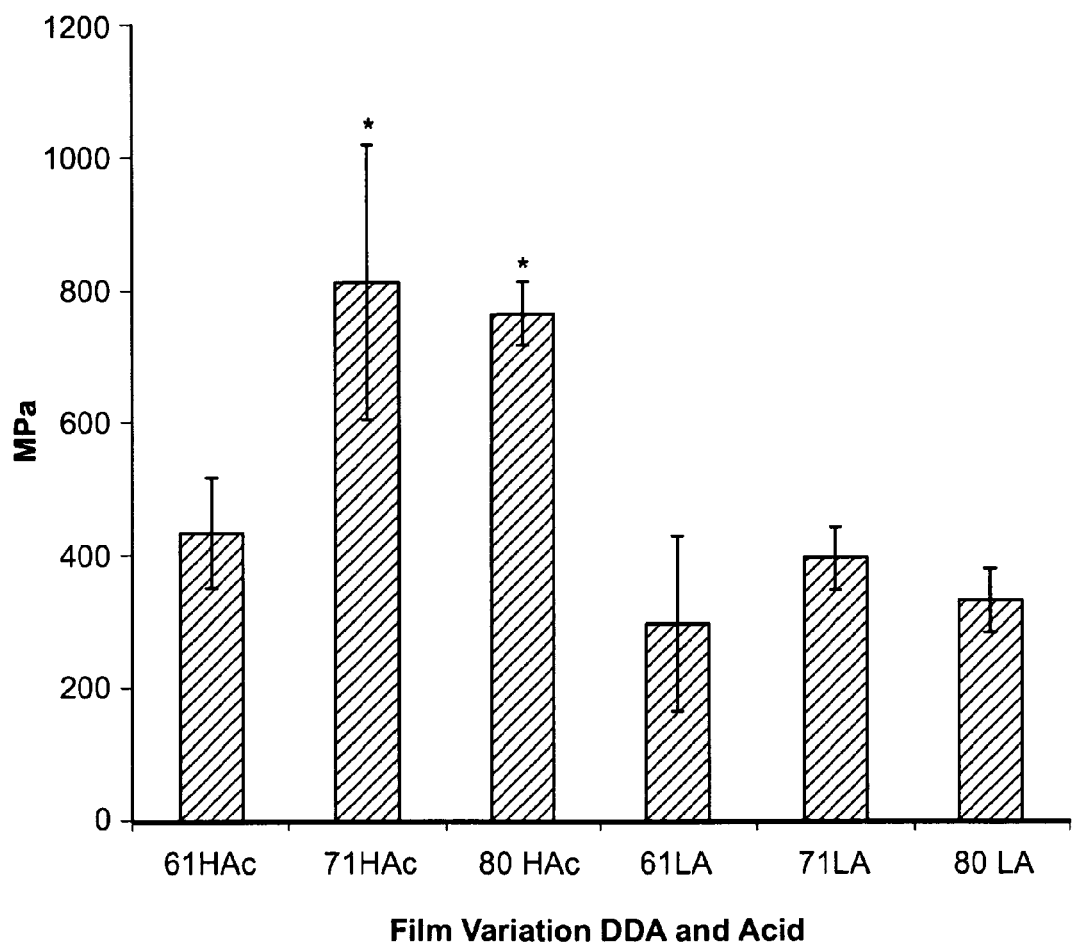
FIG. 10 is a graph quantitating elasticity results. The Young's Modulus indicated the ratio of stress to strain in MPa. Results are shown as the average±standard deviation (, p=0.6597;  vs. all others, p<0.0001). Film variations 71HAc and 80HAc were similar and had significantly higher Young's modulus than all other variations. n=6 measurements for all groups.
Figure 11A:
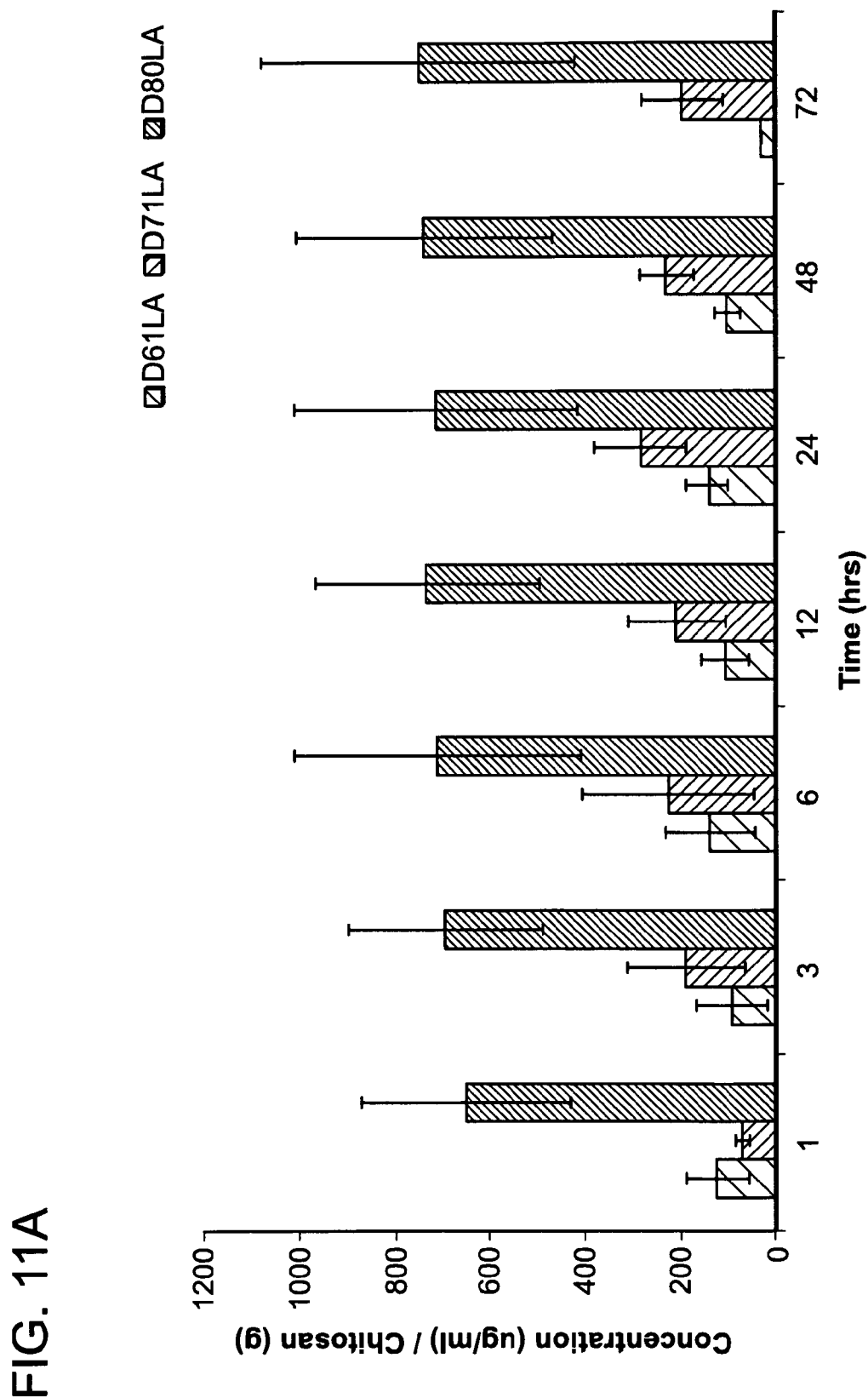
FIGS. 11A and 11B are graphs showing elution of daptomycin and vancomycin, respectively, from in situ loaded chitosan films represented as the average±standard deviation. Both antibiotic release profiles for 71% DDA films showed a bell shaped release. n=3 measurements for all groups.
Figure 12:
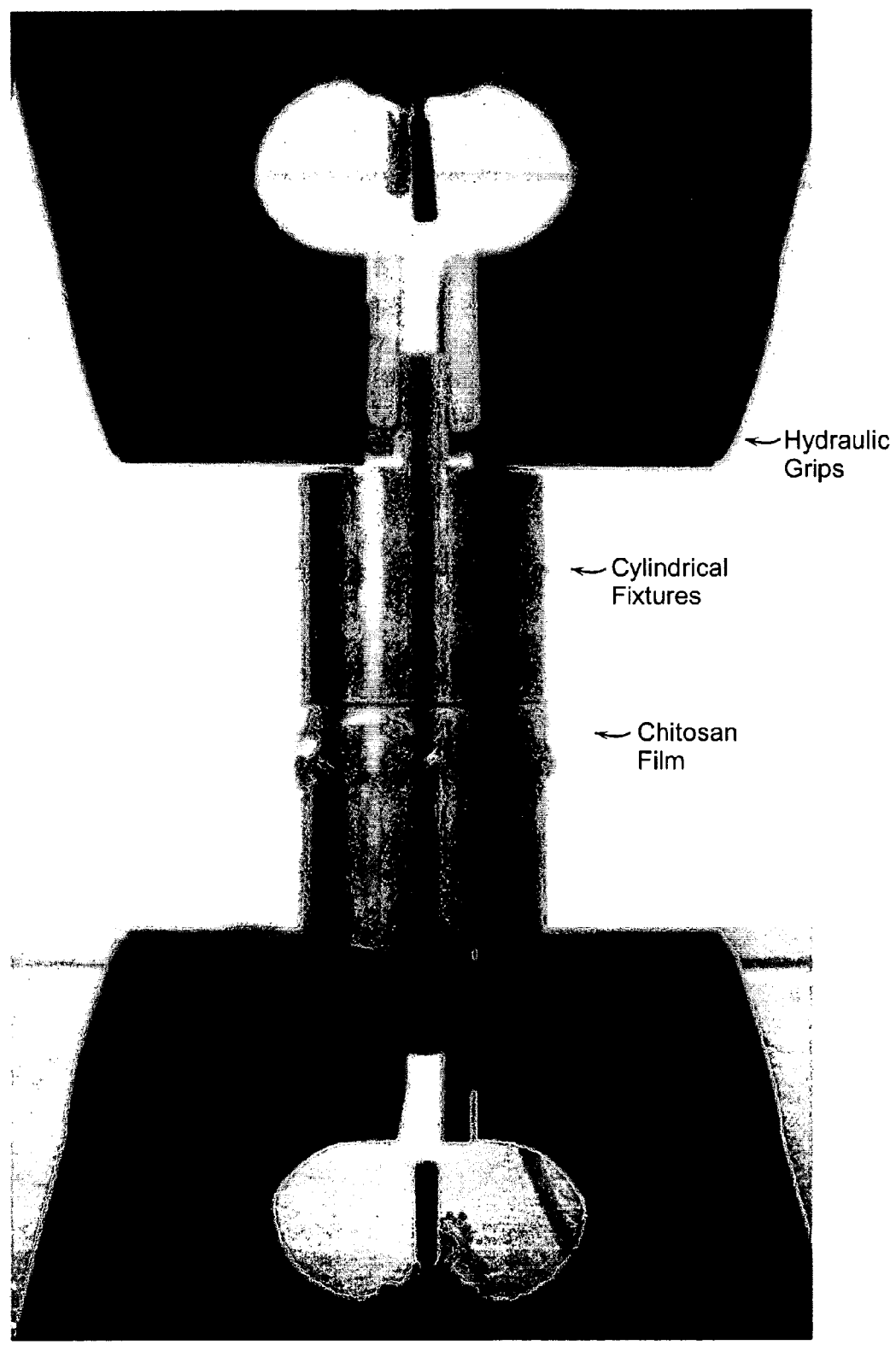
FIG. 12 shows a universal testing machine that is used to measure the strength required to pull implant components or fixtures apart. Cylindrical adhesive testing fixtures are shown positioned in the grips of the universal tensile machine with hydrated chitosan film in position between the adhesive fixtures.
Figure 13:
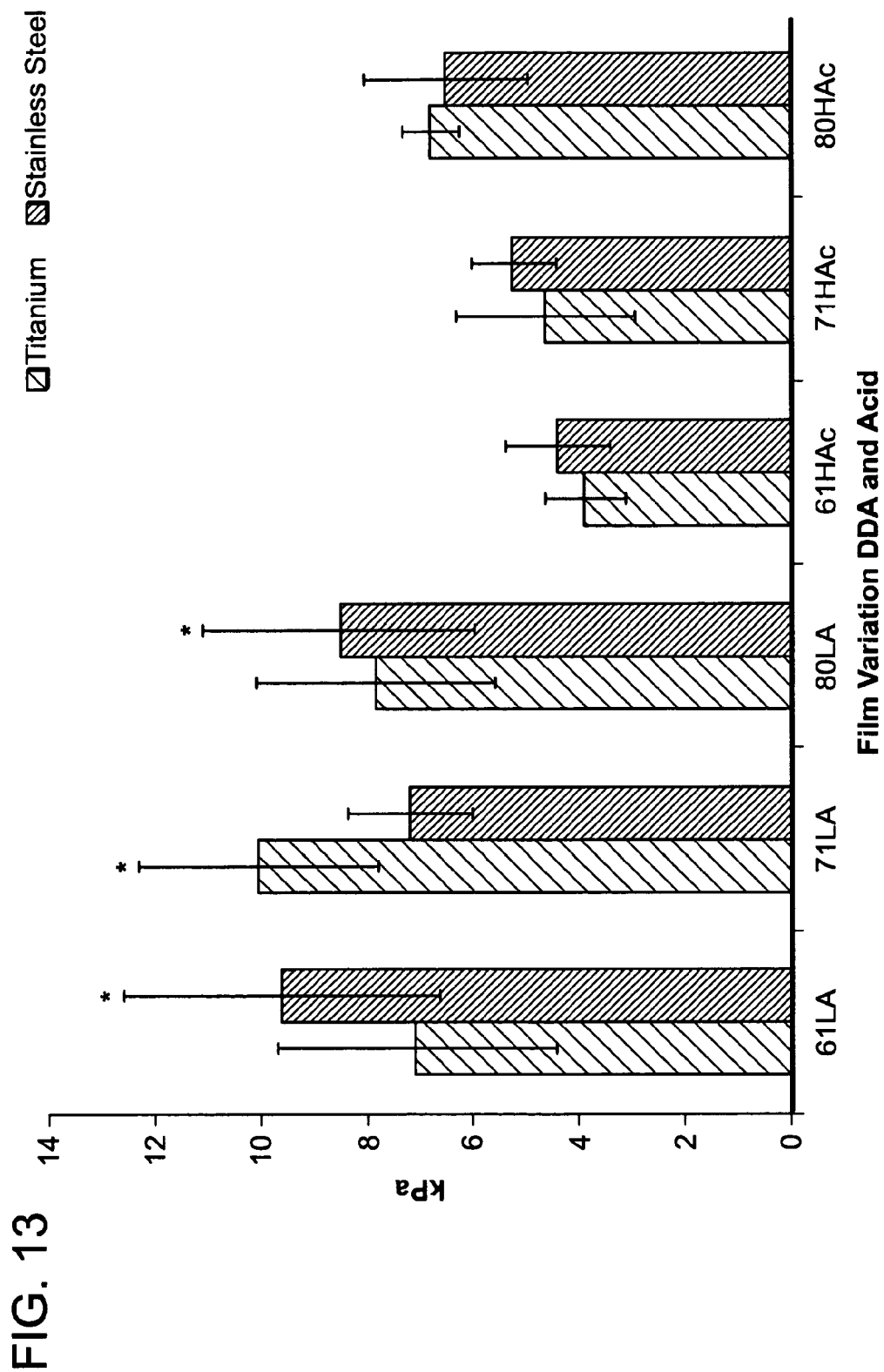
FIG. 13 is a graph showing the results of adhesion testing of chitosan films. Adhesion testing measures adhesive strength, i.e. the maximum tensile load per area, in kPa. The adhesive strength of chitosan films rehydrated for 1 min to titanium and stainless steel alloy substrates was used to measured. Adhesive strength is represented as the average±standard deviation (* vs. all others, p≤0.0310). These results indicated that 61% and 80% DDA, lactic acid film variations on SS, and 71% DDA, lactic acid films on Ti variations have the highest adhesive strength. 71LA films on titanium alloy fixtures had significantly higher adhesive strength than all other variations except for SS61LA and Ti71LA. n=6 measurements for all groups. left column, titanium; right column, stainless steel.

To customize chitosan film's degradation and drug delivery, the degree of chitosan deacetylation (DDA) is varied at 61, 71, and 80% while the film's acid solvent was varied between acetic (HAc) and lactic (LA) acids. Strength and elasticity measurements were obtained using the device shown in FIG. 12. Strength and elasticity results using UTS and Young's modulus indicated that 71 and 80% degree of deacetylation films with acetic acid solvent had the highest strength and elasticity (FIGS. 9, 10, and 13). Two antibiotics, daptomycin (D) and vancomycin (V), were used to treat drug susceptible *Staphylococcus aureus* (FIGS. 7, 8, 11A and B, 14A and 14B). Two-way ANOVA was performed to determine if there was any interaction among DDA and acid solvent independent variables. For antibiotic uptake, swelling ratio, UTS, Young's modulus, and adhesive strength there was no statistical interaction between DDA and acid solvent ($p \geq 0.0674$).

Films using 80% degree of deacetylation absorbed large quantities of antibiotics indicating they are useful as drug delivery devices (FIG. 7). The uptake of daptomycin and vancomycin indicated the amount of antibiotic a dehydrated film could absorb in 1 minute in terms of milligrams of antibiotic per grams of chitosan (FIG. 7). As used herein, daptomycin is abbreviated as D, vancomycin as V, and neither as N; the numbers 61, 71, and 80 are used to indicate the % degree of deacetylation; the acid solvents, lactic acid and acetic acid, are abbreviated LA and HAc, respectively. Film variations V80HAc, D61LA, D71LA, and D80LA were all statistically similar ($p \leq 0.7769$) and absorbed significantly more antibiotic than other variations ($p < 0.0001$). When absorbing daptomycin, lactic acid films had a significantly higher absorption than acetic acid films ($p < 0.0001$). When absorbing vancomycin, acetic acid films had a significantly higher absorption than lactic acid films ($p < 0.0001$). Lactic acid films absorbed daptomycin at an average of 270.80±125.08 mg/g which was significantly higher ($p < 0.0001$) than its average exclusion of vancomycin at −23.12±31.67 mg/g. Conversely, acetic acid films absorbed vancomycin at an average of 118.39±101.93 mg/g, which was significantly higher ($p < 0.0001$) than its average exclusion of daptomycin at −46.43±77.56 mg/g. Chitosan films absorbed antibiotics differently depending on both the type of acid and DDA, with best results occurring when lactic acid films having 80% degree of deacetylation absorb daptomycin and acetic acid films having 80% degree of deacetylation absorbs vancomycin. There was an upward trend of increasing antibiotic absorption as the film's degree of deacetylation increased. Antibiotic exclusion from the chitosan film during in situ loading was indicated by a negative uptake value.

The swelling ratio indicated the increase in volume of the 1 minute rehydrated films in percentage of volume increased (FIG. 8). After 1 minute in PBS alone, results indicated that the films approximately doubled in volume. Non-loaded films exhibited an approximate 100% swelling or doubling in film volume. Analysis indicated that D80LA and V80HAc variations' swelling ratios were similar ($p = 0.8381$) and significantly higher than every other variation ($p < 0.0001$), except for V71HAc ($p = 0.1703$ and 0.0852 respectively). Generally, when the films were in an antibiotic environment that favored increased uptake, the films had a higher swelling ratio.

The UTS and the Young's modulus of the dry/dehydrated films are shown in FIGS. 9 and 10. The 71HAc and 80HAc groups exhibited UTS values of 55.47±11 and 49.89±3.12 MPa which were statistically similar ($p = 0.2131$). These films also exhibited UTS that were significantly higher than the other test groups (p<0.0001). Similarly, Young's moduli for the 71HAc and 80HAc were statistically similar (810.99±207.64, 762.53±49.62, p=0.06597) and significantly greater than other test groups (p<0.0001). No differences were detected in UTS or elastic modulus values of the other test groups.

Films using lactic acid showed the benefit of increased adherence to implant alloys. A chitosan film having an 80% degree of deacetylation provides desirable amounts of antibiotic and mechanical properties that indicate it is ideally suited for drug delivery to a site of trauma. Adhesion testing indicated the adhesion strength, or the maximum tensile load per area in kPa (FIG. 13). Adhesive strength was measured according to standards promulgated by ASTM International (Designation D5179-02, www.astm.org/Standards/D5179.htm, which is incorporated herein by reference in its entirety). Ti71LA, SS61LA, and SS80LA alloy/film variations were statistically similar, and apart from those variations, Ti71LA had significantly higher adhesive strength than every other alloy/film combination (p≤0.0310). Generally, acetic acid film variations had lower adhesive strength than lactic acid variations (LA: ~7-10 kPa v. HAc: ~4-7 kPA). In acetic acid films there was an upward trend in adhesive strength as degree of deacetylation increases. Additional studies indicated that in situ antibiotic loading did not have a statistically significant effect on adhesion strength when compared to rehydration alone. Film adhesion of chitosan films in situ loaded with antibiotics did not significantly differ from that of non-loaded chitosan films, suggesting adhesive uses of the antibiotic-loaded chitosan films (e.g., as an adjunctive antibiotic wrap on a musculoskeletal device). In one embodiment, tensile strength is at least about 45, 50, 55, 60, 65, or 70 mPA. In another embodiment, Young's modulus is at least about 700, 800, 900, or 1000 mPA. In another embodiment, the adhesive strength is at least about 6-12 kPA (e.g., 6, 7, 8, 9, 10, 11, 12 kPA).

Figure 11B:
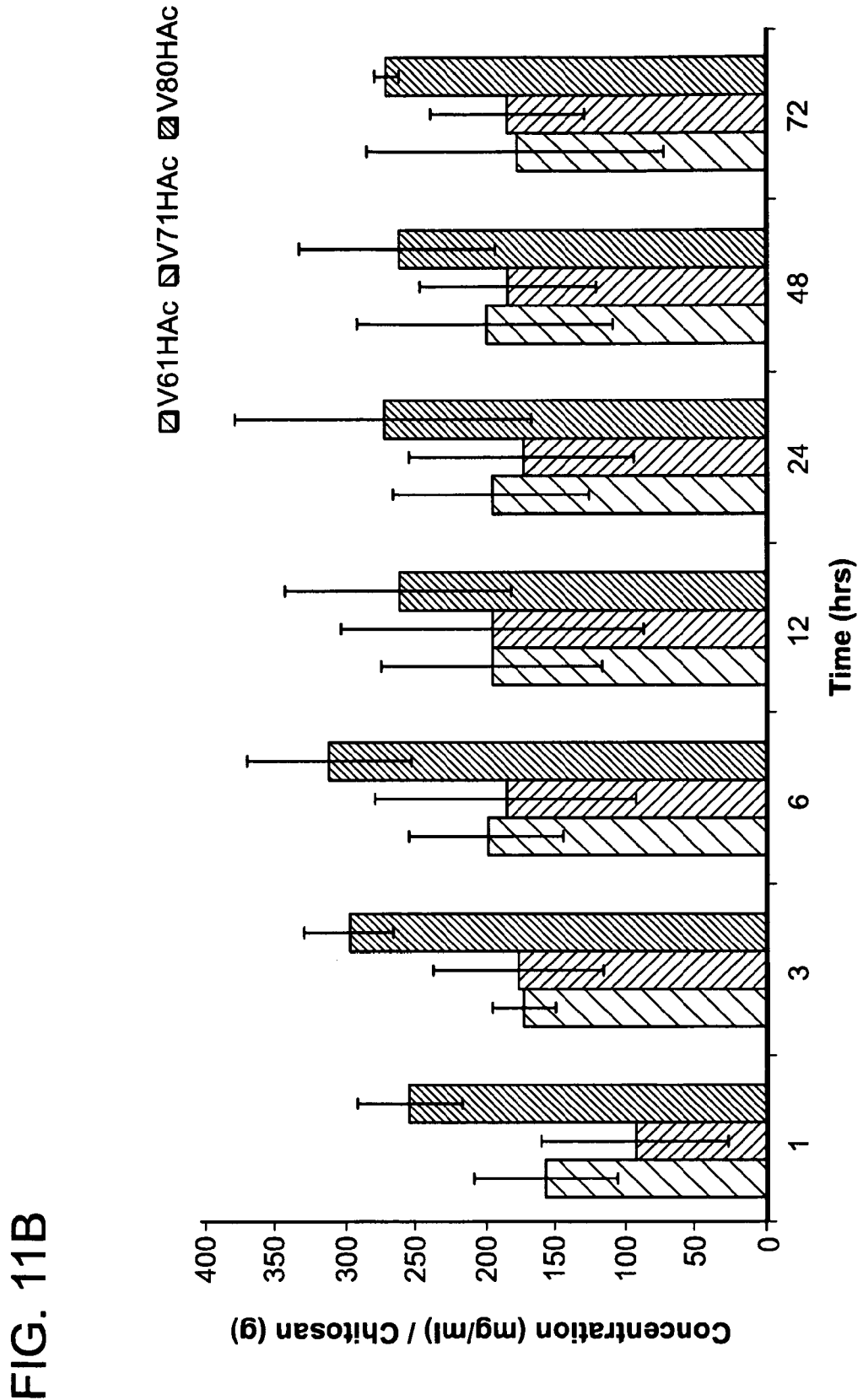

Antibiotic elution results from the films indicated the concentration of antibiotic present in solution per chitosan film sample weight over a period of time given in (mg/ml)/g (FIGS. 11A and 11B). For daptomycin (FIG. 11A), 80LA variations eluted consistently significantly higher quantities of daptomycin over the 72 hour period. This increased elution could be correlated to the increased antibiotic uptake (FIG. 7). In vancomycin elution (FIG. 11B), 80HAc variations had a higher average elution rate. The 72 hour elution's approximate antibiotic release for each individual film variations remained in the same range, except for V71HAc and D71LA, which showed a short but relatively extended release in comparison to their maximum eluted concentration, although this difference was not significant.

Figure 15A:
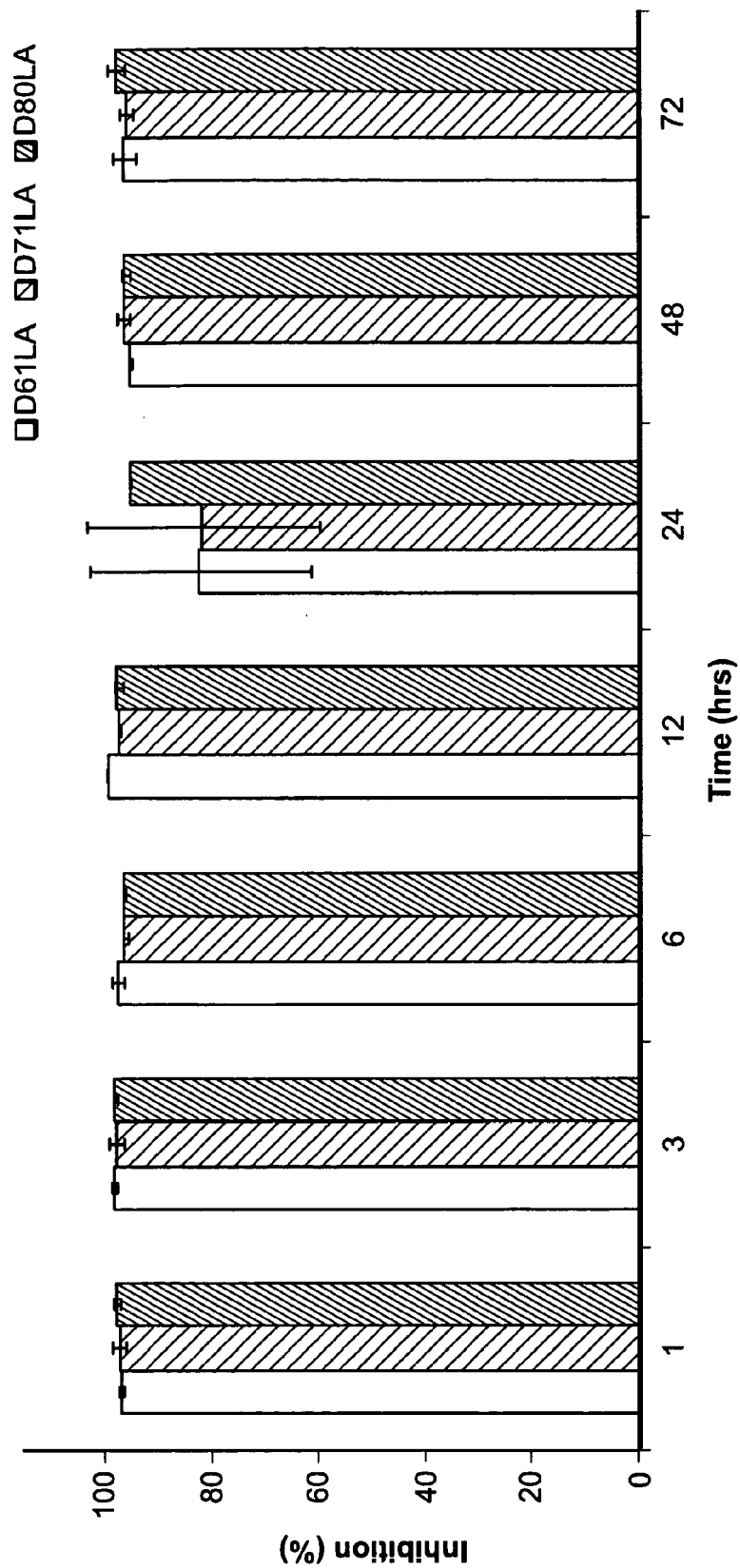
FIGS. 15A and 15B show the antibiotic activity of elution samples.
Figure 15B:
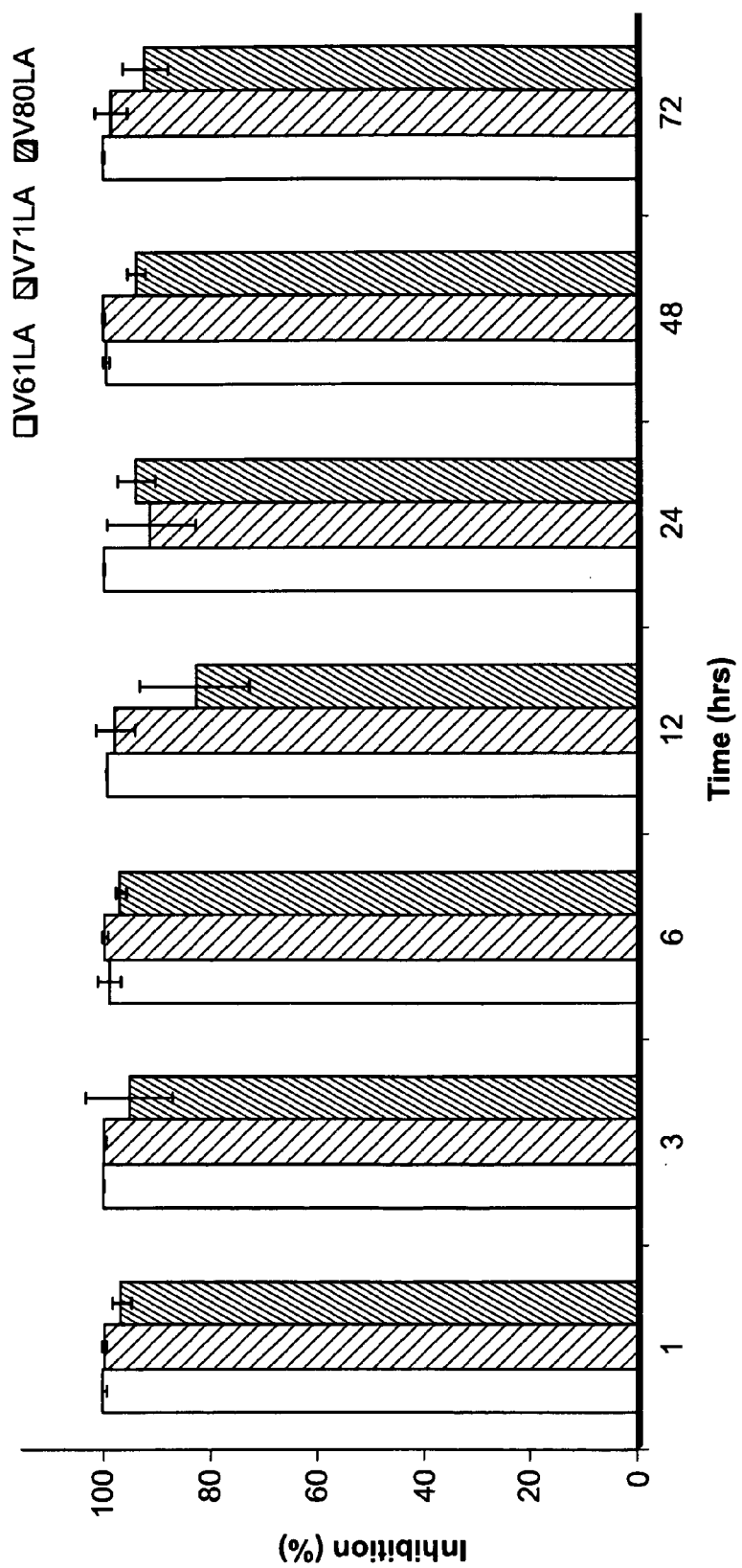
Figure 16:
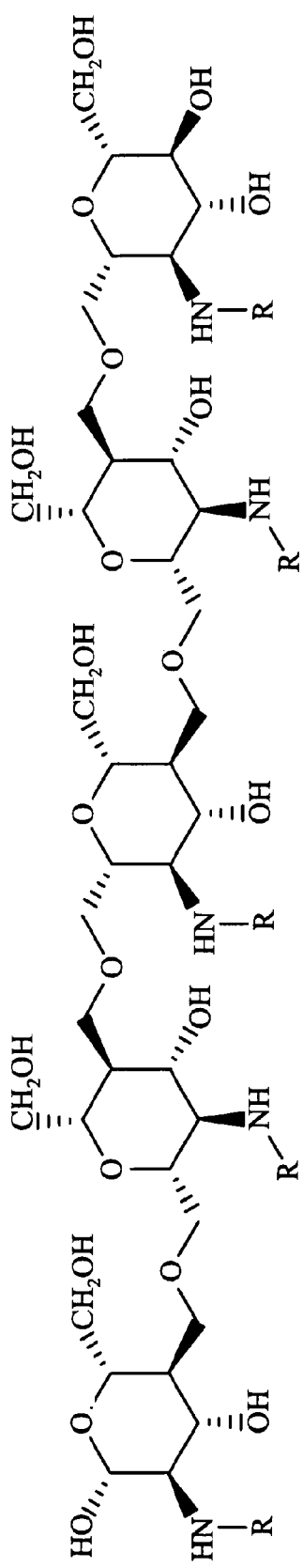
FIG. 16 shows the molecular structure of a chitosan polymer. R functional groups are either H (deacetylated) or COCH3 (acetylated) units.

Antibiotic activity was determined using turbidity assays, indicated by the percent inhibition of S. aureus growth (FIGS. 15A and 15B). Overall, the eluates from the films inhibited S. aureus at all time points. Four variations showed variability at their respective time points: V80HAc at 12 hrs; V71HAc, D61LA, and D71LA at 24 hrs. However, a potential source of variability for V80HAc and V71HAc at 12 and 24 hrs, respectively, may have been caused by a precipitous interaction between the eluates and a component in the TSB media (FIG. 15B). Ultimately, the 48 and 72 hr eluate samples for both vancomycin and daptomycin were found to be active in inhibiting the growth of S. aureus.

Figure 14A:
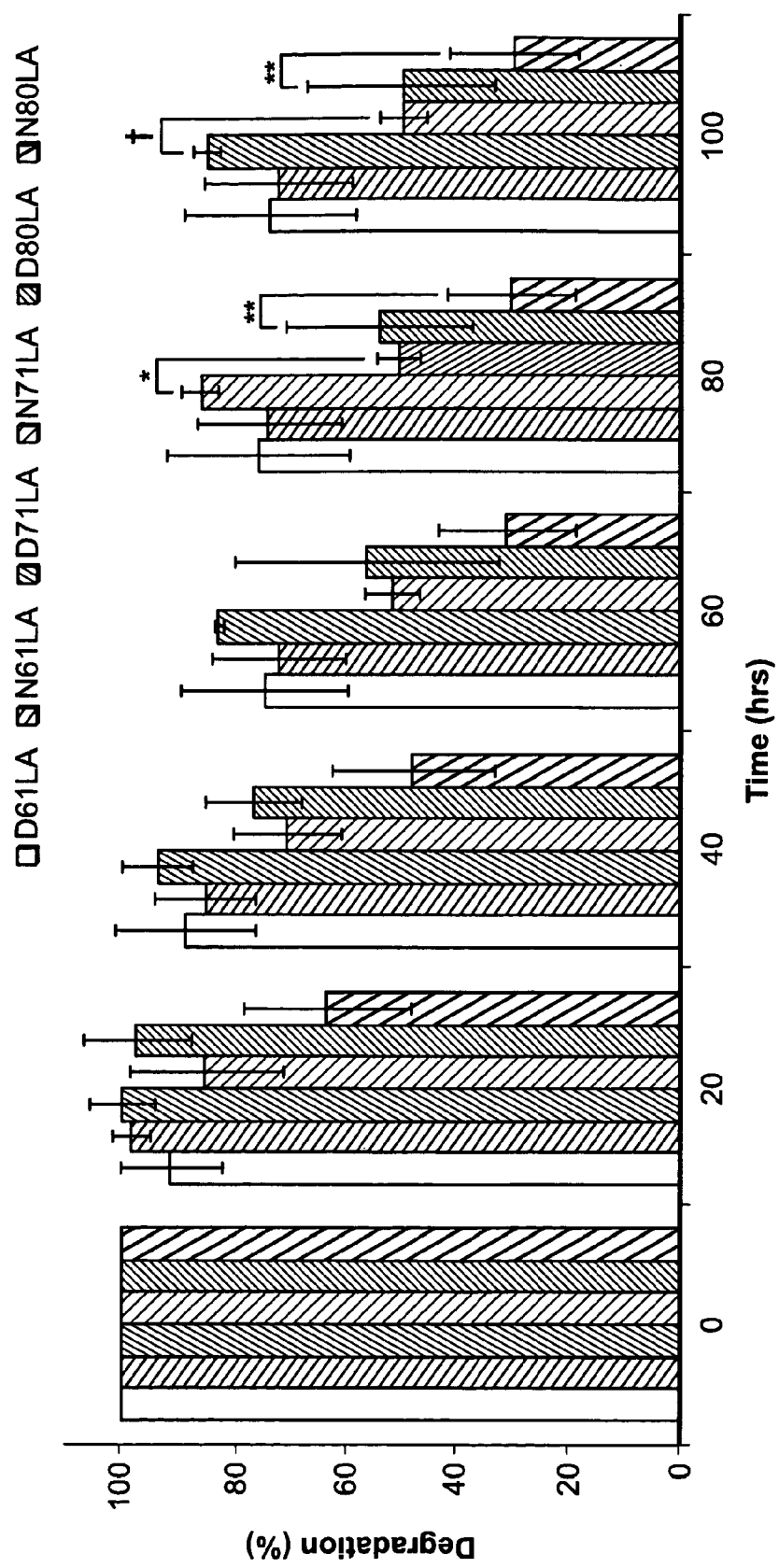
FIGS. 14A and 14B show the degradation of chitosan films with and without antibiotics.
Figure 14B:
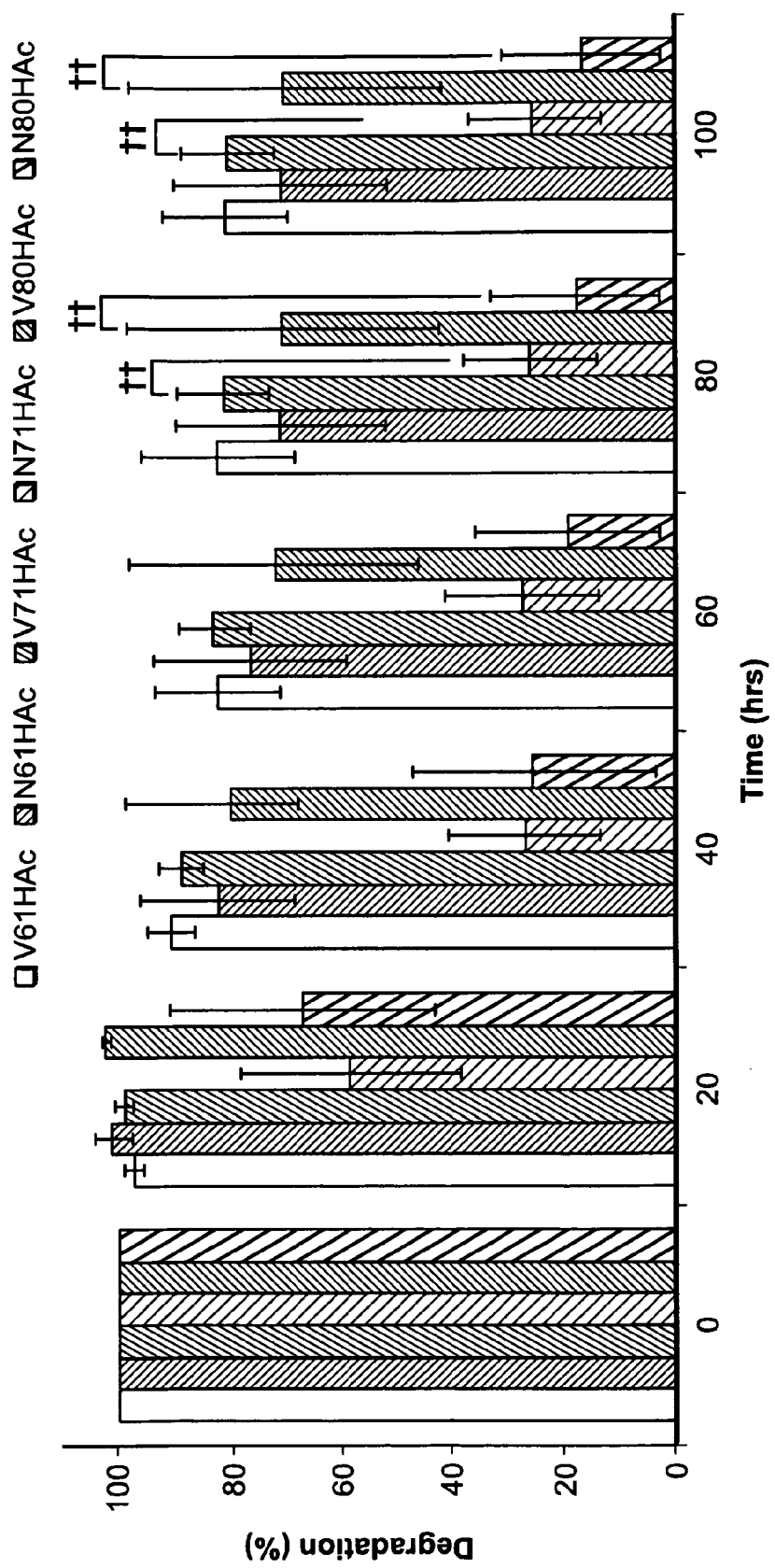

Degradation of chitosan films with and without antibiotics is shown in FIGS. 14A and 14B. The degradation study with lysozyme indicated the chitosan film weight that remained after a period of time in percentage of original film weight (FIGS. 14A and 14B). Film variations with 61% DDA degraded to a lesser extent and with no significant difference between antibiotically loaded and non-loaded variations. Variations with higher DDAs degraded more than those with a lower DDA. When antibiotic loading had an effect, the effect was a decrease in the film degradation amount. After approximately 60 hrs, the degradation rate slowed considerably as each individual variation's percentages were statistically similar after that point.

Chitosan films absorb antibiotic differently depending on both the acid used to form the film and the degree of chitosan deacetylation. In general, optimal results were obtained in films comprising 80LA loaded with daptomycin and 80HAc loaded with vancomycin. Optimizing the chitosan matrix, antibiotic, and acid solvent produces a film that provides for the absorption of multiple antibiotics and that provides for extended antibiotic release. Advantageously, the film is biocompatible and can be used in conjunction with prosthetic devices.

Example 4

Antibiotic-Loaded Chitosan Sponges Prevent Bacterial Colonization on Implanted Catheters in an Established Murine Model Local drug delivery provides an improved approach to combating the formation of biofilms on implant surfaces. Prophylactic treatment of implants with antibiotics to prevent surface colonization and subsequent biofilm formation reduces the risk of biofilm formation. A chitosan local delivery system offers the benefit of bolus antibiotics at the implant site delivered in a degradable matrix. A chitosan local delivery system that is degradable matrix has advantages over non-degradable carriers such as polymethylmethacrylate (PMMA) beads. Drawbacks to using PMMA beads include removal surgery, subtherapeutic release of antibiotics, and bacterial colonization on the implant surface. The study presented below showed that the prophylactic use of a daptomycin-, vancomycin-, or linezolid-loaded chitosan sponge significantly decreases the bacterial counts of a CA-MRSA isolate in an established murine catheter model when compared to PBS-loaded chitosan sponges or catheter-only controls.

To evaluate the loaded chitosan sponge as a prophylactic treatment in preventing biofilm formation on an implantable fluorinated ethylene propylene (FEP) catheter, we used a *Staphylococcus aureus* strain (FPR3757) that has been described previously. This USA300 strain was chosen due to it having a sequenced genome and the fact that it is a prototype community-acquired methicillin-resistant *staphylococcus aureus* (CA-MRSA) isolate.

Figure 21A:
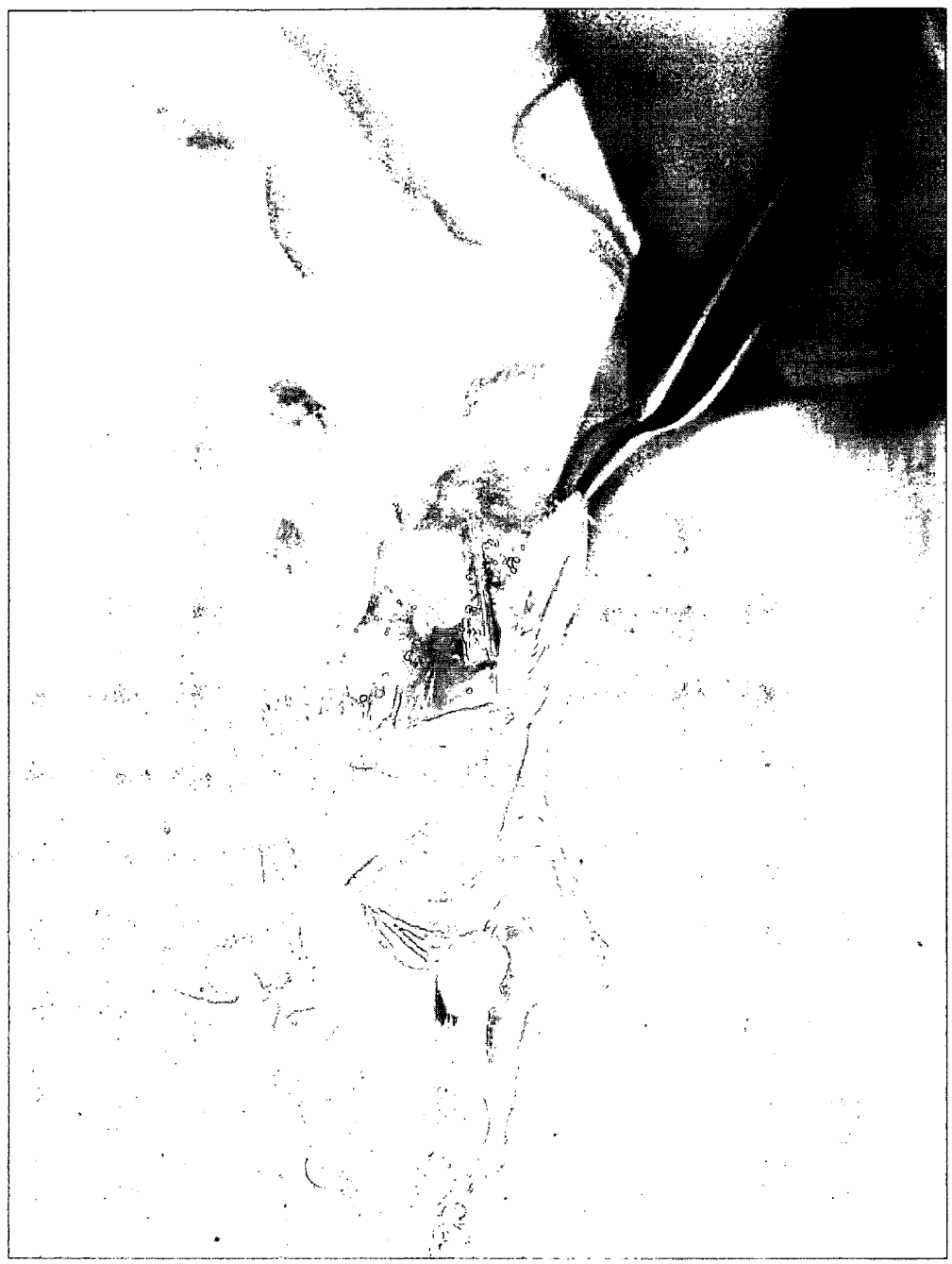
FIGS. 21A and 21B are images depicting a chitosan sponge implanted adjacent to the catheter surface subcutaneously in the hind limb of a mouse. The chitosan sponge was implanted immediately prior to implantation of the catheter segment. Injection of 100 µl of $10^5$ CFU of bacterial inoculum (USA300, CA-MRSA) was done into the lumen of the catheter.
Figure 21B:

Biofilm formation/inhibition was assessed in vivo using a murine model of catheter-associated biofilm formation. Five study groups were evaluated during this study: (a) daptomycin-loaded chitosan sponges, (b) vancomycin-loaded chitosan sponges, (c) linezolid-loaded chitosan sponges, (d) phosphate buffered saline (1×PBS)-loaded chitosan sponges, and (e) catheter only. Sterile chitosan sponges (7.0 mm diameter) were loaded with 125 microliters (μl) of daptomycin solution, vancomycin solution, linezolid solution, or 1×PBS (groups a-d). Concentration values for daptomycin, vancomycin, and linezolid were 10.0 μg/ml, 20.0 μg/ml, and 40.0 μg/ml, respectively. These values correspond to 10 times the concentration defined by the Clinical and Laboratory Standards Institute (CLSI) as the breakpoint MIC for a drug-sensitive strain of *S. aureus*. Subcutaneous pockets were created in the hind limb of NIH Swiss mice (FIGS. 21A and 21B). Immediately prior to implantation of 1-cm segments of catheters, chitosan sponges were placed in the wound (groups a-d) (n=6) (FIGS. 21A and 21B). Because each mouse had two catheters implanted, and because preliminary experiments confirmed the absence of cross-contamination between catheters in opposite flanks of the same mouse, each catheter subsequently was treated as an independent data point (n=12). Group (e) received catheter placement with no chitosan sponge. After implantation of all catheters (approximately 1 h), $10^5$ CFU of the test strain in a total volume of 100 µl of 1×PBS was introduced directly into the lumen of the catheter. Because this study was intended to evaluate the prophylactic efficacy of the chitosan delivery system to prevent biofilm formation, catheters were harvested after animal sacrifice at 48 h post-inoculation. Catheter segments were harvested and rinsed in sterile PBS to remove non-adherent bacteria. Adherent bacteria were removed by sonication in 5.0 ml of PBS. Quantification of viable bacteria colonizing each catheter was determined by plating appropriately diluted samples on tryptic soy agar (TSA). Samples were incubated overnight at 37° C. Quantitative bacterial counts were calculated based on the number of colonies obtained multiplied by the corresponding dilution factor.

Bacterial count data was analyzed using non-parametric methods after testing for normality. Specifically, data were subjected to the Mann-Whitney test followed by Wilcoxon rank-sum pairwise testing. Data were analyzed using JMP 8 (Cary, N.C.). Data were considered significantly different if $p \leq 0.05$.

Figure 22:
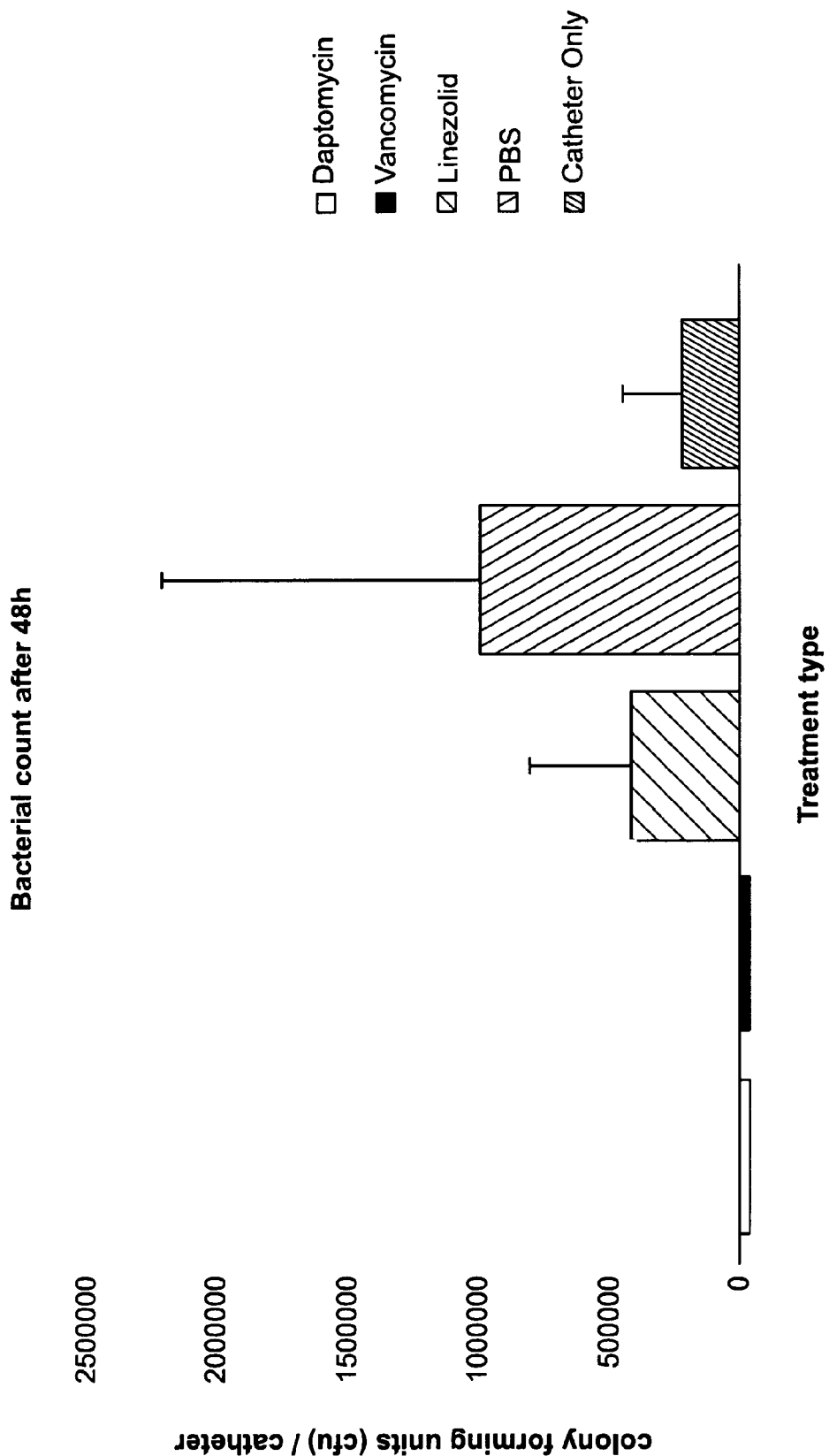
FIG. 22 is a graph showing catheters retrieved from the subjects with daptomycin-loaded and vancomycin-loaded chitosan sponges had no bacteria present in all retrieved implants. Colony forming units per retrieved catheter within each treatment type are graphed. \ The groups containing linezolid-loaded and PBS-loaded chitosan sponges as well as the catheter only controls all had colonized bacteria present on the implant. The daptomycin- and vancomycin-loaded chitosan sponge groups were statistically significant from the other 3 groups in terms of cfu/catheter ($p<0.0001$). The other 3 groups were not statistically significant from each other. (n=12)

The efficacy of an antibiotic-loaded, degradable delivery system to prevent the formation of a CA-MRSA biofilm on an implantable catheter surface in an established murine model was assessed. Groups containing daptomycin- and vancomycin-loaded chitosan sponges prevented colonization of bacteria on the implant surface in 100% of the retrieved catheter segments, 24 of 24 contained no bacteria after plating (FIG. 22). The bacterial counts for both groups were 0 CFU/catheter. Groups that contained linezolid- and PBS-loaded chitosan sponges as well as catheter-only controls did not inhibit the formation of MRSA-induced biofilms on the FEP catheter surface. The linezolid-loaded chitosan sponge group had a bacterial count of $4.19 \times 10^5$ CFU/catheter. The PBS-loaded chitosan sponge group had a bacterial count of $9.96 \times 10^5$ CFU/catheter. The catheter-only group had lower bacterial counts ($2.30 \times 10^5$ CFU/catheter) but was not statistically significant. Daptomycin- and vancomycin-loaded chitosan sponge groups differed significantly in terms of bacterial counts from the other 3 groups (p<0.0001), but were not statistically different from each other. Groups c, d, and e were not significantly different from each other.

The results presented in this study indicate that the prophylactic use of an antibiotic-loaded chitosan sponge prevents the colonization and subsequent biofilm formation on the surface of an implantable biomaterial. The results suggest that the efficacy of the treatment was drug dependant. This finding is similar to those reported in which daptomycin was the most efficacious drug used against UAMS-1 (MRSA strain). However, previous studies differ because the present study a local antibiotic system is used prophylactically in an in vivo model, as opposed to evaluation of drug activity against MRSA in vitro. In the present study, both daptomycin and vancomycin groups were 100% successful in preventing bacterial colonization. The results reported in this study showed that antibiotic-loaded chitosan sponges have the potential to be used prophylactically for the prevention of CA-MRSA biofilm formation.

The results described herein were obtained using the following methods and materials.

Sponge Preparation

Chitosan sponges were prepared as follows. In one approach, chitosan spongers were prepared by dissolving 4.5 grams (g) of chitosan into 295.5 milliliters (ml) of 1% (v/v) acidic solvent (lactic and/or acetic acids). The chitosan was 71% deacetylated (DDA) acquired from Primex (Siglufjordur, Iceland). In another approach, a chitosan solution was prepared by dissolving 5.0 grams (g) of chitosan into 500 milliters (ml) of 1% (v/v) acidic solvent. The chitosan used was 61 and 71% deacetylated (DDA) from Primex (Iceland). 25 ml of aqueous chitosan was cast into aluminum dishes and frozen for one hour at −80 C. Samples were lyophilized for 48 hours. Sponges were neutralized in sodium hydroxide and washed in distilled water until neutral. Samples were re-frozen and re-lyophilized before sterilization. The sponges were sterilized using low-dose gamma irradiation (25-32 kGy).

In a preferred approach adopted for use in the goat wound treatment model described in Example 2, 2.5 grams of chitosan was dissolved in 247.5 ml of 1 (v/v) % blended acid solvent. The mixture contained 75%/25% lactic to acetic acid. This mixture was stirred for 4-6 hours at maximum allowable speed on a stir plate. The chitosan solution was filtered to remove undissolved chitosan. 25 ml of chitosan solution was pipetted into small aluminum weigh dishes (6 mm diameter). Each dish was frozen at −80 C freezer for 1 hour. The frozen samples were then placed into a freeze-dryer and lyophilize for 48 hours. Sponge samples were neutralized in 0.175 M NaOH— solution for ~30-40 seconds. The sponges were rinsed repeatedly in containers filled with distilled water and pH changes were monitored until the rinsing water was neutral in pH. The re-hydrated sponges were then incubated at −80 C freezer for 1 hour and re-lyophilized for 24-48 hours. The sponges were then sterilized using low-dose gamma irradiation at Wright Medical (25-32 kGy).

A composite containing chitosan sponge in chitosan gel (a "sponge-in-gel" composite) can be made from a chitosan gel component and a chitosan sponge component. A gel "matrix" component is prepared by dissolving chitosan (e.g., as described herein), filtering particulate, and allowing the solution to de-gas overnight. Chitosan solution is transferred into a container and frozen for at least 1 hour (−80° C.). The length of time the chitosan solution is frozen can be adapted to the size of the sponge (e.g., longer freezing time for larger sponges).

After freezing, the frozen samples are lyophilized for ~48 hours and sterilized via gamma irradiation. The lyophilized sponge is not neutralized and is used as the adhesive "gel" matrix. A "sponge" component is prepared using the lyophilized sponges (e.g., as described herein). The lyophilized sponges are neutralized by submerging in sodium hydroxide solution (various concentrations of NaOH may be used). Hydrated sponges are rinsed with water several times before re-freezing for at least 1 hour (−80° C.). The frozen sponges are lyophilized again for 36-48 hours. The duration of lyophilization is dependent on lyophilizer and the size of sponge. The "double" lyophilized sponge samples are sterilized via gamma irradiation.

To prepare the "sponge-in-gel" composite, a combination of "gel matrix" and "sponge" components are coarsely ground (e.g., in a standard coffee grinder). The finer components are the single-lyophilized sponge pieces, and the larger components are the double lyophilized sponge pieces. In one embodiment, at least about 25%-95% of the composite is hydrogel component. In another embodiment, at least about 5%-75% of the composite is sponge. The composite is customized based on the adhesiveness required and/or the size of the wound. An increased amount of adhesiveness is desired if the wound is prone to drainage or has increased surface area. In another embodiment, an increased amount of sponge material is desired for a cavity wound. This blended mixture of single- and double-lyophilized chitosan sponge fragments is then hydrated with a solution (antibiotic, saline, antifungal, etc) to form a paste mixture. The resulting paste has a binding "gel" matrix (single-lyophilized sponge component) with larger, dispersed "sponge" fragments throughout the gel (double-lyophilized sponge component). The "sponge-in-gel" composite can be prepared in a short amount of time. In one embodiment, the paste is mixed and is delivered at the point-of-care. The agent is incorporated at the time the composite is hydrated. In one embodiment, the composite is delivered to a site of trauma via a sterile syringe.

Advantageously, the composite provides for a complete void fill and prevents migration of the chitosan composition within the wound. This facilitates localized delivery of an agent to the site of trauma. The "gel matrix" typically has greater adherence properties than the sponge portion of the composite. Thus, the amount of "gel matrix" can be increased or decreased based on the needs of the patient. In one embodiment, an increased amount of gel matrix (e.g., greater than about 50%, 70%, 80%, 90%, 95%) is used to increase tissue adherence. In another embodiment, an increase amount of sponge fragments (e.g., greater than about 50%, 70%, 80%, 90%, 95%) to provide for sustained elution of an agent over time. Preferably, the composite provides for the bimodal delivery of an agent. In the first phase, an agent is quickly released from the gel matrix. This first phase of elution typically occurs over the course of hours (e.g., 1, 2, 3, 4, 5, 6 or 12 hours) or days (e.g., 1, 2, 3 days). The second phase of the biomodal elution involves the sustained release of an agent from the sponge portion of the composite. This phase typically occurs over the course of days, or weeks. Desirably, the composite provides for sustained elution of an agent during the course of the composite's degradation. In one embodiment, the composite comprises a non-neutralized gel portion. In another embodiment, the composite comprises a neutralized sponge portion.

Sponge Elution Tests

Sponges were subjected to elution tests by submerging hydrated sponges into 20 ml of 1× Phosphate Buffered Saline (PBS), kept in a 37° C. incubator for the duration of the study. Sponges were re-hydrated in 10 ml of 5 mg/ml amikacin and vancomycin loaded solution. One ml aliquots were taken at 1, 3, 6, 24, 48, and 72 hours. Aliquots were tested for antibiotic concentration using a fluorescence polarization immunoassay technique (TDx, Abbott Labs, Abbott Park, Ill.).

Antibiotic Activity

Drug activity of the aliquots was tested using a turbidity assay. Two different strains of bacteria were used in this study. Vancomycin samples were tested against *Staphylococcus aureus* and amikacin samples were tested against both *Staphylococcus aureus* and *Pseudomonas aeruginosa*. 200 μl of each aliquot was added to 1.8 ml of Mueller-Hinton II broth combined with 20 μl of *S. aureus* inoculum. Amikacin samples (200 μl) were also added to 1.75 ml of trypticase soy broth (TSB) and 50 μl of *P. aeruginosa* inoculum. Samples were incubated for 24 hours at 37 C. Absorbance measurements were recorded after incubation at a wavelength of 530 nm (A530).

In other studies, antibiotic activity against *S. aureus* (Cowan I strain) was determined by utilizing the remaining antibiotic elution samples, in triplicate, in a turbidity assay. In this turbidity study, solution clarity after sufficient bacterial incubation with antibiotic eluates indicated bacterial inhibition due to antibiotic activity.

In triplicate, 20 μl of vancomycin and daptomycin eluates were individually added to the inoculum containing 1.75 ml of tryptic soy broth (TSB) and 25 μl of *S. aureus* in 5 ml polystyrene test tubes. Blanks containing neither *S. aureus* nor eluate samples, positive controls containing *S. aureus* without antibiotic eluates, and negative controls containing both *S. aureus* and high concentration antibiotic standards were mixed and incubated at 37° C. along with the eluate samples. After 24 hours of incubation, the tubes were vortexed and the absorbance at 530 nm of each inoculum solution was recorded using a spectrophotometer.

Antibiotic Quantitation

High-pressure liquid chromatography (HPLC) was used to quantify the uptake and elution of the antibiotics vancomycin from MP Biomedicals (Irvine, Calif.) and daptomycin from Cubist Pharmaceuticals (Lexington, Mass.). The Varian (Palo Alto, Calif.) HPLC system comprised a ProStar 240 Solvent Delivery, ProStar 410 Autosampler, and ProStar 325 UV-Vis Detector modules. Module control and data processing were performed using Varian's Galaxie Chromatography Data System (v1.8.508.1). Both HPLC separation methods were modified from previous research.

For daptomycin quantification the mobile phase consisted of an HPLC grade acetonitrile and water (62:38, v/v) solution including 4 mM ammonium dihydrogen phosphate brought to a pH of 3.25 using phosphoric acid. Separation was accomplished using a Varian Microsorb-MV C8 column, 150 mm length and 4.6 mm inner diameter with a flow rate of 1 ml/min. Daptomycin was detected at 232 nm with a retention time of 13.8 minutes (min). Daptomycin quantification was performed in a temperature range of $23.3 \pm 1.1°$ C.

For vancomycin quantification, the mobile phase consisted of a HPLC grade acetonitrile and water (92:8, v/v) solution including 50 mM ammonium dihydrogen phosphate brought to a pH of 4 using phosphoric acid. Separation was accomplished using a Varian Microsorb-MV $C_{18}$ column, 150 mm length and 4.6 mm inner diameter with a flow rate of 1 ml/min. Vancomycin was detected at 208 nm with a retention time of 24.4 min. Vancomycin quantification was performed in a temperature range of $23.3 \pm 1.1°$ C.

Film Elution Tests

In one approach, samples were submerged into 15 ml amikacin solution (5 mg/ml) and allowed to hydrate for 2 minutes. Samples were then subjected to elution tests by submerging the films in 50 ml of 1× Phosphate Buffered Saline (PBS) and agitated in a 37 C incubator for the duration of the study. One ml aliquots were removed at 1, 3, 6, 24, 48, and 72 hours. Aliquots were tested for antibiotic concentration using a fluorescence polarization immunoassay technique (TDx-FLx, Abbott Labs, Abbott Park, Ill.).

In another approach, lactic acid films with three different degrees of deacetylation were measured for daptomycin elution, and acetic acid films with different degrees of deacetylation were measured for vancomycin elution. The elution experiment was performed in triplicate by submerging films in 50 ml of PBS immediately following in situ antibiotic loading at 3 mg/ml of antibiotic. The elution procedure excluded PBS solution refreshment at each time point. The films were then incubated at 37° C. and 0.5 ml aliquots were removed at 1, 3, 6, 12, 24, 48, and 72 hours. The antibiotic concentrations of eluant samples were determined using HPLC to obtain an elution profile for each film/antibiotic combination.

Activity Tests

Drug activity of the aliquots was tested using a turbidity assay. Samples were tested against *Pseudomonas aeruginosa*. Samples (200 µl) were added to 1.75 ml of Trypticase Soy Broth (TSB) and 50 µl of *P. aeruginosa* inoculum. Samples were incubated for 24 hours at 37 C. Absorbance measurements at 530 nm on a spectrophotometer (BioTek).

Film Preparation

Using three chitosan degree of deacetylations and two acid solvents, six chitosan variations were evaluated. The numbers 61, 71, and 80 were used to indicate the % degree of deacetylation (DDA); the acid solvents, lactic acid and acetic acid, are abbreviated LA and HAc, respectively.

Primex ChitoClear (Iceland) chitosan powder at 61, 71, and 80% degree of deacetylation with 124, 1480, and 332 mPas viscosities, respectively, was used to create the films. A 1.5% (w/v) chitosan solution was prepared by dissolving the desired variation in either 1% (v/v) acetic or lactic acid solution, under constant stirring for 24 hours (hr). To remove insolubilities from the chitosan solution, it was filtered through 180 µm nylon, placed in a glass mold and transferred to a convection oven at 60° C. until dry. The dehydrated film was removed and neutralized by placing it in a NaOH solution followed by rinsing in water. This neutralized film was allowed to dry at 25° C. In another approach, a chitosan solution that had been filtered through an 180 µm nylon screen was allowed to degas at 20° C. The solution was placed in a flat-bottomed glass dish at approximately 0.8 ml/cm$^2$ and the solvent was allowed to evaporate in a convection oven at 38° C. for 24 hrs. This produced a dried film which was neutralized by dipping the film in 2 M sodium hydroxide for approximately 1 sec, followed by pouring 2 L of distilled/deionized water over the film for rinsing. The neutralized films were dried on a large-pore sized nylon screen in a convection oven at 38° C. for 12 hrs.

In another approach, 2.5 grams of chitosan was dissolved into 247.5 ml of 1 (v/v) % blended acid solvent containing 75%/25% lactic to acetic acid. The mixture was stirred for 4-6 hours at max allowable speed on a stir plate. The chitosan solution was filtered to remove undissolved chitosan, and the filtrate was pipetted into a glass Petri dish, which was heated at 37° C. for 18-20 hours. The dried films were removed and neutralized in 2.0 M NaOH$^-$ solution for ~30-40 seconds. The films were rinsed with distilled water and pH changes were monitored until the rinsing water was neutral in pH. The re-hydrated films were then frozen at −80° C. freezer for 1 hour and then lyophilized for 24 hours. The films were then sterilized using low-dose gamma irradiation (25-32 kGy).

Film Uptake Studies

An uptake study was performed to determine the quantity of antibiotic solution that each chitosan composition could absorb. Antibiotic uptake determines the ability of chitosan film to absorb antibiotics. This study determined the concentration of both vancomycin and daptomycin that each chitosan film variation could absorb during 1 minute of rehydration. a 1 mg/ml vancomycin or daptomycin phosphate-buffered saline (PBS) solution was created. Using six replications, films of known weights were submerged in 50 ml of the antibiotic solution for 1 min, where 1 min is representative of effective operating room usage. The film was then submerged in the antibiotic solution for thirty seconds and removed. The remaining solution was tested using a high pressure liquid chromatography (Varian, Calif.) method to determine the antibiotic concentration.

This method of antibacterial loading is defined as in situ loading, as opposed to pre-loading, where antibiotics would be incorporated in the chitosan solution during film creation. After 1 minute the film was removed and a sample of remaining antibiotic solution was used in HPLC to determine its concentration. Antibiotic uptake was normalized by film weight and determined using the following relations: Antibiotic uptake=[(Initial antibiotic solution concentration−Final antibiotic solution concentration)×Antibiotic solution volume](mg)/(Chitosan film weight)(mg).

Swelling Ratio.

The swelling ratio of the chitosan films was determined after 1 min submergence in the presence and absence of daptomycin and vancomycin solutions. In order to quantify swelling ratio, the initial volume of chitosan films were determined using electronic digital calipers accurate 0.03 mm within a range of 0 to 150 mm. The final volume was determined immediately after the antibiotic uptake procedure was performed. This data allowed the swelling ratio after 1 minute to be determined using the following relationship: Swelling ratio (%)=(Final film volume−Initial film volume)/(Initial film volume)×100

Absorbed antibiotic quantity was determined using differences in concentrations. Concurrent with the uptake study, film dimensions were measured using digital calipers in order to calculate film volume differences, yielding the swelling ratio. Chitosan film swelling ratio quantified the increase in volume as the film rehydrated.

Ultimate Tensile Strength, Young's Modulus

Neutralized films were subjected to tensile testing using a Universal Materials Testing Machine (Instron, Norwood, Mass.). Ultimate Tensile Strength (UTS) and Young's Modulus determines the strength and elasticity of dry/dehydrated chitosan film variations. Using six replications, film variations were punched out into ASTM E8 tensile testing specimens with an initial 25 mm-gage length and 175 mm$^2$ area. Dehydrated film thickness was 0.29±0.6 mm. In some analyses, test specimens were cut uniformly with gauge lengths and widths of 12.7 mm and 3.5 mm respectively. Using an Instron 33R, model 4465 (Norwood, Mass.) Universal Testing Machine with a 50 N load cell automated by Instron's Bluehill 2 (v2.13) software, the ultimate tensile strength (UTS) and Young's modulus of dehydrated films were determined. Due to the necessity of controlling the test specimen's precise dimensions, it was necessary to perform this test using dehydrated chitosan film samples. The test specimen was securely placed in the hydraulic grips and tested in tension at a rate of 1 mm/min with data recorded at 200 ms intervals. The testing device software was configured to output UTS, Young's modulus and the breaking point % of elongation.

Adhesive Strength

Adhesive strength measurement investigates the adhesive strength of wet/rehydrated chitosan films to implant grade alloy fixtures, either 316L stainless steel (ASTM F138) or 6-4 titanium (ASTM F136), using a modified ASTM standard (D5179-02). These fixtures were gripped by a universal testing machine which measured the strength required to pull the implant alloys apart. All experiments were performed with n≥5.

To determine adhesive strength, six specimen replications from all chitosan film variations were cut into minimal 38×38 mm squares. Films were then submerged in 50 ml of PBS solution for 1 min, in order to simulate the in situ loading procedure, and were then positioned between cylindrical fixtures with a diameter of 35.1 mm to facilitate the adhesion test. The adhesion testing was modeled from ASTM D5179-02 in order to be performed in-house. Both Instron Universal Testing Machine hydraulic grips were made to hold either 316L SS (ASTM F138) or Ti (Ti-6A1-4V, ASTM 136) alloy fixtures (FIG. 12). The mechanical fixture surfaces which faced each other were smoothed by superfinishing to a roughness, $R_a$, value of 0.025 µm. The superfinishing on the testing cylinders were used to provide comparison testing, not to replicate typical implant surfaces. The rehydrated chitosan film was sandwiched between the two mechanical fixtures with an automatic compression pre-load of 15 N. Immediately after reaching the pre-load force, the movable crossheads were reversed at 50 mm/min with data recorded at 30 millisecond intervals. Film thickness varied at 0.18±0.8 mm and the software gave data output in maximal force (N) which was converted into adhesive strength (kPa). Tukey's HSD statistical analysis was performed with α=0.05 to determine statistical differences between film variations.

Chitosan Degradation.

A modified procedure (Tomihata and Ikada, 1997) was used to quantify the antibiotic effect on chitosan degradation. In situ loaded and non-loaded chitosan films groups—the same groups used in the antibiotic elution and activity experiments with additional non-loaded groups yielded a total of 12 experimental groups to be tested with five replicates each—were subjected to degradation testing. The weight of clean 90 mm diameter Petri dishes and dehydrated chitosan films was established. Films marked for in situ loading were submerged in 50 ml of a standard antibiotic solution and then all films were submerged in 25 ml of 100 µg/ml 2× crystallized, chicken egg white lysozyme (MP Biomedicals) PBS solution. The samples were incubated for 20 hours at 37° C. in a convection incubator. After the incubation period, the lysozyme solution was removed and the films were dehydrated using the same method with the convection oven. The lysozyme/PBS solution was replaced and film weights were measured every 20 hours for a total of 100 hours. The new film weights were measured, which enabled degradation to be expressed as the percent of the film that remained. The percent of the film that remained was determined using the following relationship: Percent Remaining (%)=(Petri dish and film weight at x hours–Petri dish weight)(mg)/(Petri dish and initial film weight–Petri dish weight)(mg)×100.

Statistical Analysis

Data is reported as the mean±standard deviation. One-way ANOVA was used to analyze for statistically significant differences. If statistically significant differences were found, then each pair of variations were compared using the Student t-test. Differences between chitosan film variations were determined using the Student t-test. Two-way ANOVA was used to identify differences between DDA and acid solvent independent variables. Analysis was performed using JMP 7.0.1 (Cary, N. Dak.). Statistical significance occurred when $p<0.05$ and are indicated by either * or †.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for producing a biodegradable chitosan composition having a desired biodegradation profile, the method comprising
   (a) dissolving chitosan having a degree of deacetylation of at least about 51% in one or more acids in a solvent, wherein the acid and solvent are selected to produce a biodegradable chitosan;
   (b) forming the chitosan into a desired shape and lyophilizing to reduce the water content by about 80% 100%;
   (c) neutralizing the chitosan composition by contacting the composition with a basic solution, wherein the basic solution is selected to modulate a physical-mechanical property of the chitosan;
   (d) washing the chitosan composition with water until neutral; and
   (e) lyophilizing the composition of step (c) to reduce the water content by about 80%-100%, thereby producing a biodegradable chitosan composition.

2. The method of claim 1, further comprising incorporating at least one antibacterial or antifungal agent into the chitosan composition at a point of care.

3. The method of claim 1, wherein the chitosan degree of deacetylation, weight percent, neutralization solution, solvent make-up, and/or crystallinity is selected to customize the biodegradation profile, elution profile, and/or a physical-mechanical property of the chitosan composition.

4. A method for producing a biodegradable chitosan composition comprising an antibacterial or antifungal agent selected by a clinician at a point of care, the method comprising
   (a) dissolving chitosan having a degree of deacetylation of at least about 51% in one or more acids in a solvent, wherein the acid and solvent are selected to produce a chitosan that biodegrades over at least about one, two, three, four or five days in vivo; and
   (b) forming the chitosan into a desired shape and lyophilizing to reduce the water content by about 80%-100%;
   (c) neutralizing the chitosan composition by contacting the composition with a basic solution, wherein the basic solution is selected to modulate a physical-mechanical property of the chitosan;
   (d) washing the chitosan composition with water until neutral; and
   (e) lyophilizing the composition of step (c) to reduce the water content by about 80%-100%;
   (f) selecting an antibacterial or antifungal agent; and
   (g incorporating an effective amount of the agent into the composition at a point of care.

5. The method of claim 1, wherein the method is ex vivo.

6. The method of claim 1, wherein the physical-mechanical property is selected from the group consisting of tensile strength, Young's modulus, swelling, degradation, and a combination thereof.

7. The method of claim 1, wherein the chitosan composition is a wound management device.

8. The method of claim 4, wherein the antibacterial or antifungal agent is selected at the point of care.

9. The method of claim 1, wherein the desired shape is obtained by pouring the chitosan into a thin layer and heating the chitosan to form a dehydrated chitosan film.

10. The method of claim 1, wherein the chitosan is treated with an acid selected from the group consisting of acetic, citric, oxalic, proprionic, ascorbic, hydrochloric, formic, salicylic and lactic acids.

11. The method of claim 10, wherein the acid solvent comprises lactic acid and/or acetic acid.

12. A chitosan composition produced by the method of claim 1.

13. A wound management device comprising a chitosan composition produced by the method of claim 1.

14. A method for treating a bacterial or fungal infection in a subject at a site of trauma, the method comprising contacting the site with a wound management device of claim 13 and an effective amount of at least one anti-bacterial or anti-fungal agent selected at a point of care.

15. A method for the local delivery of an antibacterial or antifungal agent to a site of a subject, the method comprising contacting the site with a chitosan composition according to the method of claim 1 comprising an antibacterial or antifungal agent selected at the point of care, thereby delivering the agent to the site.

16. A medical device for implantation and delivery of an antibacterial or antifungal agent to the implantation site comprising a chitosan composition made according to the method of claim 1.

17. A kit comprising a chitosan composition of claim 1.

* * * * *